US012807974B2

(12) United States Patent
Liu et al.

(10) Patent No.: US 12,807,974 B2
(45) Date of Patent: Nov. 24, 2026

(54) PROCESSES FOR PRODUCING FERMENTATION PRODUCTS USING FIBER-DEGRADING ENZYMES IN FERMENTATION

(71) Applicant: Novozymes A/S, Bagsvaerd (DK)

(72) Inventors: Jiyin Liu, Raleigh, NC (US); Hui Xu, Wake Forest, NC (US); James Lavigne, Wake Forest, NC (US); Lan Tang, Beijing (CN); Kim Borch, Birkerod (DK); Jesper Frickmann, Raleigh, NC (US); Geoffrey Moxley, Wake Forest, NC (US); Qiming Jin, Sacramento, CA (US); Ye Liu, Beijing (CN)

(73) Assignee: Novozymes A/S, Bagsvard (DK)

( * ) Notice: Subject to any disclaimer, the term of this patent is extended or adjusted under 35 U.S.C. 154(b) by 203 days.

(21) Appl. No.: 18/572,135

(22) PCT Filed: Jun. 29, 2022

(86) PCT No.: PCT/CN2022/102201
§ 371 (c)(1),
(2) Date: Dec. 19, 2023

(87) PCT Pub. No.: WO2023/274282
PCT Pub. Date: Jan. 5, 2023

(65) Prior Publication Data

US 2025/0129393 A1 Apr. 24, 2025

(30) Foreign Application Priority Data

Jun. 29, 2021 (WO) ................ PCT/CN2021/103075

(51) Int. Cl.

| | |
|---|---|
| ***C12P 7/06*** | (2006.01) |
| ***C12N 9/26*** | (2006.01) |
| ***C12N 9/42*** | (2006.01) |
| ***C12N 15/81*** | (2006.01) |
| ***C12P 7/10*** | (2006.01) |

(52) U.S. Cl.

CPC .............. *C12P 7/06* (2013.01); *C12N 9/2414* (2013.01); *C12N 9/2437* (2013.01); *C12N 9/2445* (2013.01); *C12N 15/81* (2013.01); *C12P 7/10* (2013.01); *C12Y 302/01001* (2013.01); *C12Y 302/01004* (2013.01); *C12Y 302/01021* (2013.01); *C12Y 302/01091* (2013.01); *C12N 2800/102* (2013.01)

(58) Field of Classification Search

CPC . C12P 7/06; C12P 7/10; C12N 9/2414; C12N 9/2437; C12N 9/2445; C12N 15/81; C12N 2800/102; C12N 9/2417; C12N 15/80; C12Y 302/01001; C12Y 302/01004; C12Y 302/01021; C12Y 302/01091; C12R 2001/645; Y02E 50/10
See application file for complete search history.

(56) References Cited

U.S. PATENT DOCUMENTS

| | | | | |
|---|---|---|---|---|
| 6,127,160 | A * | 10/2000 | Yamanobe | C12N 9/2437 435/320.1 |
| 7,256,031 | B2 * | 8/2007 | Fukasawa | C12Y 302/01021 536/23.4 |
| 7,820,419 | B2 | 10/2010 | Smith et al. | |
| 9,481,897 | B2 * | 11/2016 | Liu | C12P 7/10 |
| 10,266,814 | B2 * | 4/2019 | Mort | C12P 19/14 |
| 10,676,751 | B2 * | 6/2020 | Daniell | C12Y 302/01021 |
| 2013/0137152 | A1 | 5/2013 | Landvik et al. | |
| 2018/0155744 | A1 | 6/2018 | Cripwell et al. | |
| 2019/0323041 | A1 | 10/2019 | Rasmussen et al. | |
| 2021/0079430 | A1 | 3/2021 | Attfield | |

FOREIGN PATENT DOCUMENTS

| | | | |
|---|---|---|---|
| EP | 3360956 | A1 | 8/2018 |
| WO | 1999061651 | A2 | 12/1999 |
| WO | 0226979 | A1 | 4/2002 |
| WO | 2006114095 | A1 | 11/2006 |
| WO | 2009133035 | A1 | 11/2009 |
| WO | 2009138877 | A2 | 11/2009 |
| WO | 2010053838 | A1 | 5/2010 |
| WO | 2010060056 | A2 | 5/2010 |
| WO | 2011128712 | A1 | 10/2011 |
| WO | 2011153516 | A2 | 12/2011 |
| WO | 2013028928 | A1 | 2/2013 |

(Continued)

OTHER PUBLICATIONS

Banerjee et al., Improving enzymes for biomass conversion: A basic research perspective. Bioenerg. Res., 2010, vol. 3: 82-92. (Year: 2010).*

Broun et al., Catalytic plasticity of fatty acid modification enzymes underlying chemical diversity of plant lipids. Science, 1998, vol. 282: 1315-1317. (Year: 1998).*

Chica et al., Semi-rational approaches to engineering enzyme activity: combining the benefits of directed evolution and rational design. Curr. Opi. Biotechnol., 2005, vol. 16: 378-384. (Year: 2005).*

(Continued)

*Primary Examiner* — Ganapathirama Raghu

(74) *Attorney, Agent, or Firm* — Eric J. Fechter

(57) ABSTRACT

Provided is a subject matter relates to a process for producing fermentation products from starch-containing material comprising the steps of: i) saccharifying using a carbohydrate-source generating enzyme; ii) fermenting using a fermenting organism; wherein at least one polypeptide having cellobiohydrolase activity, endoglucanase activity, or beta-glucosidase activity are present or added during fermentation or simultaneous saccharification and fermentation. The subject matter also relates to an enzyme blend or composition comprising the polypeptides.

32 Claims, 4 Drawing Sheets

Specification includes a Sequence Listing.

(56) References Cited

FOREIGN PATENT DOCUMENTS

| | | | |
|---|---|---|---|
| WO | 2013052831 | A2 | 4/2013 |
| WO | 2013091577 | A1 | 6/2013 |
| WO | 2013138357 | A1 | 9/2013 |
| WO | 2014059541 | A1 | 4/2014 |
| WO | 2015109405 | A1 | 7/2015 |
| WO | 2016005521 | A1 | 1/2016 |
| WO | 2016005522 | A1 | 1/2016 |
| WO | 2016090472 | A1 | 6/2016 |
| WO | 2017037614 | A1 | 3/2017 |
| WO | 2017077504 | A1 | 5/2017 |
| WO | 2017087330 | A1 | 5/2017 |
| WO | 2017173324 | A2 | 10/2017 |
| WO | 2017217453 | A1 | 12/2017 |
| WO | 2018096017 | A1 | 5/2018 |
| WO | 2018098381 | A1 | 5/2018 |
| WO | 2019055455 | A1 | 3/2019 |
| WO | 2020023411 | A1 | 1/2020 |
| WO | 2020160126 | A1 | 8/2020 |
| WO | 2021026201 | A1 | 2/2021 |
| WO | 2021055395 | A1 | 3/2021 |
| WO | 2021142057 | A1 | 7/2021 |

OTHER PUBLICATIONS

Devos et al., Practical limits of function prediction. Proteins: Structure, Function, and Genetics. 2000, vol. 41: 98-107. (Year: 2000).*

Seffernick et al., Melamine deaminase and Atrazine chlorohydrolase: 98 percent identical but functionally different. J. Bacteriol., 2001, vol. 183 (8): 2405-2410. (Year: 2001).*

Sen et al., Developments in directed evolution for enzyme functions. Appl. Biochem. Biotechnol., 2007, vol. 143: 212-223. (Year: 2007).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Coleine et al., 2017, Genbank No. OQO09719.1.

Grijseels et al., 2017, NCBI Reference Sequence No. XP_022487591.1.

Gusakov et al., 2016, Genbank No. APE61639.1.

Midorikawa et al., 2020, Genbank No. KAF3404744.1.

Voutilainen et al., 2014, Genbank No. AGU68246.1.

Wortman et al., 2022, NCBI Reference Sequence No. XP_658098.1.

Anonymous, 2022, CAZy—Carbohydrate Esterase Family 3.

Bertazzoni et al., 2021, EBI Accession No. Uniprot A0A7U2IB57.

Grigoriev et al., 2018, EBI Accession No. Uniprot A0A2V1D1N3.

Haridas et al., 2023, EBI Accession No. Uniprot A0A9P4JE22.

Haridas et al., 2023, EBI Accession No. Uniprot A0A9P4QS06.

Sun et al., 2022, Industrial Crops & Products, 178, 1-10.

Wang, 2022, EBI Accession No. Uniprot A0A8H6DS96.

Zeiner et al., 2016, EBI Accession No. Uniprot A0A177C2X9.

Zeiner et al., 2016, EBI Accession No. Uniprot A0A177CXR0.

Zeiner et al., 2016, EBI Accession No. Uniprot A0A177CYA9.

Busk, 2013 GenBank Accession No. CDF76456.1.

Eugenio et al., 2021, NCBI Accession No. XP_040733950.1.

Taker et al., 2018, GenBank Accession No. RJE23952.1.

Voutilainen et al., 2014, GenBank Accession No. AGU68248.1.

* cited by examiner

| | | | | | | |
|---|---|---|---|---|---|---|
| GH62 AraF (ug/g-ds) | 0 | 0 | 50 | 0 | 25 | 25 |
| GH10 Xylanase (ug/g-ds) | 0 | 0 | 0 | 50 | 25 | 25 |
| Cellulolytic Composition (ug/g-ds) | 0 | 100 | 100 | 100 | 50 | 100 |
| Glucoamylase Blend A (AGU/g-ds) | 0.42 | 0.42 | 0.42 | 0.42 | 0.42 | 0.42 |

PROCESSES FOR PRODUCING FERMENTATION PRODUCTS USING FIBER-DEGRADING ENZYMES IN FERMENTATION

CROSS-REFERENCE TO RELATED APPLICATIONS

This application is a 35 U.S.C. 371 national application of PCT/CN2022/102201, filed Jun. 29, 2022, which claims priority or the benefit under 35 U.S.C. 119 of Chinese application no. PCT/CN2021/103075 filed Jun. 29, 2021. The contents of these applications are fully incorporated herein by reference.

FIELD OF THE INVENTION

The present invention relates to processes for producing fermentation products from starch-containing material. The invention also relates to an enzyme blend or composition, or a recombinant host cell or fermenting organism suitable for use in a process of the invention.

REFERENCE TO A SEQUENCE LISTING

This application contains a Sequence Listing in computer readable form created on Jun. 27, 2022, named SQ_ST25.xml and 150 KB in size, which is incorporated herein by reference.

BACKGROUND OF THE INVENTION

Production of fermentation products, such as ethanol, from starch-containing material is well-known in the art. Industrially two different kinds of processes are used today. The most commonly used process, often referred to as a "conventional process", and includes liquefying gelatinized starch at high temperature using typically a bacterial alpha-amylase, followed by simultaneous saccharification and fermentation carried out in the presence of a glucoamylase and a fermentation organism. Another well-known process, often referred to as a "raw starch hydrolysis"-process (RSH process), includes simultaneously saccharifying and fermenting granular starch below the initial gelatization temperature typically in the presence of at least a glucoamylase.

Despite significant improvement of fermentation product production processes over the past decade a significant amount of residual starch material is not converted into the desired fermentation product, such as ethanol. At least some of the unconverted residual starch material, e.g., sugars and dextrins, is in the form of non-fermentable Maillard products.

Beta-glucans are polysaccharides that only contain glucose as structural components, and in which the glucose units are linked by beta-glycosidic bonds. Cellulose is one type of beta-glucan in which all of the glucose units are linked by beta-1,4-glucosidic bonds. This feature results in the formation of insoluble cellulose micro-fibrils meaning that microbial hydrolysis of cellulose to glucose requires the use of endo-glucanases (EC 3.2.1.4), cellobiohydrolases (EC 3.2.1.91) and beta-glucosidases (EC 3.2.1.21).

Cellulases are well-known for use in the conversion of lignocellulosic feedstocks into ethanol. Once the lignocellulose is converted to fermentable sugars, e.g., glucose, the fermentable sugars are easily fermented by yeast into ethanol. However, there is still a desire and need for providing processes for producing fermentation products, such as ethanol, from starch-containing material that can provide a higher fermentation product yield, or other advantages, compared to a conventional process.

SUMMARY OF THE INVENTION

Described herein are processes of producing fermentation products, such as ethanol, from starch-containing material using a fermenting organism.

A first aspect relates to a process for producing a fermentation product from starch-containing material, the process comprising the steps of:

i) saccharifying the starch-containing material at a temperature below the initial gelatination temperature; and ii) fermenting the saccharified starch-containing material using a fermenting organism;

wherein at least one polypeptide having cellobiohydrolase activity, endoglucanase activity, or beta-glucosidase activity is present or added during fermentation.

A second aspect relates to a process for producing a fermentation product from starch-containing material comprising the steps of:

i) liquefying the starch-containing material at a temperature above the initial gelatinization temperature using an alpha-amylase;

ii) saccharifying the liquefied starch-containing;

iii) fermenting saccharified starch-containing material using a fermenting organism;

wherein at least one polypeptide having cellobiohydrolase activity, endoglucanase activity, or beta-glucosidase activity is present or added during fermentation.

A third aspect related to isolated polypeptides having cellobiohydrolase activity, endoglucanase activity, or beta-glucosidase activity.

A fourth aspect relates to an enzyme blend or composition comprising at least one polypeptide having cellobiohydrolase activity, endoglucanase activity, or beta-glucosidase activity.

A fifth aspect relates to isolated polynucleotides encoding the polypeptides having cellobiohydrolase activity, endoglucanase activity, or beta-glucosidase activity; nucleic acid constructs and recombinant expression vectors comprising the polynucleotides; recombinant host cells or fermenting organisms comprising the polynucleotides; and methods of producing the polypeptides having cellobiohydrolase activity, endoglucanase activity, or beta-glucosidase activity.

DEFINITIONS

Figure 1:
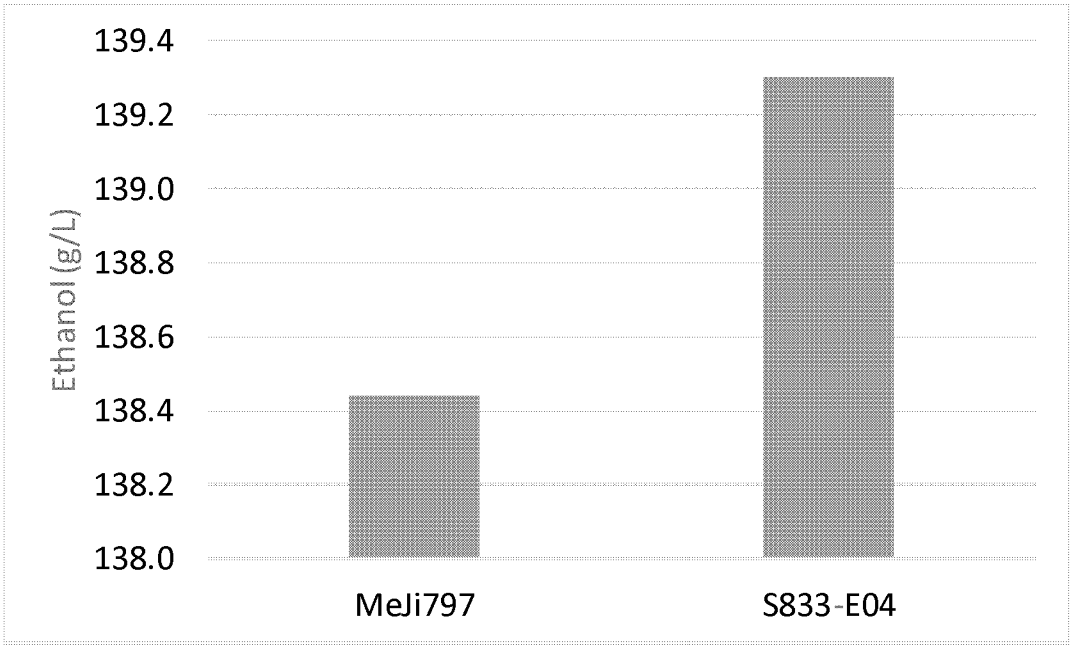
FIG. 1 shows the final ethanol yield following SSF for control strain MeJi797 and yeast strain S833-E04.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-amylase: The term "alpha amylase" means an 1,4-alpha-D-glucan glucanohydrolase, EC. 3.2.1.1, which catalyze hydrolysis of starch and other linear and branched 1,4-glucosidic oligo- and polysaccharides. Alpha-amylase activity can be determined using methods known in the art (e.g., using an alpha amylase assay described WO2020/023411).

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinofuranosidase, alpha-arabinofuranosidase, alpha-L-arabinofuranosidase, alpha-arabinofuranosidase, polysaccharide alpha-L-arabinofuranosidase, alpha-L-arabinofuranoside hydrolase, L-arabinofuranosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 micro for 30 minutes at 40 degrees centigrade followed by arabinose analysis by AMINEX® HPX-87H column chromatography (Bio-Rad Laboratories, Inc., Hercules, CA, USA).

Auxiliary Activity 9: The term "Auxiliary Activity 9" or "AA9" means a polypeptide classified as a lytic polysaccharide monooxygenase (Quinlan et al., 2011, *Proc. Natl. Acad. Sci. USA* 208:15079-15084; Phillips et al., 2011, *ACS Chem. Biol.* 6:1399-1406; Lin et al., 2012, *Structure* 20:1051-1061). AA9 polypeptides were formerly classified into the glycoside hydrolase Family 61 (GH61) according to Henrissat, 1991, *Biochem. J.* 280:309-316, and Henrissat and Bairoch, 1996, *Biochem. J.* 316:695-696.

AA9 polypeptides enhance the hydrolysis of a cellulosic-containing material by an enzyme having cellulolytic activity. Cellulolytic enhancing activity can be determined by measuring the increase in reducing sugars or the increase of the total of cellobiose and glucose from the hydrolysis of a cellulosic-containing material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40 C.-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one embodiment, the beta-glucosidase is an *Aspergillus oryzae* beta-glucosidase (e.g., recombinantly produced in *Aspergillus oryzae* according to WO 02/095014). In another embodiment, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic-containing material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42:55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Catalase: The term "catalase" means hydrogen-peroxide: hydrogen-peroxide oxidoreductase (EC 1.11.1.6) that catalyzes the conversion of 2 $H_2O_2$ to $O_2$+2 $H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Catalytic domain: The term "catalytic domain" means the region of an enzyme containing the catalytic machinery of the enzyme.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15:160-167; Teeri et al., 1998, *Biochem. Soc. Trans.* 26:173-178). Cellobiohydrolase activity can be determined according to the procedures described by Lever et al., 1972, *Anal. Biochem.* 47:273-279; van Tilbeurgh et al., 1982, *FEBS Letters* 149:152-156; van Tilbeurgh and Claeyssens, 1985, *FEBS Letters* 187:283-288; and Tomme et al., 1988, *Eur. J. Biochem.* 170:575-581.

Cellulolytic composition, cellulolytic enzymes or cellulase means a preparation comprising one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24:452-481. Total cellulolytic activity is usually measured using insoluble substrates, including Whatman N°1 filter paper, microcrystalline cellulose, bacterial cellulose, algal cellulose, cotton, pretreated lignocellulose, etc. The most common total cellulolytic activity assay is the filter paper assay using Whatman N°1 filter paper as the substrate. The assay was established by the International Union of Pure and Applied Chemistry (IUPAC) (Ghose, 1987, Measurement of cellulase activities, *Pure Appl. Chem.* 59:257-68).

Cellulolytic enzyme activity is determined by measuring the increase in hydrolysis of a cellulosic material by cellulolytic enzyme(s) under the following conditions: 1-50 mg of cellulolytic enzyme protein/g of cellulose in Pretreated Corn Stover ("PCS") (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, CA, USA).

Coding sequence: The term "coding sequence" or "coding region" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Disruption: The term "disruption" means that a coding region and/or control sequence of a referenced gene is partially or entirely modified (such as by deletion, insertion, and/or substitution of one or more nucleotides) resulting in the absence (inactivation) or decrease in expression, and/or the absence or decrease of enzyme activity of the encoded polypeptide. The effects of disruption can be measured using techniques known in the art such as detecting the absence or decrease of enzyme activity using from cell-free extract measurements referenced herein; or by the absence or decrease of corresponding mRNA (e.g., at least 25% decrease, at least 50% decrease, at least 60% decrease, at least 70% decrease, at least 80% decrease, or at least 90% decrease); the absence or decrease in the amount of corresponding polypeptide having enzyme activity (e.g., at least 25% decrease, at least 50% decrease, at least 60% decrease, at least 70% decrease, at least 80% decrease, or at least 90% decrease); or the absence or decrease of the specific activity of the corresponding polypeptide having enzyme activity (e.g., at least 25% decrease, at least 50% decrease, at least 60% decrease, at least 70% decrease, at least 80% decrease, or at least 90% decrease). Disruptions of a particular gene of interest can be generated by methods known in the art, e.g., by directed homologous recombination (see *Methods in Yeast Genetics* (1997 edition), Adams, Gottschling, Kaiser, and Stems, Cold Spring Harbor Press (1998)).

Endogenous gene: The term "endogenous gene" means a gene that is native to the referenced host cell. "Endogenous gene expression" means expression of an endogenous gene.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24:452-481). Endoglucanase activity can also be determined using carboxymethyl cellulose (CMC) as substrate according to the procedure of Ghose, 1987, *Pure and Appl. Chem.* 59:257-268, at pH 5, 40° C.

Expression: The term "expression" includes any step involved in the production of the polypeptide including, but not limited to, transcription, post-transcriptional modification, translation, post-translational modification, and secretion. Expression can be measured—for example, to detect increased expression—by techniques known in the art, such as measuring levels of mRNA and/or translated polypeptide.

Expression vector: The term "expression vector" means a linear or circular DNA molecule that comprises a polynucleotide encoding a polypeptide and is operably linked to control sequences that provide for its expression.

Fermentable medium: The term "fermentable medium" or "fermentation medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as ethanol. In some instances, the fermentation medium is derived from a natural source, such as sugar cane, starch, or cellulose, and may be the result of pretreating the source by enzymatic hydrolysis (saccharification). The term fermentation medium is understood herein to refer to a medium before the fermenting organism is added, such as, a medium resulting from a saccharification process, as well as a medium used in a simultaneous saccharification and fermentation process (SSF).

Glucoamylase: The term "glucoamylase" (1,4-alpha-D-glucan glucohydrolase, EC 3.2.1.3) is defined as an enzyme that catalyzes the release of D-glucose from the non-reducing ends of starch or related oligo- and polysaccharide molecules. For purposes of the present invention, glucoamylase activity may be determined according to the procedures known in the art, such as those described in WO2020/023411.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6 (3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59:1739-1752, at a suitable temperature such as 40° C.-80° C., e.g., 50° C.; 55° C., 60° C., 65° C., or 70° C., and a suitable pH such as 4-9, e.g., 5.0, 5.5, 6.0, 6.5, or 7.0.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide in a host cell having one or more extra copies of the polynucleotide to quantitatively alter expression. A "heterologous gene" is a gene comprising a heterologous polynucleotide.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, and the like with a nucleic acid construct or expression vector comprising a polynucleotide described herein. The term "host cell" encompasses any progeny of a parent cell that is not identical to the parent cell due to mutations that occur during replication. The term "recombinant cell" is defined herein as a non-naturally occurring host cell comprising one or more (e.g., two, several) heterologous polynucleotides.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" is defined herein as a polypeptide having biological activity that is in its final form following translation and any post-translational modifications, such as N-terminal processing, C-terminal truncation, glycosylation, phosphorylation, etc. The mature polypeptide sequence lacks a signal sequence, which may be determined using techniques known in the art (See, e.g., Zhang and Henzel, 2004, *Protein Science* 13:2819-2824). The term "mature polypeptide coding sequence" means a polynucleotide that encodes a mature polypeptide. In one aspect, the mature polypeptide is amino acids 19 to 520 of SEQ ID NO: 1 based on the SignalP program (Nielsen et al., 1997, *Protein Engineering* 10:1-6) that predicts amino acids 1 to 18 of SEQ ID NO: 1 are a signal peptide. In another aspect, the mature polypeptide is amino acids 1 to 503 of SEQ ID NO: 2 based on the SignalP program that this sequence lacks a signal peptide. In another aspect, the mature polypeptide is amino acids 26 to 533 of SEQ ID NO: 3 based on the SignalP program that predicts amino acids 1 to 25 of SEQ ID NO: 3 are a signal peptide. In another aspect, the mature polypeptide is amino acids 20 to 456 of SEQ ID NO: 4 based on the SignalP program that predicts amino acids 1 to 19 of SEQ ID NO: 4 are a signal peptide. In another aspect, the mature polypeptide is amino acids 20 to 410 of SEQ ID NO: 5 based on the SignalP program that predicts amino acids 1 to 19 of SEQ ID NO: 5 are a signal peptide. In another aspect, the mature polypeptide is amino acids 20 to 855 of SEQ ID NO: 6 based on the SignalP program that predicts amino acids 1 to 19 of SEQ ID NO: 6 are a signal peptide. It is known in the art that a host cell may produce a mixture of two of more different mature polypeptides (i.e., with a different C-terminal and/or N-terminal amino acid) expressed by the same polynucleotide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Nucleic acid construct: The term "nucleic acid construct" means a polynucleotide comprises one or more (e.g., two, several) control sequences. The polynucleotide may be single-stranded or double-stranded, and may be isolated from a naturally occurring gene, modified to contain segments of nucleic acids in a manner that would not otherwise exist in nature, or synthetic.

Operably linked: The term "operably linked" means a configuration in which a control sequence is placed at an appropriate position relative to the coding sequence of a polynucleotide such that the control sequence directs expression of the coding sequence.

Protease: The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-JUBMB, Academic Press, San Diego, California, including supplements 1-5 published in *Eur. J. Biochem.* 223:1-5 (1994); *Eur. J. Biochem.* 232:1-6 (1995); *Eur. J. Biochem.* 237:1-5

(1996); *Eur. J. Biochem.* 250:1-6 (1997); and *Eur. J. Biochem.* 264:610-650 (1999); respectively. The term "subtilases" refer to a sub-group of serine protease according to Siezen et al., 1991, *Protein Engng.* 4:719-737 and Siezen et al., 1997, *Protein Science* 6:501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Protease activity may be determined using methods described in the art (e.g., US 2015/0125925) or using commercially available assay kits (e.g., Sigma-Aldrich).

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to a PHADEBAS assay or the sweet potato starch assay described in WO2016/087237.

Sequence Identity: The relatedness between two amino acid sequences or between two nucleotide sequences is described by the parameter "sequence identity".

For purposes described herein, the degree of sequence identity between two amino acid sequences is determined using the Needleman-Wunsch algorithm (Needleman and Wunsch, *J. Mol. Biol.* 1970, 48, 443-453) as implemented in the Needle program of the EMBOSS package (EMBOSS: The European Molecular Biology Open Software Suite, Rice et al., *Trends Genet* 2000, 16, 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of the Referenced Sequence−Total Number of Gaps in Alignment)

For purposes described herein, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Referenced Sequence−Total Number of Gaps in Alignment)

Signal peptide: The term "signal peptide" is defined herein as a peptide linked (fused) in-frame to the amino terminus of a polypeptide having biological activity and directs the polypeptide into the cell's secretory pathway. Signal sequences may be determined using techniques known in the art (See, e.g., Zhang and Henzel, 2004, *Protein Science* 13:2819-2824). The polypeptides described herein may comprise any suitable signal peptide known in the art, or any signal peptide described in WO2021/025872 (incorporated herein by reference).

Trehalase: The term "trehalase" means an enzyme which degrades trehalose into its unit monosaccharides (i.e., glucose). Trehalases are classified in EC 3.2.1.28 (alpha, alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet. Trehalases are enzymes that catalyze the following reactions:

EC 3.2.1.28: Alpha, alpha-trehalose+$H_2O$⇔2 D-glucose;

EC 3.2.1. 93: Alpha, alpha-trehalose 6-phosphate+$H_2O$ ⇔D-glucose+D-glucose 6-phosphate.

Trehalase activity may be determined according to procedures known in the art.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

DETAILED DESCRIPTION OF THE INVENTION

The present invention relates to processes of producing fermentation products, such as ethanol from starch-containing material using a fermenting organism.

Processes for Producing Fermentation Products from Un-Gelatinized Starch-Containing Material.

Described herein are processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of an alpha-amylase and carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Processes for producing a fermentation product from starch-containing material may comprise simultaneously saccharifying and fermenting starch-containing material using a carbohydrate-source generating enzymes and a fermenting organism at a temperature below the initial gelatinization temperature of said starch-containing material in the presence of an alpha-amylase of the invention. Saccharification and fermentation may also be separate.

One aspect relates to processes for producing fermentation products, such as ethanol, from starch-containing material, the pro comprising the steps of:

i) saccharifying the starch-containing material at a temperature below the initial gelatination temperature; and ii) fermenting the saccharified starch-containing material using a fermenting organism;

wherein at least one polypeptide having cellobiohydrolase activity, endoglucanase activity, or beta-glucosidase activity is present or added during fermentation.

The at least one polypeptide having cellobiohydrolase activity, endoglucanase activity, or beta-glucosidase activity present or added in the above described processes for producing fermentation products from starch-containing material may be added exogenously during saccharification, fermentation or simultaneous saccharification and fermentation as mono-components, as enzyme blends or compositions comprising the polypeptide having cellobiohydrolyase activity, endoglucanase activity, or beta-glucosidase activity, and/or via in-situ expression and secretion of the polypeptide having cellobiohydrolyase activity, endoglucanase activity, or beta-glucosidase activity by the fermenting organism, e.g., a recombinant host cell or fermenting organism described herein (e.g., yeast, such as from the genus *Saccharomyces*, preferably *Saccharomyces cerevisiae*).

Processes for Producing Fermentation Products from Gelatinized Starch-Containing Material Also described are processes for producing fermentation products, such as ethanol, from starch-containing material, which process includes a liquefaction step and sequentially or simultaneously performed saccharification and fermentation steps.

One aspect relates to processes for producing fermentation products from starch-containing material, the process comprising the steps of:

i) liquefying the starch-containing material at a temperature above the initial gelatinization temperature using an alpha-amylase;

ii) saccharifying the liquefied starch-containing;

iii) fermenting saccharified starch-containing material using a fermenting organism;

wherein at least one polypeptide having cellobiohydrolase activity, endoglucanase activity, or beta-glucosidase activity is present or added during fermentation.

The at least one polypeptide having cellobiohydrolase activity, endoglucanase activity, or beta-glucosidase activity present or added in the above described processes for producing fermentation products from starch-containing material may be added exogenously during saccharification, fermentation or simultaneous saccharification and fermentation as mono-components, as enzyme blends or compositions comprising the polypeptide having cellobiohydrolyase activity, endoglucanase activity, or beta-glucosidase activity, and/or via in-situ expression and secretion of the polypeptide having cellobiohydrolyase activity, endoglucanase activity, or beta-glucosidase activity by the fermenting organism, e.g., a recombinant host cell or fermenting organism described herein (e.g., yeast, such as from the genus *Saccharomyces*, preferably *Saccharomyces cerevisiae*).

Steps ii) and iii) may be carried out either sequentially or simultaneously. In a preferred embodiment steps ii) and iii) are carried out simultaneously. The alpha-amylase, an optional thermostable protease, and/or an optional thermostable xylanase, may be added before and/or during liquefaction step i).

A composition of the invention may suitably be used in a process of the invention. A-recombinant host cell or fermenting organism of the invention may suitably be used in a process of the invention. However, the enzymes may also be added separately.

Whether the process includes a liquefaction step or not, the essential feature of the invention is that at least one polypeptide having cellobiohydrolase activity, endoglucanase activity, or beta-glucosidase activity are present or added during fermentation or simultaneous saccharification and fermentation. In one embodiment, at least one polypeptide having cellobiohydrolase activity, endoglucanase activity, or beta-glucosidase activity are present or added during fermentation or simultaneous saccharification and fermentation. In another embodiment, as noted above, the at least one polypeptide having cellobiohydrolase activity, endoglucanase activity, or beta-glucosidase activity may be added exogenously as a standalone enzyme or an enzyme blend or composition comprising at least one, at least two, at least three, at least four, or at least five polypeptides having cellobiohydrolase activity, endoglucanase activity, or beta-glucosidase activity, or expressed and secreted in situ by a recombinant host cell or fermenting organism. In an example embodiment, the at least one polypeptide having cellobiohydrolase activity, endoglucanase activity, or beta-glucosidase activity is added in the form of a cellulolytic composition that comprises the at least one polypeptide and the at least one additional cellulase. In an embodiment, the cellulolytic composition comprises at least two polypeptides having cellobiohydrolase activity, endoglucanase activity, or beta-glucosidase activity. In an embodiment, the cellulolytic composition comprises at least three polypeptides having cellobiohydrolase activity, endoglucanase activity, or beta-glucosidase activity. In an embodiment, the cellulolytic composition comprises a polypeptide having cellobiohydrolase activity, a polypeptide having endoglucanase activity, and a polypeptide having beta-glucosidase activity. Any cellulolytic composition described herein can be present or added during fermentation or simultaneous saccharification and fermentation.

Any cellulase having cellobiohydrolase activity, endoglucanase activity, or beta-glucosidase activity can be present and/or added during saccharification, fermentation, or SSF in a process of the invention (e.g., any mature polypeptide of SEQ ID NO: 1, SEQ ID NO: 2, SEQ ID NO: 3, SEQ ID NO: 4, SEQ ID NO: 5, SEQ ID NO: 6, or variants thereof).

Exemplary cellulases that may be used with the processes described herein and/or expressed by the host cells or fermenting organisms described herein include, but are not limited to the cellulases shown in Table 1 (or derivatives thereof).

TABLE 1

| Donor Organism | Enzyme class | SEQ ID NO. |
|---|---|---|
| *Penicillium emersonii* | Cellobiohydrolase 1 | 1 |
| *Aspergillus nidulans* | Cellobiohydrolase 1 | 2 |

TABLE 1-continued

| Donor Organism | Enzyme class | SEQ ID NO. |
|---|---|---|
| *Penicillium swiecickii* | Cellobiohydrolase 1 | 3 |
| *Talaromyces verruculosus* | Cellobiohydrolase 2 | 4 |
| *Cladosporium antareticum* | Endoglucanase | 5 |
| *Talaromyces pinophilus* | beta-glucosidase | 6 |

The polypeptide having cellobiohydrolase activity, endoglucanase activity, or beta-glucosidase activity may be obtained from microorganisms of any genus. For purposes herein, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one embodiment, the polypeptide having cellobiohydrolase activity is a *Penicillium* cellobiohydrolase I. In another embodiment, the polypeptide having cellobiohydrolase activity is a *Penicillium emersonii* cellobiohydrolase I. In one embodiment, the polypeptide having cellobiohydrolase activity is an *Aspergillus* cellobiohydrolase I. In another embodiment, the polypeptide having cellobiohydrolase activity is an *Aspergillus nidulans* cellobiohydrolase I. In one embodiment, the polypeptide having cellobiohydrolase activity is a *Penicillium* cellobiohydrolase I. In another embodiment, the polypeptide having cellobiohydrolase activity is a *Penicillium swiecickii* cellobiohydrolase 1. In one embodiment, the polypeptide having cellobiohydrolase activity is a *Talaromyces* cellobiohydrolase II. In another embodiment, the polypeptide having cellobiohydrolase activity is a *Talaromyces verruculosus* cellobiohydrolase II. In one embodiment, the polypeptide having endoglucanase activity is a *Cladosporium* endoglucanase. In another embodiment, the polypeptide having endoglucanase activity is a *Cladosporium antareticum* endoglucanase. In one embodiment, the polypeptide having beta-glucosidase activity is a *Talaromyces* beta-glucosidase. In another embodiment, the polypeptide having beta-glucosidase activity is a *Talaromyces pinophilus* beta-glucosidase. It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide having cellobiohydrolase activity, endoglucanase activity, or beta-glucosidase activity coding sequences described or referenced herein, or a subsequence thereof, as well as the transporter described or referenced herein, or a fragment thereof, may be used to design nucleic acid probes to identify and clone DNA encoding a glycerol transporter from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other strains may be screened for DNA that hybridizes with the probes described above and encodes a sugar transporter. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with a coding sequence, or a subsequence thereof, the carrier material is used in a Southern blot.

In one embodiment, the nucleic acid probe is a polynucleotide, or subsequence thereof, that encodes the mature cellobiohydrolase of SEQ ID NO: 1, 2, 3 or 4; the mature endoglucanase of SEQ ID NO: 5, or the mature beta-glucosidase of SEQ ID NO: 6, or a fragment thereof.

For purposes of the probes described above, hybridization indicates that the polynucleotide hybridizes to a labeled nucleic acid probe, or the full-length complementary strand thereof, or a subsequence of the foregoing; under very low to very high stringency conditions. Molecules to which the nucleic acid probe hybridizes under these conditions can be detected using, for example, X-ray film. Stringency and washing conditions are defined as described supra.

In one embodiment, the polypeptide having cellobiohydrolase activity, endoglucanase activity, or beta-glucosidase activity is encoded by a polynucleotide that hybridizes under at least low stringency conditions, e.g., medium stringency conditions, medium-high stringency conditions, high stringency conditions, or very high stringency conditions with the full-length complementary strand of the coding sequence for any one of the glycerol transporters described or referenced herein (e.g., SEQ ID NOs: 312-323). (Sambrook et al., 1989*, Molecular Cloning, A Laboratory Manual,* 2*d edition*, Cold Spring Harbor, New York).

The polypeptide having cellobiohydrolase activity, endoglucanase activity, or beta-glucosidase activity may also be identified and obtained from other sources including microorganisms isolated from nature (e.g., soil, composts, water, silage, etc.) or DNA samples obtained directly from natural materials (e.g., soil, composts, water, silage, etc.) using the above-mentioned probes. Techniques for isolating microorganisms and DNA directly from natural habitats are well known in the art. The polynucleotide encoding a glycerol transporter may then be derived by similarly screening a genomic or cDNA library of another microorganism or mixed DNA sample.

Once a polynucleotide encoding a polypeptide having cellobiohydrolase activity, endoglucanase activity, or beta-glucosidase activity has been detected with a suitable probe as described herein, the sequence may be isolated or cloned by utilizing techniques that are known to those of ordinary skill in the art (See, e.g., Sambrook et al., 1989, supra). Techniques used to isolate or clone polynucleotides encoding polypeptides include isolation from genomic DNA, preparation from cDNA, or a combination thereof. The cloning of the polynucleotides from such genomic DNA can be affected, e.g., by using the well-known polymerase chain reaction (PCR) or antibody screening of expression libraries to detect cloned DNA fragments with shares structural features (See, e.g., Innis et al., 1990, *PCR: A Guide to Methods and Application, Academic Press*, New York). Other nucleic acid amplification procedures such as ligase chain reaction (LCR), ligated activated transcription (LAT) and nucleotide sequence-based amplification (NASBA) may be used.

In one embodiment, the polypeptide having cellobiohydrolase activity comprises or consists of the amino acid sequence of SEQ ID NO: 1, 2, 3, 4, or mature polypeptide thereof. In another embodiment, the polypeptide having cellobiohydrolase is a fragment of the cellobiohydrolase of SEQ ID NO: 1, 2, 3, or 4, or the mature polypeptide thereof, wherein, e.g., the fragment has cellobiohydrolase activity. In one embodiment, the number of amino acid residues in the fragment is at least 75%, e.g., at least 80%, 85%, 90%, or 95% of the number of amino acid residues in referenced full length cellobiohydrolase (e.g. any one of SEQ ID NOs: 1, 2, 3, or 4, or the mature polypeptide thereof). In other embodiments, the polypeptide having cellobiohydrolase activity may comprise the catalytic domain of any cellobiohydrolase described or referenced herein (e.g., the catalytic domain of SEQ ID NO: 1, 2, 3, or 4).

The polypeptide having cellobiohydrolase activity may be a variant of any one of the cellobiohydrolases described supra (e.g., any one of SEQ ID NOs: 1, 2, 3, or 4, or the mature polypeptide thereof). In one embodiment, the polypeptide having cellobiohydrolase activity has at least 60%, e.g., at least 65%, 70%, 75%, 80%, 85%, 90%, 95%, 97%, 98%, 99%, or 100% sequence identity to the amino acid sequence of SEQ ID NO: 1 or the mature polypeptide thereof. In one embodiment, the polypeptide having cellobiohydrolase activity has at least 60%, e.g., at least 65%, 70%, 75%, 80%, 85%, 90%, 95%, 97%, 98%, 99%, or 100% sequence identity to the amino acid sequence of SEQ ID NO: 2, or the mature polypeptide thereof. In one embodiment, the polypeptide having cellobiohydrolase activity has at least 60%, e.g., at least 65%, 70%, 75%, 80%, 85%, 90%, 95%, 97%, 98%, 99%, or 100% sequence identity to the amino acid sequence of SEQ ID NO: 3, or mature polypeptide thereof. In one embodiment, the polypeptide having cellobiohydrolase activity has at least 60%, e.g., at least 65%, 70%, 75%, 80%, 85%, 90%, 95%, 97%, 98%, 99%, or 100% sequence identity to the amino acid sequence of SEQ ID NO: 4, or mature polypeptide thereof.

In one embodiment, the sequence of the polypeptide having cellobiohydrolase activity differs by no more than ten amino acids, e.g., by no more than five amino acids, by no more than four amino acids, by no more than three amino acids, by no more than two amino acids, or by one amino acid from the amino acid sequence of any one of the cellobiohydrolases described supra (e.g., any one of SEQ ID NOs: 1, 2, 3, or 4, or mature polypeptide thereof). In one embodiment, the polypeptide having cellobiohydrolase activity has an amino acid substitution, deletion, and/or insertion of one or more (e.g., two, several) of the amino acid sequence of any one of the cellobiohydrolases described supra (e.g., any one of SEQ ID NOs: 1, 2, 3, or 4, or mature polypeptide thereof). In some embodiments, the total number of amino acid substitutions, deletions and/or insertions is not more than 10, e.g., not more than 9, 8, 7, 6, 5, 4, 3, 2, or 1.

In one embodiment, the polypeptide having endoglucanase activity comprises or consists of the amino acid sequence of SEQ ID NO: 5, or mature polypeptide thereof. In another embodiment, the polypeptide having endoglucanase is a fragment of the endoglucanase of SEQ ID NO: 5, or mature polypeptide thereof, wherein, e.g., the fragment has endoglucanase activity. In one embodiment, the number of amino acid residues in the fragment is at least 75%, e.g., at least 80%, 85%, 90%, or 95% of the number of amino acid residues in referenced full length endoglucanase (e.g. of SEQ ID NO: 5, or mature polypeptide thereof). In other embodiments, the polypeptide having endoglucanase activity may comprise the catalytic domain of any endoglucanase described or referenced herein (e.g., the catalytic domain of SEQ ID NO: 5).

The polypeptide having endoglucanase activity may be a variant of the endoglucanase of SEQ ID NO: 5. In one embodiment, the polypeptide having endoglucanase activity has at least 60%, e.g., at least 65%, 70%, 75%, 80%, 85%, 90%, 95%, 97%, 98%, 99%, or 100% sequence identity to the amino acid sequence of SEQ ID NO: 5, or mature polypeptide thereof.

In one embodiment, the sequence of the polypeptide having endoglucanase activity differs by no more than ten amino acids, e.g., by no more than five amino acids, by no more than four amino acids, by no more than three amino acids, by no more than two amino acids, or by one amino acid from the amino acid sequence SEQ ID NO: 5, or mature polypeptide thereof. In one embodiment, the polypeptide having endoglucanase activity has an amino acid substitution, deletion, and/or insertion of one or more (e.g., two, several) of the amino acid sequence of SEQ ID NO: 5, or mature polypeptide thereof. In some embodiments, the total number of amino acid substitutions, deletions and/or insertions is not more than 10, e.g., not more than 9, 8, 7, 6, 5, 4, 3, 2, or 1.

In one embodiment, the polypeptide having beta-glucosidase activity comprises or consists of the amino acid sequence of SEQ ID NO: 6, or mature polypeptide thereof. In another embodiment, the polypeptide having beta-glucosidase is a fragment of the beta-glucosidase of SEQ ID NO: 6, or mature polypeptide thereof, wherein, e.g., the fragment has beta-glucosidase activity. In one embodiment, the number of amino acid residues in the fragment is at least 75%, e.g., at least 80%, 85%, 90%, or 95% of the number of amino acid residues in referenced full length endoglucanase (e.g. of SEQ ID NO: 6, or mature polypeptide thereof). In other embodiments, the polypeptide having beta-glucosidase activity may comprise the catalytic domain of any beta-glucosidase described or referenced herein (e.g., the catalytic domain of SEQ ID NO: 6, or mature polypeptide thereof).

The polypeptide having beta-glucosidase activity may be a variant of the beta-glucosidase of SEQ ID NO: 6. In one embodiment, the polypeptide having beta-glucosidase activity has at least 60%, e.g., at least 65%, 70%, 75%, 80%, 85%, 90%, 95%, 97%, 98%, 99%, or 100% sequence identity to the amino acid sequence of SEQ ID NO: 6, or mature polypeptide thereof.

In one embodiment, the sequence of the polypeptide having beta-glucosidase activity differs by no more than ten amino acids, e.g., by no more than five amino acids, by no more than four amino acids, by no more than three amino acids, by no more than two amino acids, or by one amino acid from the amino acid sequence SEQ ID NO: 6, or mature polypeptide thereof. In one embodiment, the polypeptide having beta-glucosidase activity has an amino acid substitution, deletion, and/or insertion of one or more (e.g., two, several) of the amino acid sequence of SEQ ID NO: 6, or mature polypeptide thereof. In some embodiments, the total number of amino acid substitutions, deletions and/or insertions is not more than 10, e.g., not more than 9, 8, 7, 6, 5, 4, 3, 2, or 1.

The amino acid changes are generally of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the glycerol transporters, alter the substrate specificity, change the pH optimum, and the like.

Essential amino acids can be identified according to procedures known in the art, such as site-directed mutagenesis or alanine-scanning mutagenesis (Cunningham and Wells, 1989, *Science* 244:1081-1085). In the latter technique, single alanine mutations are introduced at every residue in the molecule, and the resultant mutant molecules are tested for activity to identify amino acid residues that are critical to the activity of the molecule. See also, Hilton et al., 1996, *J. Biol. Chem.* 271:4699-4708. The active site or other biological interaction can also be determined by physical analysis of structure, as determined by such techniques as nuclear magnetic resonance, crystallography, electron diffraction, or photoaffinity labeling, in conjunction with mutation of putative contact site amino acids (See, for example, de Vos et al., 1992, *Science* 255:306-312; Smith et al., 1992, *J. Mol. Biol.* 224:899-904; Wlodaver et al., 1992, *FEBS Lett.* 309:59-64). The identities of essential amino acids can also be inferred from analysis of identities with other cellulases that are related to the referenced glycerol transporter.

Additional guidance on the structure-activity relationship of the cellulases herein can be determined using multiple sequence alignment (MSA) techniques well-known in the art. Based on the teachings herein, the skilled artisan could make similar alignments with any number of cellulases described herein or known in the art. Such alignments aid the skilled artisan to determine potentially relevant domains (e.g., binding domains or catalytic domains), as well as which amino acid residues are conserved and not conserved among the different cellulase sequences. It is appreciated in the art that changing an amino acid that is conserved at a particular position between disclosed polypeptides will more likely result in a change in biological activity (Bowie et al., 1990, *Science* 247:1306-1310: "Residues that are directly involved in protein functions such as binding or catalysis will certainly be among the most conserved"). In contrast, substituting an amino acid that is not highly conserved among the polypeptides will not likely or significantly alter the biological activity.

Even further guidance on the structure-activity relationship for the skilled artisan can be found in published x-ray crystallography studies known in the art.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241:53-57; Bowie and Sauer, 1989, *Proc. Natl. Acad. Sci. USA* 86:2152-2156; WO95/17413; or WO95/22625. Other methods that can be used include error-prone PCR, phage display (e.g., Lowman et al., 1991, *Biochemistry* 30:10832-10837; U.S. Pat. No. 5,223,409; WO92/06204), and region-directed mutagenesis (Derbyshire et al., 1986, *Gene* 46:145; Ner et al., 1988, DNA 7:127).

Mutagenesis/shuffling methods can be combined with high-throughput, automated screening methods to detect activity of cloned, mutagenized polypeptides expressed by host cells (Ness et al., 1999, *Nature Biotechnology* 17:893-896). Mutagenized DNA molecules that encode active glycerol transporters can be recovered from the host cells and rapidly sequenced using standard methods in the art. These methods allow the rapid determination of the importance of individual amino acid residues in a polypeptide.

In one embodiment, the heterologous polynucleotide encoding the polypeptide having cellobiohydrolase activity comprises or consists of a coding sequence of any one of the cellobiohydrolases described supra (e.g., any one of SEQ ID NOs: 1, 2, 3, or 4, or mature polypeptide thereof). In another embodiment, the heterologous polynucleotide encoding the polypeptide having cellobiohydrolase activity comprises a subsequence of a coding sequence of any one of the cellobiohydrolases described supra (e.g., any one of SEQ ID NOs: 1, 2, 3, or 4, or mature polypeptide thereof) wherein the subsequence encodes a polypeptide having cellobiohydrolase activity. In another embodiment, the number of nucleotides residues in the coding subsequence is at least 75%, e.g., at least 80%, 85%, 90%, or 95% of the number of the referenced coding sequence.

In another embodiment, the heterologous polynucleotide encoding the polypeptide having cellobiohydrolase activity comprises a coding sequence having at least 60%, e.g., at least 65%, at least 70%, at least 75%, at least 80%, at least 85%, at least 90%, at least 95%, at least 96%, at least 97%, at least 98%, at least 99%, or 100% sequence identity to a coding sequence of any one of the cellobiohydrolases described supra (e.g., any one of SEQ ID NOs: '1, 2, 3, or 4, or mature polypeptide thereof).

In one embodiment, the heterologous polynucleotide encoding the polypeptide having endoglucanase activity comprises or consists of the coding sequence of the endoglucanase of SEQ ID NO: 5. In another embodiment, the heterologous polynucleotide encoding the polypeptide having endoglucanase activity comprises a subsequence of a coding sequence of the endoglucanase of SEQ ID NO: 5 wherein the subsequence encodes a polypeptide having endoglucanase activity. In another embodiment, the number of nucleotides residues in the coding subsequence is at least 75%, e.g., at least 80%, 85%, 90%, or 95% of the number of the referenced coding sequence.

In another embodiment, the heterologous polynucleotide encoding the polypeptide having endoglucanase activity comprises a coding sequence having at least 60%, e.g., at least 65%, at least 70%, at least 75%, at least 80%, at least 85%, at least 90%, at least 95%, at least 96%, at least 97%, at least 98%, at least 99%, or 100% sequence identity to a coding sequence of the endoglucanase of SEQ ID NO: 5, or mature polypeptide thereof.

In one embodiment, the heterologous polynucleotide encoding the polypeptide having beta-glucosidase activity comprises or consists of a coding sequence of the beta-glucosidase of SEQ ID NO: 6, or mature polypeptide thereof. In another embodiment, the heterologous polynucleotide encoding the polypeptide having beta-glucosidase activity comprises a subsequence of a coding sequence of the beta-glucosidase of SEQ ID NO: 6, or mature polypeptide thereof wherein the subsequence encodes a polypeptide having beta-glucosidase activity. In another embodiment, the number of nucleotides residues in the coding subsequence is at least 75%, e.g., at least 80%, 85%, 90%, or 95% of the number of the referenced coding sequence.

In another embodiment, the heterologous polynucleotide encoding the polypeptide having beta-glucosidase activity comprises a coding sequence having at least 60%, e.g., at least 65%, at least 70%, at least 75%, at least 80%, at least 85%, at least 90%, at least 95%, at least 96%, at least 97%, at least 98%, at least 99%, or 100% sequence identity to a coding sequence of the beta-glucosidase of SEQ ID NO: 6, or mature polypeptide thereof.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae* or any other host used for production). Codon-optimization for expression in yeast cells is known in the art (e.g., U.S. Pat. No. 8,326,547).

The polypeptide having cellobiohydrolase activity, endoglucanase activity, or beta-glucosidase activity may be a fused polypeptide or cleavable fusion polypeptide in which another polypeptide is fused at the N-terminus or the C-terminus of the glycerol transporter. A fused polypeptide may be produced by fusing a polynucleotide encoding another polypeptide to a polynucleotide encoding the glycerol transporter. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12:2575-2583; Dawson et al., 1994, *Science* 266:776-779).

In some embodiments, the polypeptide having cellobiohydrolase activity, endoglucanase activity, or beta-glucosidase activity is a fusion protein comprising a signal peptide linked to the N-terminus of a mature polypeptide, such as any signal sequences described in WO2021/025872 "Fusion Proteins For Improved Enzyme Expression" (the content of which is hereby incorporated by reference).

In terms of dose ranges envisaged, in one embodiment, the polypeptide having cellobiohydrolase activity, endoglucanase activity, and/or beta-glucosidase activity are dosed in the range 0.1-1000 micro gram EP/g DS; 0.5-500 micro gram EP/g DS; 1-100 micro gram EP/g DS; such as 5-50 micro gram EP/g DS.

As described supra, the polypeptides having cellobiohydrolase activity, endoglucanase activity, or beta-glucosidase activity are present or added during fermentation or simultaneous saccharification and fermentation, however, preferred embodiments may also include the addition of other enzyme classes during fermentation/SSF. Examples of other enzymes that can be added during fermentation/SSF include, without limitation, alpha-amylases, glucoamylases, trehalases, cellulases/cellulolytic compositions, and hemicellulases/hemicellulolytic compositions. Particularly, saccharification and/or fermentation or simultaneous saccharification and fermentation, is performed in the presence of at least one cellulase/cellulolytic composition. More particularly the cellulases/cellulolytic composition are derived from a strain of *Trichoderma*, in particular *Trichoderma reesei*, or a strain of *Humicola*, in particular *Humicola insolens*, or a strain of *Chrysosporium*, in particular *Chrysosporium lucknowense*. The cellulases/cellulolytic composition should at least comprise a beta-glucosidase, a cellobiohydrolase and an endoglucanase. In one embodiment, the cellulases/cellulolytic composition comprises one or more polypeptides selected from the group consisting of:

GH61 polypeptide having cellulolytic enhancing activity,
beta-glucosidase;
Cellobiohydrolase I;
Cellobiohydrolase II;
or a mixture of two, three, or four thereof.

Cellulases are well known in the art, and many are derived from filamentous fungi. Particularly, according to the invention, the cellulases/cellulolytic composition comprises one or more of the following components:

(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

More specifically the cellulases/cellulolytic composition is in one embodiment a *Trichoderma reesei* cellulolytic enzyme composition further comprising *Penicillium emersonii* GH61A polypeptide having cellulolytic enhancing activity disclosed in SEQ ID NO: 7, or polypeptide having at least 90% identity, at least 95% identity, at least 96% identity, at least 97% identity, at least 99% identity to SEQ ID NO: 7 and an *Aspergillus fumigatus* beta-glucosidase disclosed in SEQ ID NO: 8 or a variant thereof with the following substitutions: F100D, S283G, N456E, F512Y having at least 90% identity, at least 95% identity, at least 96% identity, at least 97% identity, at least 99% identity to SEQ ID NO: 8.

In one embodiment, the cellulolytic composition comprises a cellobiohydrolase I (CBH I), such as one derived from a strain of the genus *Aspergillus*, such as a strain of *Aspergillus fumigatus*, such as the CBHI disclosed as SEQ ID NO: 9, or CBH I having at least 90% identity, at least 95% identity, at least 96% identity, at least 97% identity, at least 99% identity to SEQ ID NO: 9.

In one embodiment, the cellulolytic composition comprises a cellobiohydrolase II (CBH II), such as one derived from a strain of the genus *Aspergillus*, such as a strain of *Aspergillus fumigatus*; such as the CBH II disclosed as SEQ ID NO: 10, or a CBH II having at least 90% identity, at least 95% identity, at least 96% identity, at least 97% identity, at least 99% identity to SEQ ID NO: 10.

Examples of suitable cellulases can be found in "Cellulolytic Composition present and/or added during Saccharification and/or Fermentation".

Saccharification and/or fermentation or simultaneous saccharification and fermentation can be performed in the presence of at least one hemicellulolytic composition. In an embodiment, the hemicellulolytic composition present or added during saccharification and/or fermentation or simultaneous saccharification and fermentation comprises: (i) a GH10 xylanase; and (ii) a GH62 arabinofuranosidase.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of beta-glucosidase, cellobiohydrolase, and endoglucanase; and wherein the hemicellulolytic composition comprises an arabinofuranosidase and a xylanase.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises an arabinofuranosidase and a xylanase.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises a GH62 arabinofuranosidase and a GH10 xylanase.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises a *Talaromyces* GH62 arabinofuranosidase and a *Talaromyces* GH10 xylanase.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises a *Talaromyces pinophilus* GH62 arabinofuranosidase and a *Talaromyces* leycettanus GH10 xylanase.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises: (i) a GH10 xylanase, such as one derived from a strain of the genus *Talaromyces*, such as a strain of *Talaromyces* leycettanus, such as the one disclosed as SEQ ID NO: 59, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 59; and (ii) a GH62 arabinofuranosidase, such as one derived from a strain of the genus *Talaromyces*, such as a strain of *Talaromyces pinophilus*, such as the one disclosed as SEQ ID NO: 60, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 60.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of an *Aspergillus* beta-glucosidase or a variant thereof; an *Aspergillus* cellobiohydrolase 1; and a *Trichoderma* endoglucanase I; and wherein the hemicellulolytic composition comprises an arabinofuranosidase and a xylanase.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of an *Aspergillus* beta-glucosidase or a variant thereof; an *Aspergillus* cellobiohydrolase I; and a *Trichoderma* endoglucanase I; and wherein the hemicellulolytic composition comprises an arabinofuranosidase and a xylanase, wherein the cellulolytic composition is derived from a strain of *Trichoderma*, such as *Trichoderma reesei*, or a strain of *Humicola*, such as *Humicola insolens*, or a strain of *Chrysosporium*, such as *Chrysosporium lucknowense*.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises an arabinofuranosidase and a xylanase.

In an example preferred embodiment, saccharification and/or fermentation or simultaneous saccharification and fermentation is performed in the presence of a cellulolytic composition and a hemicellulolytic composition, wherein the cellulolytic composition comprises two or three polypeptides selected from the group consisting of an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises an arabinofuranosidase and a xylanase, wherein the cellulolytic composition is derived from a strain of *Trichoderma*, such as *Trichoderma reesei*, or a strain of *Humicola*, such as *Humicola insolens*, or a strain of *Chrysosporium*, such as *Chrysosporium lucknowense*.

In an example preferred embodiment, saccharification and/or fermentation or simultaneous saccharification and fermentation is performed in the presence of a cellulolytic composition and a hemicellulolytic composition, wherein the cellulolytic composition comprises:

(i) an *Aspergillus fumigatus* beta-glucosidase disclosed in SEQ ID NO: 8 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 8;

(ii) a cellobiohydrolase I (CBH I), such as one derived from a strain of the genus *Aspergillus*, such as a strain of *Aspergillus fumigatus*, such as the CBHI disclosed as SEQ ID NO: 9, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 9; and (iii) an endoglucanase I (EGI), such as one derived from a strain of the genus *Trichoderma*, such as a strain of *Trichoderma reesei*, such as the EGI disclosed as SEQ ID NO: 29, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92%-identity, at least 93% identity, at least 94% identity, at least 95% identity, at least 96% identity, at least 97% identity, at least 98% identity, or at least 99% identity to SEQ ID NO: 29; and wherein the hemicellulolytic composition comprises an arabinofuranosidase and a xylanase.

In an example preferred embodiment, saccharification and/or fermentation or simultaneous saccharification and fermentation is performed in the presence of a cellulolytic composition and a hemicellulolytic composition, wherein the cellulolytic composition comprises an *Aspergillus* beta-glucosidase or a variant thereof; an *Aspergillus* cellobiohydrolase I; and a *Trichoderma* endoglucanase I; and wherein the hemicellulolytic composition comprises an GH10 arabinofuranosidase and a GH10 xylanase.

In an example preferred embodiment, saccharification and/or fermentation or simultaneous saccharification and fermentation is performed in the presence of a cellulolytic composition and a hemicellulolytic composition, wherein the cellulolytic composition comprises an *Aspergillus* beta-glucosidase or a variant thereof; an *Aspergillus* cellobiohydrolase I; and a *Trichoderma* endoglucanase I; and wherein the hemicellulolytic composition comprises a *Talaromyces* GH10 arabinofuranosidase and a *Talaromyces* GH10 xylanase.

In an example preferred embodiment, saccharification and/or fermentation or simultaneous saccharification and fermentation is performed in the presence of a cellulolytic composition and a hemicellulolytic composition, wherein the cellulolytic composition comprises an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises an GH10 arabinofuranosidase and a GH10 xylanase.

In an example preferred embodiment, saccharification and/or fermentation or simultaneous saccharification and fermentation is performed in the presence of a cellulolytic composition and a hemicellulolytic composition, wherein the cellulolytic composition comprises an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises a *Talaromyces pinophilus* GH10 arabinofuranosidase and a *Talaromyces* leycettanus GH10 xylanase.

In an example preferred embodiment, saccharification and/or fermentation or simultaneous saccharification and fermentation is performed in the presence of a *Trichoderma* cellulolytic composition and a hemicellulolytic composition, wherein the cellulolytic composition comprises an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises a *Talaromyces pinophilus* GH10 arabinofuranosidase and a *Talaromyces* leycettanus GH10 xylanase.

In an example preferred embodiment, saccharification and/or fermentation or simultaneous saccharification and fermentation is performed in the presence of a *Trichoderma reesei* cellulolytic composition and a hemicellulolytic composition, wherein the cellulolytic composition comprises an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises a *Talaromyces pinophilus* GH10 arabinofuranosidase and a *Talaromyces* leycettanus GH10 xylanase.

In an example preferred embodiment, saccharification and/or fermentation or simultaneous saccharification and fermentation is performed in the presence of a *Trichoderma reesei* cellulolytic composition and a hemicellulolytic composition, wherein the cellulolytic composition comprises:

(i) an *Aspergillus fumigatus* beta-glucosidase disclosed in SEQ ID NO: 8 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 8;

(ii) a cellobiohydrolase I (CBH I), such as one derived from a strain of the genus *Aspergillus*, such as a strain of *Aspergillus fumigatus*, such as the CBHI disclosed as SEQ ID NO: 9, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 9; and (iii) an endoglucanase I (EGI), such as one derived from a strain of the genus *Trichoderma*, such as a strain of *Trichoderma reesei*, such as the EGI disclosed as SEQ ID NO: 29, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 29; and wherein the hemicellulolytic composition comprises:

(i) a GH10 xylanase, such as one derived from a strain of the genus *Talaromyces*, such as a strain of *Talaromyces* leycettanus, such as the one disclosed as SEQ ID NO: 59, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 59; and (ii) a GH62 arabinofuranosidase, such as one derived from a strain of the genus *Talaromyces*, such as a strain of *Talaromyces pinophilus*, such as the one disclosed as SEQ ID NO: 60, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 60.

Examples of alpha-amylases can be found in the "Alpha-Amylase Present and/or Added During Liquefaction"-section below. Examples of thermostable proteases can be found in the "Protease Present and/or Added During Liquefaction"-section below. Examples of suitable optional carbohydrate-source generating enzymes, preferably thermostable carbohydrate-source generating enzymes, in particular, a thermostable glucoamylase, can be found in the "Carbohydrate-Source Generating Enzymes Present and/or Added During Liquefaction"-section below.

The pH during liquefaction may be between 4-7. In an embodiment the pH during liquefaction is from 4.5-5.0, such as between 4.5-4.8. In another embodiment liquefaction is carried out at a pH above 5.0-6.5, such as above 5.0-6.0, such as above 5.0-5.5, such as between 5.2-6.2, such as around 5.2, such as around 5.4, such as around 5.6, such as around 5.8.

The process temperature during liquefaction is above the initial gelatinization temperature. The term "initial gelatinization temperature" refers to the lowest temperature at which solubilization of starch, typically by heating, begins. The temperature can vary for different starches.

In one embodiment the temperature during liquefaction step i) is in the range from 70-100° C., such as between 75-95° C., such as between 75-90° C., preferably between 80-90° C., such as between 82-88° C., such as around 85° C.

In one embodiment, the process of the invention further comprises, prior to the step i), the steps of:

a) reducing the particle size of the starch-containing material, preferably by dry milling;
b) forming a slurry comprising the starch-containing material and water.

The starch-containing starting material, such as whole grains, may be reduced in particle size, e.g., by milling, in order to open up the structure, to increase surface area, and allowing for further processing. Generally, there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry and wet milling are well known in the art of starch processing. According to the present invention dry milling is preferred. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

The aqueous slurry may contain from 10-55 w/w-% dry solids (DS), preferably 25-45 w/w-% dry solids (DS), more preferably 30-40 w/w-% dry solids (DS) of starch-containing material.

The slurry may be heated to above the initial gelatinization temperature, preferably to between 80-90° C., between pH 4-7, preferably between 4.5-5.0 or 5.0 and 6.0, for 30 minutes to 5 hours, such as around 2 hours.

The alpha-amylase, optional thermostable protease, optional carbohydrate-source generating enzyme, in particular thermostable glucoamylase, may initially be added to the aqueous slurry to initiate liquefaction (thinning). In an embodiment only a portion of the enzymes is added to the aqueous slurry, while the rest of the enzymes are added during liquefaction step i).

Liquefaction step i) is according to the invention carried out for 0.5-5 hours, such as 1-3 hours, such as typically around 2 hours.

The aqueous slurry may in an embodiment be jet-cooked to further gelatinize the slurry before being subjected to liquefaction in step i). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

Saccharification and Fermentation

One or more carbohydrate-source generating enzymes, in particular glucoamylase, may be present and/or added during saccharification step ii) and/or fermentation step iii). The carbohydrate-source generating enzyme may preferably be a glucoamylase, but may also be an enzyme selected from the group consisting of: beta-amylase, maltogenic amylase and alpha-glucosidase. The carbohydrate-source generating enzyme added during saccharification step ii) and/or fermentation step iii) is typically different from the optional carbohydrate-source generating enzyme, in particular thermostable glucoamylase, optionally added during liquefaction step i). In a preferred embodiment the carbohydrate-source generating enzymes, in particular glucoamylase, is added together with a fungal alpha-amylase.

Examples of carbohydrate-source generating enzymes, including glucoamylases, can be found in the "Carbohydrate-Source Generating Enzyme Present and/or Added During Saccharification and/or Fermentation"-section below.

One or more alpha-amylases may be present and/or added during saccharification step ii) and/or fermentation step iii). In an embodiment, the alpha-amylase is the *Rhizomucor pusillus* alpha-amylase with *Aspergillus niger* glucoamylase linker and SBD disclosed as SEQ ID NO: 11 with the following substitutions: G128D+D143N (activity ratio AGU:AGU:FAU(F): approx. 30:7:1).

One or more trehalases may be present and/or added during saccharification step ii) and/or fermentation step iii). In an embodiment, the trehalase is the *Talaromyces funiculosus* trehalase disclosed herein as SEQ ID NO: 12, or one having at least 60%, at least 65%, at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 12.

In an embodiment, the trehalase is the *Myceliophthora sepedonium* trehalase disclosed herein as SEQ ID NO: 28, or one having at least 60%, at least 65%, at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 28.

In an embodiment, the trehalase is part of a blend comprising *Gloeophyllum sepiarium* glucoamylase disclosed in SEQ ID NO: 13 or one having at least 60%, at least 65%, at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 13, *Talaromyces funiculosus* trehalase disclosed herein as SEQ ID NO: 12, or one having at least 60%, at least 65%, at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 12, and *Rhizomucor pusillus* alpha-amylase with *Aspergillus niger* glucoamylase linker and SBD disclosed as SEQ ID NO: 11 with the following substitutions: G128D+D143N (activity ratio AGU:AGU:FAU(F): approx. 30:7:1) or one having at least 60%, at least 65%, at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 11.

When doing sequential saccharification and fermentation, saccharification step ii) may be carried out at conditions well-known in the art. For instance, the saccharification step ii) may last up to from about 24 to about 72 hours. In an embodiment pre-saccharification is done. Pre-saccharification is typically done for 40-90 minutes at a temperature between 30-65° C., typically about 60° C. Pre-saccharification is in an embodiment followed by saccharification during fermentation in simultaneous saccharification and fermentation ("SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step ii) and the fermentation step iii) are carried out simultaneously. There is no holding stage for the saccharification, meaning that a fermenting organism, such as yeast, and enzyme(s), may be added together. However, it is also contemplated to add the fermenting organism and enzyme(s) separately. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 3.5-5, in particular between 3.8 and 4.3.

Fermentation Medium

"Fermentation media" or "fermentation medium" refers to the environment in which fermentation is carried out. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "Fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae.*

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5\times10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC-North American Bioproducts Corporation, GA, USA), GERT STRAND (available from Gert Strand AB, Sweden), and FERMIOL (available from DSM Specialties). Other useful yeast strains are available from biological depositories such as the American Type Culture Collection (ATCC) or the Deutsche Sammlung von Mikroorganismen und Zellkulturen GmbH (DSMZ), such as, e.g., BY4741 (e.g., ATCC 201388); Y108-1 (ATCC PTA.10567) and NRRL YB-1952 (ARS Culture Collection). Still other *S. cerevisiae* strains suitable as host cells DBY746, [Alpha][Eta]22, S150-2B, GPY55-15Ba, CEN.PK, USM21, TMB3500, TMB3400, VTT-A-63015, VTT-A-85068, VTT-c-79093 and their derivatives as well as *Saccharomyces* sp. 1400, 424A (LNH-ST), 259A (LNH-ST) and derivatives thereof.

As used herein, a "derivative" of strain is derived from a referenced strain, such as through mutagenesis, recombinant DNA technology, mating, cell fusion, or cytoduction between yeast strains. Those skilled in the art will understand that the genetic alterations, including metabolic modifications exemplified herein, may be described with reference to a suitable host organism and their corresponding metabolic reactions or a suitable source organism for desired genetic material such as genes for a desired metabolic pathway. However, given the complete genome sequencing of a wide variety of organisms and the high level of skill in the area of genomics, those skilled in the art can apply the teachings and guidance provided herein to other organisms. For example, the metabolic alterations exemplified herein can readily be applied to other species by incorporating the same or analogous encoding nucleic acid from species other than the referenced species.

The host cell or fermenting organism may be *Saccharomyces* strain, e.g., *Saccharomyces cerevisiae* strain produced using the method described and concerned in U.S. Pat. No. 8,257,959-BB. In one embodiment, the recombinant cell is a derivative of a strain *Saccharomyces cerevisiae* CIBTS1260 (deposited under Accession No. NRRL Y-50973 at the *Agricultural Research* Service Culture Collection (NRRL), Illinois 61604 U.S.A.).

The strain may also be a derivative of *Saccharomyces cerevisiae* strain NMI V14/004037 (See, WO2015/143324 and WO2015/143317 each incorporated herein by reference), strain nos. V15/004035, V15/004036, and V15/004037 (See, WO 2016/153924 incorporated herein by reference), strain nos. V15/001459, V15/001460, V15/001461 (See, WO2016/138437 incorporated herein by reference), strain no. NRRL Y67342 (See, WO2018/098381 incorporated herein by reference), strain nos. NRRL Y67549 and NRRL Y67700 (See, PCT/US2019/018249 incorporated herein by reference), or any strain described in WO2017/087330 (incorporated herein by reference).

The fermenting organisms may be a host cell that expresses a heterologous polypeptide having cellobiohydrolase, endoglucanase, or beta-glucosidase activity (e.g., any polypeptide having cellobiohydrolase, endoglucanase, or beta-glucosidase activity described herein, such as the cellobiohydrolase of SEQ ID NO: 1, 2, 4 or 4; the endoglucanase of SEQ ID NO: 5, or the beta-glucosidase of SEQ ID NO: 6, or a derivative thereof). Any polypeptide having cellobiohydrolase, endoglucanase, or beta-glucosidase activity contemplated for a process, enzyme blend, or composition described herein is also contemplated for expression by a fermenting organism or host cell.

In one embodiment is a recombinant host cell comprising a heterologous polynucleotide encoding a polypeptide having cellobiohydrolase, endoglucanase, or beta-glucosidase (e.g., any polypeptide having cellobiohydrolase, endoglucanase, or beta-glucosidase activity described herein, such as the cellobiohydrolase of SEQ ID NO: 1, 2, 4 or 4; the endoglucanase of SEQ ID NO: 5, or the beta-glucosidase of SEQ ID NO: 6, or a derivative thereof).

In some embodiments, the host cells and/or fermenting organisms comprise one or more heterologous polynucleotides encoding an alpha-amylase, glucoamylase, protease and/or cellulase. Examples of alpha-amylase, glucoamylase, protease and cellulases suitable for expression in the host cells and/or fermenting organisms are described in more detail herein.

The host cells and fermenting organisms described herein may utilize expression vectors comprising the coding sequence of one or more (e.g., two, several) heterologous genes linked to one or more control sequences that direct expression in a suitable cell under conditions compatible with the control sequence(s). Such expression vectors may be used in any of the cells and methods described herein. The polynucleotides described herein may be manipulated in a variety of ways to provide for expression of a desired polypeptide. Manipulation of the polynucleotide prior to its insertion into a vector may be desirable or necessary depending on the expression vector. The techniques for modifying polynucleotides utilizing recombinant DNA methods are well known in the art.

A construct or vector (or multiple constructs or vectors) comprising the one or more (e.g., two, several) heterologous genes may be introduced into a cell so that the construct or vector is maintained as a chromosomal integrant or as a self-replicating extra-chromosomal vector as described earlier.

The various nucleotide and control sequences may be joined together to produce a recombinant expression vector that may include one or more (e.g., two, several) convenient restriction sites to allow for insertion or substitution of the polynucleotide at such sites. Alternatively, the polynucleotide(s) may be expressed by inserting the polynucleotide(s) or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the cell, or a transposon, may be used.

The expression vector may contain any suitable promoter sequence that is recognized by a cell for expression of a gene described herein. The promoter sequence contains transcriptional control sequences that mediate the expression of the polypeptide. The promoter may be any polynucleotide that shows transcriptional activity in the cell of choice including mutant, truncated, and hybrid promoters, and may be obtained from genes encoding extracellular or intracellular polypeptides either homologous or heterologous to the cell.

Each heterologous polynucleotide described herein may be operably linked to a promoter that is foreign to the polynucleotide. For example, in one embodiment, the nucleic acid construct encoding the fusion protein is operably linked to a promoter foreign to the polynucleotide. The promoters may be identical to or share a high degree of sequence identity (e.g., at least about 80%, at least about 85%, at least about 90%, at least about 95%, at least about 96%, at least about 97%, at least about 98%, or at least about 99%) with a selected native promoter.

Examples of suitable promoters for directing the transcription of the nucleic acid constructs in a yeast cells, include, but are not limited to, the promoters obtained from the genes for enolase, (e.g., *S. cerevisiae* enolase or *I. orientalis* enolase (ENO1)), galactokinase (e.g., *S. cerevisiae* galactokinase or *I. orientalis* galactokinase (GAL1)), alcohol dehydrogenase/glyceraldehyde-3-phosphate dehydrogenase (e.g., *S. cerevisiae* alcohol dehydrogenase/glyceraldehyde-3-phosphate dehydrogenase or *I. orientalis* alcohol dehydrogenase/glyceraldehyde-3-phosphate dehydrogenase (ADH1, ADH2/GAP)), triose phosphate isomerase (e.g., *S. cerevisiae* triose phosphate isomerase or *I. orientalis* triose phosphate isomerase (TPI)), metallothionein (e.g., *S. cerevisiae* metallothionein or *I. orientalis* metallothionein (CUP1)), 3-phosphoglycerate kinase (e.g., *S. cerevisiae* 3-phosphoglycerate kinase or *I. orientalis* 3-phosphoglycerate kinase (PGK)), PDC1, xylose reductase (XR), xylitol dehydrogenase (XDH), L-(+)-lactate-cytochrome c oxidoreductase (CYB2), translation elongation factor-1 (TEF1), translation elongation factor-2 (TEF2), glyceraldehyde-3-phosphate dehydrogenase (GAPDH), and orotidine 5'-phosphate decarboxylase (URA3) genes. Other suitable promoters may be obtained from *S. cerevisiae* TDH3, HXT7, PGK1, RPL18B and CCW12 genes. Additional useful promoters for yeast host cells are described by Romanos et al., 1992, *Yeast* 8:423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the yeast cell of choice may be used. The terminator may be identical to or share a high degree of sequence identity (e.g., at least about 80%, at least about 85%, at least about 90%, at least about 95%, at least about 96%, at least about 97%, at least about 98%, or at least about 99%) with the selected native terminator.

Suitable terminators for yeast host cells may be obtained from the genes for enolase (e.g., *S. cerevisiae* or *I. orientalis* enolase cytochrome C (e.g., *S. cerevisiae* or *I. orientalis* cytochrome (CYC1)), glyceraldehyde-3-phosphate dehydrogenase (e.g., *S. cerevisiae* or *I. orientalis* glyceraldehyde-3-phosphate dehydrogenase (gpd)), PDC1, XR, XDH, transaldolase (TAL), transketolase (TKL), ribose 5-phosphate ketol-isomerase (RKI), CYB2, and the galactose family of genes (especially the GAL10 terminator). Other suitable terminators may be obtained from *S. cerevisiae* ENO2 or TEF1 genes. Additional useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177:3465-3471).

The control sequence may also be a suitable leader sequence, when transcribed is a non-translated region of an mRNA that is important for translation by the host cell. The leader sequence is operably linked to the 5'-terminus of the polynucleotide encoding the polypeptide. Any leader sequence that is functional in the yeast cell of choice may be used.

Suitable leaders for yeast host cells are obtained from the genes for enolase (e.g., *S. cerevisiae* or *I. orientalis* enolase (ENO-1)), 3-phosphoglycerate kinase (e.g., *S. cerevisiae* or

*I. orientalis* 3-phosphoglycerate kinase), alpha-factor (e.g., *S. cerevisiae* or *I. orientalis* alpha-factor), and alcohol dehydrogenase/glyceraldehyde-3-phosphate dehydrogenase (e.g., *S. cerevisiae* or *I. orientalis* alcohol dehydrogenase/glyceraldehyde-3-phosphate dehydrogenase (ADH2/GAP)).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used. Useful polyadenylation sequences for yeast cells are described by Guo and Sherman, 1995, *Mol. Cellular Biol.* 15:5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used. Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used.

The vectors may contain one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3.

The vectors may contain one or more (e.g., two, several) elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination. Potential integration loci include those described in the art (e.g., See US2012/0135481).

For autonomous replication, the vector may further comprise an origin of replication enabling the vector to replicate autonomously in the yeast cell. The origin of replication may be any plasmid replicator mediating autonomous replication that functions in a cell. The term "origin of replication" or "plasmid replicator" means a polynucleotide that enables a plasmid or vector to replicate in vivo. Examples of origins of replication for use in a yeast host cell are the 2 micron origin of replication, ARS1, ARS4, the combination of ARS1 and CEN3, and the combination of ARS4 and CEN6.

More than one copy of a polynucleotide described herein may be inserted into a host cell to increase production of a polypeptide. An increase in the copy number of the polynucleotide can be obtained by integrating at least one additional copy of the sequence into the yeast cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors described herein are well known to one skilled in the art (see, e.g., Sambrook et al., 1989, *Molecular Cloning, A Laboratory Manual,* 2d edition, Cold Spring Harbor, New York).

Additional procedures and techniques known in the art for the preparation of recombinant cells for ethanol fermentation, are described in, e.g., WO 2016/045569, the content of which is hereby incorporated by reference.

The host cell or fermenting organism may be in the form of a composition comprising a host cell or fermenting organism (e.g., a yeast strain described herein) and a naturally occurring and/or a non-naturally occurring component.

The host cell or fermenting organism described herein may be in any viable form, including crumbled, dry, including active dry and instant, compressed, cream (liquid) form etc. In one embodiment, the host cell or fermenting organism (e.g., a *Saccharomyces cerevisiae* yeast strain) is dry yeast, such as active dry yeast or instant yeast. In one embodiment, the host cell or fermenting organism (e.g., a *Saccharomyces cerevisiae* yeast strain) is crumbled yeast. In one embodiment, the host cell or fermenting organism (e.g., a *Saccharomyces cerevisiae* yeast strain) is compressed yeast. In one embodiment, the host cell or fermenting organism (e.g., a *Saccharomyces cerevisiae* yeast strain) is cream yeast.

In one embodiment is a composition comprising a host cell or fermenting organism described herein (e.g., a *Saccharomyces cerevisiae* yeast strain), and one or more of the component selected from the group consisting of: surfactants, emulsifiers, gums, swelling agent, and antioxidants and other processing aids.

The compositions described herein may comprise a host cell or fermenting organism described herein (e.g., a *Saccharomyces cerevisiae* yeast strain) and any suitable surfactants. In one embodiment, the surfactant(s) is/are an anionic surfactant, cationic surfactant, and/or nonionic surfactant.

The compositions described herein may comprise a host cell or fermenting organism described herein (e.g., a *Saccharomyces cerevisiae* yeast strain) and any suitable emulsifier. In one embodiment, the emulsifier is a fatty-acid ester of sorbitan. In one embodiment, the emulsifier is selected from the group of sorbitan monostearate (SMS), citric acid esters of monodiglycerides, polyglycerolester, fatty acid esters of propylene glycol.

In one embodiment, the composition comprises a host cell or fermenting organism described herein (e.g., a *Saccharomyces cerevisiae* yeast strain), and Olindronal SMS, Olindronal SK, or Olindronal SPL including composition concerned in European Patent No. 1,724,336 (hereby incorporated by reference). These products are commercially available from Bussetti, Austria, for active dry yeast.

The compositions described herein may comprise a host cell or fermenting organism described herein (e.g., a *Saccharomyces cerevisiae* yeast strain) and any suitable gum. In one embodiment, the gum is selected from the group of carob, guar, tragacanth, arabic, xanthan and acacia gum, in particular for cream, compressed and dry yeast.

The compositions described herein may comprise a host cell or fermenting organism described herein (e.g., a *Saccharomyces cerevisiae* yeast strain) and any suitable swelling agent. In one embodiment, the swelling agent is methyl cellulose or carboxymethyl cellulose.

The compositions described herein may comprise a host cell or fermenting organism described herein (e.g., a *Saccharomyces cerevisiae* yeast strain) and any suitable antioxidant. In one embodiment, the antioxidant is butylated hydroxyanisol (BHA) and/or butylated hydroxytoluene (BHT), or ascorbic acid (vitamin C), particular for active dry yeast.

The host cells and fermenting organisms described herein may also comprise one or more (e.g., two, several) gene disruptions, e.g., to divert sugar metabolism from undesired products to ethanol. In some embodiments, the recombinant host cells produce a greater amount of ethanol compared to the cell without the one or more disruptions when cultivated under identical conditions. In some embodiments, one or more of the disrupted endogenous genes is inactivated.

In certain embodiments, the host cell or fermenting organism provided herein comprises a disruption of one or more endogenous genes encoding enzymes involved in producing alternate fermentative-products-such as glycerol or other byproducts such as acetate or diols. For example, the cells provided herein may comprise a disruption of one or more of glycerol 3-phosphate dehydrogenase (GPD, catalyzes reaction of dihydroxyacetone phosphate to glycerol 3-phosphate), glycerol 3-phosphatase (GPP, catalyzes conversion of glycerol-3 phosphate to glycerol), glycerol kinase (catalyzes conversion of glycerol 3-phosphate to glycerol), dihydroxyacetone kinase (catalyzes conversion of dihydroxyacetone phosphate to dihydroxyacetone), glycerol dehydrogenase (catalyzes conversion of dihydroxyacetone to glycerol), and aldehyde dehydrogenase (ALD, e.g., converts acetaldehyde to acetate).

Modeling analysis can be used to design gene disruptions that additionally optimize utilization of the pathway. One exemplary computational method for identifying and designing metabolic alterations favoring biosynthesis of a desired product is the OptKnock computational framework, Burgard et al., 2003, *Biotechnol. Bioeng.* 84:647-657.

The host cells and fermenting organisms comprising a gene disruption may be constructed using methods well known in the art, including those methods described herein. A portion of the gene can be disrupted such as the coding region or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, but are not limited to, a leader, propeptide sequence, signal sequence, transcription terminator, and transcriptional activator.

The host cells and fermenting organisms comprising a gene disruption may be constructed by gene deletion techniques to eliminate or reduce expression of the gene. Gene deletion techniques enable the partial or complete removal of the gene thereby eliminating their expression. In such methods, deletion of the gene is accomplished by homologous recombination using a plasmid that has been constructed to contiguously contain the 5' and 3' regions flanking the gene.

The host cells and fermenting organisms comprising a gene disruption may also be constructed by introducing, substituting, and/or removing one or more (e.g., two, several) nucleotides in the gene or a control sequence thereof required for the transcription or translation thereof. For example, nucleotides may be inserted or removed for the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, *Science* 229:4719; Lo et al., 1985, *Proc. Natl. Acad. Sci. U.S.A.* 81:2285; Higuchi et al., 1988, *Nucleic Acids Res* 16:7351; Shimada, 1996, *Meth. Mol. Biol.* 57:157; Ho et al., 1989, *Gene* 77:61; Horton et al., 1989, *Gene* 77:61; and Sarkar and Sommer, 1990, *BioTechniques* 8:404.

The host cells and fermenting organisms comprising a gene disruption may also be constructed by inserting into the gene a disruptive nucleic acid construct comprising a nucleic acid fragment homologous to the gene that will create a duplication of the region of homology and incorporate construct DNA between the duplicated regions. Such a gene disruption can eliminate gene expression if the inserted construct separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The host cells and fermenting organisms comprising a gene disruption may also be constructed by the process of gene conversion (see, for example, Iglesias and Trautner, 1983, *Molecular General Genetics* 189:73-76). For example, in the gene conversion method, a nucleotide sequence corresponding to the gene is mutagenized in vitro to produce a defective nucleotide sequence, which is then transformed into the recombinant strain to produce a defective gene. By homologous recombination, the defective nucleotide sequence replaces the endogenous gene. It may be desirable that the defective nucleotide sequence also comprises a marker for selection of transformants containing the defective gene.

The host cells and fermenting organisms comprising a gene disruption may be further constructed by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp. 363-433, Academic Press, New York, 1970). Modification of the gene may be performed by subjecting the parent strain to mutagenesis and screening for mutant strains in which expression of the gene has been reduced or inactivated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosogaunidine (NTG)O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of the gene.

A nucleotide sequence homologous or complementary to a gene described herein may be used from other microbial sources to disrupt the corresponding gene in a recombinant strain of choice.

In one embodiment, the modification of a gene in the recombinant cell is unmarked with a selectable marker. Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery

Subsequent to fermentation, or SSF, the fermentation product may be separated from the fermentation medium. The slurry may be distilled to extract the desired fermentation product (e.g., ethanol). Alternatively, the desired fermentation product may be extracted from the fermentation medium by micro or membrane filtration techniques. The fermentation product may also be recovered by stripping or other method well known in the art.

Alpha-Amylase Present and/or Added During Liquefaction

According to the invention an alpha-amylase is present and/or added during liquefaction together with an optional thermostable protease, optional carbohydrate-source generating enzyme, in particular a thermostable glucoamylase, and/or optional pullulanase.

The alpha-amylase added during liquefaction step i) may be any alpha-amylase. Preferred are bacterial alpha-amylases, which typically are stable at temperature used during liquefaction.

Any alpha-amylase herein contemplated as being present and/or added during liquefaction is also contemplated for expression by a fermenting organism or host cell.

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis,*

*Bacillus stearothermophilus*, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 14 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated so it has around 491 amino acids compared to SEQ ID NO: 3 in WO 99/19467.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873-see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 14 herein or the deletion of amino acids R179 and G180 using SEQ ID NO: 3 in WO 99/19467 or SEQ ID NO: 14 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 14 herein. The bacterial alpha-amylase may also have a substitution in a position corresponding to S239 in the *Bacillus licheniformis* alpha-amylase shown in SEQ ID NO: 4 in WO 99/19467, or a S242 variant of the *Bacillus stearothermophilus* alpha-amylase of SEQ ID NO: 3 in WO 99/19467 or SEQ ID NO: 14 herein.

In an embodiment the variant is a S242A, E or Q variant, preferably a S242Q variant, of the *Bacillus stearothermophilus* alpha-amylase (using SEQ ID NO: 14 herein for numbering).

In an embodiment the variant is a position E188 variant, preferably E188P variant of the *Bacillus stearothermophilus* alpha-amylase (using SEQ ID NO: 14 herein for numbering).

The bacterial alpha-amylase may in an embodiment be a truncated alpha-amylase. Especially the truncation is so that the *Bacillus stearothermophilus* alpha-amylase shown in SEQ ID NO: 3 in WO 99/19467 or SEQ ID NO: 14 herein, is around 491 amino acids long, such as from 480 to 495 amino acids long.

Most importantly, a suitable alpha-amylase for use in liquefaction must have sufficient thermstability, and thus accordingly any alpha-amylase having a T½ (min) at pH 4.5, 85° C., 0.12 mM $CaCl_2$)) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70, may be used.

According to the invention the alpha-amylase may be a thermostable alpha-amylase, such as a thermostable bacterial alpha-amylase, preferably from *Bacillus stearothermophilus*. In an embodiment the alpha-amylase used according to the invention has a T½ (min) at pH 4.5, 85° C., 0.12 mM $CaCl_2$) of at least 10.

In an embodiment the thermostable alpha-amylase has a T½ (min) at pH 4.5, 85° C., 0.12 mM $CaCl_2$), of at least 15.

In an embodiment the thermostable alpha-amylase has a T½ (min) at pH 4.5, 85° C., 0.12 mM $CaCl_2$), of as at least 20.

In an embodiment the thermostable alpha-amylase has a T½ (min) at pH 4.5, 85° C., 0.12 mM $CaCl_2$), of as at least 25.

In an embodiment the thermostable alpha-amylase has a T½ (min) at pH 4.5, 85° C., 0.12 mM $CaCl_2$), of as at least 30.

In an embodiment the thermostable alpha-amylase has a T½ (min) at pH 4.5, 85° C., 0.12 mM $CaCl_2$), of as at least 40.

In an embodiment the thermostable alpha-amylase has a T½ (min) at pH 4.5, 85° C., 0.12 mM $CaCl_2$), of at least 50.

In an embodiment the thermostable alpha-amylase has a T½ (min) at pH 4.5, 85° C., 0.12 mM $CaCl_2$), of at least 60.

In an embodiment the thermostable alpha-amylase has a T½ (min) at pH 4.5, 85° C., 0.12 mM $CaCl_2$), between 10-70.

In an embodiment the thermostable alpha-amylase has a T½ (min) at pH 4.5, 85° C., 0.12 mM $CaCl_2$), between 15-70.

In an embodiment the thermostable alpha-amylase has a T½ (min) at pH 4.5, 85° C., 0.12 mM $CaCl_2$), between 20-70.

In an embodiment the thermostable alpha-amylase has a T½ (min) at pH 4.5, 85° C., 0.12 mM $CaCl_2$), between 25-70.

In an embodiment the thermostable alpha-amylase has a T½ (min) at pH 4.5, 85° C., 0.12 mM $CaCl_2$), between 30-70.

In an embodiment the thermostable alpha-amylase has a T½ (min) at pH 4.5, 85° C., 0.12 mM $CaCl_2$), between 40-70.

In an embodiment the thermostable alpha-amylase has a T½ (min) at pH 4.5, 85° C., 0.12 mM $CaCl_2$), between 50-70.

In an embodiment the thermostable alpha-amylase has a T½ (min) at pH 4.5, 85° C., 0.12 mM $CaCl_2$), between 60-70.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 (SEQ ID NO: 14 herein) with one or two amino acids deleted at positions R179, G180, I181 and/or G182, in particular with R179 and G180 deleted, or with I181 and G182 deleted, with mutations in below list of mutations.

In preferred embodiments the *Bacillus stearothermophilus* alpha-amylases have double deletion I181+G182, and optional substitution N193F, further comprising mutations selected from below list.

In a preferred embodiment the alpha-amylase is selected from the following group of *Bacillus stearothermophilus* alpha-amylase variants (using SEQ ID NO: 14 for numbering):

I181*+G182*+N193F+E129V+K177L+R179E;
I181*+G182*+N193F+V59A+Q89R+E129V+K177L+R179E+H208Y+K220P+N224L+Q254S
I181*+G182*+N193F+V59A+Q89R+E129V+K177L+R179E+Q254S+M284V;
I181*+G182*+N193F+V59A+E129V+K177L+R179E+Q254S+M284V;
I181*+G182*+N193F+E129V+K177L+R179E+K220P+N224L+S242Q+Q254S;
I181*+G182*+V59A+E129V+K177L+R179E+Q254S+M284V+V212T+Y268G+N293Y+T297N;
I181*+G182*+V59A+E129V+K177L+R179E+Q254S+M284V+V212T+Y268G+N293Y+T297N+S173N+E188P+H208Y+S242Y+K2791;
I181*+G182*+V59A+E129V+K177L+R179S+Q254S+M284V+V212T+Y268G+N293Y+T297N+A184Q+E188P+T191N
I181*+G182*+V59A+E129V+K177L+R179S+Q254S+M284V+V212T+Y268G+N293Y+T297N+A184Q+E188P+T191N+S242Y+K2791;
I181*+G182*+V59A+E129V+K177L+R179E+Q254S+M284V+V212T+Y268G+N293Y+T297N+E188P+K279W;
I181*+G182*+V59A+E129V+K177L+R179E+Q254S+M284V+V212T+Y268G+N293Y+T297N+W115D+D117Q+T133P; and wherein the variant has at least 85%, at least 90%, at least 95%, at least 96%, at least 97%, at least 98%, or at least 99% sequence identity to SEQ ID NO: 14.

It should be understood, that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 14 herein, or variants thereof, are truncated in the C-terminal and are typically around 491 amino acids long, such as from 480-495 amino acids long.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 14 herein.

Protease Present and/or Added During Liquefaction 20

According to the invention a thermostable protease is optionally present and/or added during liquefaction together with an alpha-amylase, and optionally a carbohydrate-source generating enzyme, in particular a thermostable glucoamylase, and/or optionally a pullulanase.

Any protease herein contemplated as being present and/or added during liquefaction is also contemplated for expression by a fermenting organism or host cell.

Proteases are classified on the basis of their catalytic mechanism into the following groups: Serine proteases(S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay described in the "Materials & Methods" section.

There are no limitations on the origin of the protease used in a process of the invention as long as it fulfills the thermostability properties defined below.

In one embodiment the protease is of fungal origin.

The protease may be a variant of, e.g., a wild-type protease as long as the protease has the thermostability properties defined herein.

In a particular embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 15 herein further with mutations selected from below list S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;

T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In a preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 15 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 15 herein.

The thermostable protease may also be derived from any bacterium as long as the protease has the thermostability properties defined according to the invention. In one embodiment the protease is a serine protease, particularly a S8 protease. Preferred proteases are, serine proteases, particularly an S8 serine protease derived from a strain of *Pyrococcus*, preferably a strain of *Pyrococcus furiosus*, or derived from a strain of *Thermococcus*, preferably *Themococcus thioreducens*, or derived from a strain of *Palaeococcus*, preferably *Palaeococcus ferrophilus.*

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company), SEQ ID NO: 16 herein.

In another embodiment the thermostable protease is one disclosed in SEQ ID NO: 16 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 16 herein.

The *Pyrococcus furiosus* protease is a thermostable protease according to the invention. The *Pyrococcus furiosus* protease (PfuS) was found to have a thermostability of 110% (80° C./70° C.) and 103% (90° C./70° C.) at pH 4.5 determined as described in Example 2 herein.

In an embodiment the thermostable protease is derived from a strain of the bacterium *Palaeococcus*, such as a strain of *Palaeococcus ferrophilus*. In an embodiment the protease is the one shown as SEQ ID NO: 17 herein. In another embodiment the thermostable protease is one disclosed in SEQ ID NO: 17 herein or a protease having at least 80% identity, such as at least 85%, such as at least 90%, such as at least 95%, such as at least 96%, such as at least 97%, such as at least 98%, such as at least 99% identity to SEQ ID NO: 17.

In one embodiment a thermostable protease used in a process of the invention has a thermostability value of more than 20% determined as Relative Activity at 80° C./70° C.

In an embodiment the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C.

In an embodiment the protease has a thermostability between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 10% determined as Relative Activity at 85° C./70° C.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

In an embodiment the protease may have a themostability for above 90, such as above 100 at 85° C. as determined using the Zein-BCA assay.

In an embodiment the protease has a themostability above 60%, such as above 90%, such as above 100%, such as above 110% at 85° C. as determined using the Zein-BCA assay.

In an embodiment protease has a themostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay.

In an embodiment the protease is derived from a strain of Thermobifida, such as the *Thermobifida cellulosytica* protease shown in SEQ ID NO: 18 herein, or one having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity to the amino acid sequence of SEQ ID NO: 18.

In an embodiment the protease is derived from a strain of Thermobifida, such as the *Thermobifida fusca* protease shown in SEQ ID NO: 19 herein (referred to as SEQ ID NO: 8 in WO2018/118815 A1, which is incorporated herein by reference in its entirety), or one having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity to the amino acid sequence of SEQ ID NO: 19.

In an embodiment the protease is derived from a strain of *Thermobifida*, such as the *Thermobifida halotolerans* protease shown in SEQ ID NO: 20 herein (referred to as SEQ ID NO: 10 in WO2018/118815 A1, which is incorporated herein by reference in its entirety), or one having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity to the amino acid sequence of SEQ ID NO: 20.

In an embodiment the protease is derived from a strain of *Thermococcus*, such as the *Thermococcus* nautili protease shown in SEQ ID NO: 21 herein (referred to as SEQ ID NO: 3 in WO2018/169780A1, which is incorporated herein by reference in its entirety), or one having at least 60%, such as at least 70%, such as at least 75% identity, at least 76% identity, at least 77% identity, at least 78% identity, at least 79% identity, preferably at least 80%, at least 81% identity, at least 82% identity, at least 83% identity, at least 84% identity, more preferably at least 85% identity, at least 86% identity, at least 87% identity, at least 88% identity, at least 89% identity, more preferably at least 90% identity, more preferably at least 91% identity, more preferably at least 92% identity, at least 93% identity, at least 94% identity, or at least 95% identity, such as at least 96% identity, at least 97% identity, at least 98% identity, at least 99% identity to the amino acid sequence of SEQ ID NO: 21.

Carbohydrate-Source Generating Enzyme Present and/or Added During Liquefaction

According to the invention a carbohydrate-source generating enzyme, in particular a glucoamylase, preferably a thermostable glucoamylase, may optionally be present and/or added during liquefaction together with an alpha-amylase and an optional thermostable protease. As mentioned above, a pullulanase may also be optionally be present and/or added during liquefaction step i).

Any carbohydrate-source generating enzymes (e.g., glucoamylase) herein contemplated as being present and/or added during liquefaction is also contemplated for expression by a fermenting organism or host cell.

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is thermostable. The carbohydrate-source generating enzyme, in particular thermostable glucoamylase, may be added together with or separately from the alpha-amylase and the thermostable protease.

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum*, in particular the *Penicillium oxalicum* glucoamylase disclosed as SEQ ID NO: 2 in PCT/CN10/071753 published as WO 2011/127802 (which is hereby incorporated by reference) and shown in SEQ ID NO: 22 herein.

In an embodiment the thermostable glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO2011/127802 or SEQ ID NOs: 23 herein.

In a preferred embodiment the carbohydrate-source generating enzyme is a variant of the *Penicillium oxalicum* glucoamylase disclosed as SEQ ID NO: 2 in WO2011/

127802 and SEQ ID NO: 22 herein, having a K79V substitution (using the mature sequence shown in SEQ ID NO: 22 for numbering). The K79V glucoamylase variant has reduced sensitivity to protease degradation relative to the parent as disclosed in U.S. application No. 61/531,189 or PCT/US12/053779 (which are hereby incorporated by reference).

In an embodiment the carbohydrate-source generating enzyme, in particular thermostable glucoamylase, is derived from *Penicillium oxalicum.*

In an embodiment the thermostable glucoamylase is a variant of the *Penicillium oxalicum* glucoamylase disclosed as SEQ ID NO: 2 in WO2011/127802 and shown in SEQ ID NO: 22 herein. In a preferred embodiment the *Penicillium oxalicum* glucoamylase is the one disclosed as SEQ ID-NO: 2 in WO2011/127802 and shown in SEQ ID NO: 22 herein having Val (V) in position 79 (using SEQ ID NO: 22 for numbering).

In an embodiment these variants have reduced sensitivity to protease degradation.

In an embodiment these variants have improved thermostability compared to the parent.

More specifically, in an embodiment the glucoamylase has a K79V substitution (using SEQ ID NO: 22 for numbering), corresponding to the PE001 variant, and further comprises at least one of the following substitutions or combination of substitutions:

P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T.

The carbohydrate-source generating enzyme, in particular, may be added in amounts from 0.1-100 micrograms EP/g, such as 0.5-50 micrograms EP/g, such as 1-25 micrograms EP/g, such as 2-12 micrograms EP/g DS.

Carbohydrate-Source Generating Enzyme Present and/or Added During Saccharification and/or Fermentation According to the invention a carbohydrate-source generating enzyme, preferably a glucoamylase, may be present and/or added during saccharification and/or fermentation.

In a preferred embodiment the carbohydrate-source generating enzyme is a glucoamylase, of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*, or a strain of *Trametes*, preferably *Trametes cingulata*, or a strain of *Pycnoporus*, or a strain of *Gloeophyllum*, such as a strain of *Gloeophyllum sepiarium* or *Gloeophyllum trabeum* or a strain of the *Nigrofomes.*

Any glucoamylase contemplated as being present and/or added during saccharification and/or fermentation is also contemplated for expression by a fermenting organism or host cell.

Glucoamylases

According to the invention the glucoamylase present and/or added during saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted Corticium *rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (US patent no. Re. 32,153), *Talaromyces duponti, Talaromyces thermophilus* (U.S. Pat. No. 4,587,215). In a preferred embodiment the glucoamylase used during 10 saccharification and/or fermentation is the *Talaromyces emersonii* glucoamylase disclosed in WO 99/28448.

Contemplated fungal glucoamylases include particularly glucoamylases derived from *Talaromyces*, preferably *T. emersonii*, or a strain of *Trametes*, preferably *Trametes cingulata*, or a strain of *Pycnoporus*, or a strain of *Gloeophyllum*, such as a strain of *Gloeophyllum sepiarium* or *Gloeophyllum trabeum* or a strain of the *Nigrofomes.*

In one embodiment the glucoamylase is derived from a strain of the genus *Trametes*, in particular a strain of *Trametes cingulata*, disclosed in WO 2006/069289 or in SEQ ID NO: 24 herein. In one embodiment the glucoamylase is derived from a strain of the genus *Talaromyces*, in particular a strain of *Talaromyces emersonii* disclosed in SEQ ID NO: 27 herein.

In another embodiment the glucoamylase is derived from a strain of the genus *Pycnoporus*, in particular a strain of *Pycnoporus sanguineus* as described in WO 2011/066576 (SEQ ID NOs 2, 4 or 6) or SEQ ID NO: 25 herein, or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is SEQ ID NO: 13 herein. In another embodiment the glucoamylase is SEQ ID NO: 26 herein. In an embodiment the glucoamylase is derived from a strain of the genus *Nigrofomes*, in particular a strain of *Nigrofomes* sp. disclosed in WO 2012/064351 as SEQ ID NO: 2. Contemplated are also glucoamylases which exhibit a high identity to any of the above mentioned glucoamylases, i.e., at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs: 24, 25, 26, 27, or 28 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

In an embodiment the glucoamylase is added as a blend further comprising an alpha-amylase. In a preferred embodiment the alpha-amylase is a fungal alpha-amylase, especially an acid fungal alpha-amylase. The alpha-amylase is typically a side activity.

In an embodiment the glucoamylase is a blend comprising *Talaromyces emersonii* glucoamylase disclosed in WO 99/28448 as SEQ ID NO: 7 or SEQ ID NO: 27 herein and *Trametes cingulata* glucoamylase disclosed in WO 06/069289 and SEQ ID NO: 24 herein.

In an embodiment the glucoamylase is a blend comprising *Talaromyces emersonii* glucoamylase disclosed SEQ ID NO: 27, *Trametes cingulata* glucoamylase disclosed as SEQ ID NO: 24, and *Rhizomucor pusillus* alpha-amylase with *Aspergillus niger* glucoamylase linker and SBD disclosed as V039 in Table 5 in WO 2006/069290 and as SEQ ID NO: 11 herein, preferably with the following substitutions: G128D+D143N.

In an embodiment the glucoamylase is a blend comprising *Gloeophyllum sepiarium* glucoamylase shown as SEQ ID NO: 2 in WO 2011/068803 (SEQ ID NO: 13 herein) and *Rhizomucor pusillus* with an *Aspergillus niger* glucoamylase linker and starch-binding domain (SBD), disclosed SEQ ID NO: 3 in WO 2013/006756 (SEQ ID NO: 11 herein) with the following substitutions: G128D+D143N.

In an embodiment the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R+V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 3 in WO 2013/006756 for numbering).

Commercially available compositions comprising glucoamylase include AMG 200L; AMG 300 L; SAN™ SUPER, SAN™ EXTRA L, SPIRIZYMET PLUS, SPIRIZYMET FUEL, SPIRIZYME™ B4U, SPIRIZYME™ ULTRA, SPIRIZYMET EXCEL, SPIRIZYME ACHIEVE and AMG™ E (from Novozymes A/S); OPTIDEX™ 300, GC480, GC417 (from DuPont-Genencor); AMIGASE™ and AMIGASE™ PLUS (from DSM); G-ZYMET G900, G-ZYMET and G990 ZR (from DuPont-Genencor).

Cellulolytic Composition Present and/or Added During Saccharification and/or Fermentation According to the invention a cellulolytic composition is present during fermentation or simultaneous saccharification and fermentation (SSF).

The cellulolytic composition may be any cellulolytic composition, comprising a beta-glucosidase, a cellobiohydrolase and an endoglucanase.

Any cellulase described herein contemplated as being present and/or added during saccharification and/or fermentation is also contemplated for expression by a fermenting organism or host cell.

The compositions may comprise a polypeptide of the present invention as the major enzymatic component, e.g., a mono-component composition. Alternatively, the compositions may comprise multiple enzymatic activities, such as one or more (e.g., several) additional enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

The compositions may be prepared in accordance with methods known in the art and may be in the form of a liquid or a dry composition. The compositions may be stabilized in accordance with methods known in the art.

The compositions may be a fermentation broth formulation or a cell composition, as described herein. Consequently, the present invention also relates to fermentation broth formulations and cell compositions comprising a polypeptide having cellobiohydrolase, endoglucanase, or beta-glucosidase activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextnnases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Additional examples of suitable cellulolytic composition can be found in WO 2008/151079 and co-pending patent application PCT/US12/052163 published as WO2013/028928 which are incorporated by reference.

In preferred embodiments the cellulolytic composition is derived from a strain of *Trichoderma, Humicola*, or *Chrysosporium.*

In an embodiment the cellulolytic composition is derived from a strain of *Trichoderma reesei, Humicola insolens* and/or *Chrysosporium lucknowense.*

In an embodiment the cellulolytic composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in WO2005/047499 or SEQ ID NO: 8 herein or an *Aspergillus fumigatus* beta-glucosidase variant disclosed in WO 2012/044915 (Novozymes), such as one with the following substitutions F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei.*

In an embodiment the cellulolytic composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 7 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 2 in WO 2011/057140 or SEQ ID NO: 9 herein, or a strain of the genus *Trichoderma*, such as a strain of *Trichoderma reesei.*

In an embodiment the cellulolytic composition comprises a cellobiohydrolase II (CBH II, such as one derived from a strain of the genus *Aspergillus*, such as a strain of *Aspergillus fumigatus* or SEQ ID NO: 10 herein; or a strain of the genus *Trichoderma*, such as *Trichoderma reesei*, or a strain of the genus *Thielavia*, such as a strain of *Thielavia terrestris*, such as cellobiohydrolase II CEL6A. from *Thielavia terrestris.*

In an embodiment the cellulolytic composition comprises a GH61 polypeptide having cellulolytic enhancing activity and a beta-glucosidase.

In an embodiment the cellulolytic composition comprises a GH61 polypeptide having cellulolytic enhancing activity, a beta-glucosidase, and a CBH I.

In an embodiment the cellulolytic composition comprises a GH61 polypeptide having cellulolytic enhancing activity, a beta-glucosidase, a CBH I, and a CBH II.

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 8 herein.

In an embodiment the cellulolytic composition is a *Trichoderma reesei* cellulolytic enzyme composition further comprising *Penicillium emersonii* GH61A polypeptide having cellulolytic enhancing activity disclosed in WO 2011/041397 and *Aspergillus fumigatus* beta-glucosidase (SEQ ID NO: 2 of WO 2005/047499) or SEQ ID NO: 8 herein or a variant thereof with the following substitutions F100D, S283G, N456E, F512Y.

In an embodiment, the cellulolytic composition, for example a *Trichoderma reesei* cellulolytic enzyme composition, comprises one or more polypeptides selected from the group consisting of:

beta-glucosidase;

cellobiohydrolase I; and endoglucanase I, or a mixture of two or three thereof.

In an embodiment, the cellulolytic composition, for example a *Trichoderma reesei* cellulolytic enzyme composition, comprises one or more of the following components:

(i) an *Aspergillus fumigatus* beta-glucosidase or a variant thereof;

(ii) an *Aspergillus fumigatus* cellobiohydrolase I; and (iii) a *Trichoderma reesei* endoglucanase I.

In an embodiment, the cellulolytic composition is a *Trichoderma reesei* cellulolytic composition further comprising:

(i) an *Aspergillus fumigatus* beta-glucosidase disclosed in SEQ ID NO: 8 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 8; (ii) a cellobiohydrolase I (CBH I), such as one derived from a strain of the genus *Aspergillus*, such as a strain of *Aspergillus fumigatus*, such as the CBHI disclosed as SEQ ID NO: 9, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 9; and (iii) an endoglucanase I (EGI), such as one derived from a strain of the genus *Trichoderma*, such as a strain of *Trichoderma reesei*, such as the EGI disclosed as SEQ ID NO: 29, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 29.

In a preferred embodiment the cellulolytic composition comprising one or more of the following components:

(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

In an preferred embodiment the cellulolytic composition is derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 7 herein), *Aspergillus fumigatus* beta-glucosidase (SEQ ID NO: 2 in WO 2005/047499 SEQ ID NO: 8 herein) variant F100D, S283G, N456E, F512Y) disclosed in WO 2012/044915; *Aspergillus fumigatus* Cel7A CBH1 disclosed as SEQ ID NO: 6 in WO2011/057140 (SEQ ID NO: 9 herein) and *Aspergillus fumigatus* CBH II disclosed as SEQ ID NO: 18 in WO 2011/057140 (SEQ ID NO: 10 herein).

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Hemicellulolytic Composition Present and/or Added During Saccharification and/or Fermentation According to the invention a hemicellulolytic composition is present during fermentation or simultaneous saccharification and fermentation (SSF).

The hemicellulolytic composition may be any hemicellulolytic composition, comprising a xylanase, and an arabinofuranosidase.

Any hemicellulase described herein contemplated as being present and/or added during saccharification and/or fermentation is also contemplated for expression by a fermenting organism or host cell.

The compositions may be prepared in accordance with methods known in the art and may be in the form of a liquid or a dry composition. The compositions may be stabilized in accordance with methods known in the art.

The compositions may be a fermentation broth formulation or a cell composition, as described herein.

In an embodiment, the hemicellulolytic composition comprises:

(i) a GH10 xylanase; and
(ii) a GH62 arabinofuranosidase.

In an embodiment, the hemicellulolytic composition comprises:

(i) a GH10 xylanase from *Talaromyces leycettanus*; and
(ii) a GH62 arabinofuranosidase from *Talaromyces pinophilus.*

In an embodiment, the hemicellulolytic composition comprises:

(i) a GH10 xylanase, such as one derived from a strain of the genus *Talaromyces*, such as a strain of *Talaromyces leycettanus*, such as the one disclosed as SEQ ID NO: 59, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 59; and
(ii) a GH62 arabinofuranosidase, such as one derived from a strain of the genus *Talaromyces*, such as a strain of *Talaromyces pinophilus*, such as the one disclosed as SEQ ID NO: 60, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 60.

In an embodiment the hemicellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Fiber Degrading Enzyme Blend

Aspects of the present invention relate to a fiber degrading enzyme blend comprising at least one polypeptide of the present invention (e.g., a cellulolytic composition) and a hemicellulolytic composition.

Any cellulase/cellulolytic composition and hemicellulase/hemicellulolytic composition described herein can be used in the fiber degrading enzyme blend.

In an example embodiment, the fiber degrading enzyme blend comprises at least one polypeptide having cellobiohydrolase activity, endoglucanase activity, or beta-glucosidase activity, and a hemicellulolytic composition comprising a xylanase and an arabinofuranosidase, wherein the at least one polypeptide having cellobiohydrolase activity, endoglucanase activity, or beta-glucosidase activity comprises at least one, at least two, at least three, at least four, at least five polypeptides, or at least six polypeptides selected from the group consisting of: (i) the mature polypeptide of SEQ ID NO: 1, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, or at least 99% identity to SEQ ID NO: 1; (ii) the mature polypeptide of SEQ ID NO: 2, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 2; (iii) the mature polypeptide of SEQ ID NO: 3, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 3; (iv) the mature polypeptide of SEQ ID NO: 4, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 4; (v) the mature polypeptide of SEQ ID NO: 5, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 5; and (vi) the mature polypeptide of SEQ ID NO: 6, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 6.

In an example embodiment, the fiber degrading enzyme blend comprises at least one polypeptide having cellobiohydrolase activity, endoglucanase activity, or beta-glucosidase activity, and a hemicellulolytic composition comprising a GH10 xylanase and a GH62 arabinofuranosidase, wherein the at least one polypeptide having cellobiohydrolase activity, endoglucanase activity, or beta-glucosidase activity comprises at least one, at least two, at least three, at least four, at least five polypeptides, or at least six polypeptides selected from the group consisting of: (i) the mature polypeptide of SEQ ID NO: 1, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, or at least 99% identity to SEQ ID NO: 1; (ii) the mature polypeptide of SEQ ID NO: 2, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 2; (iii) the mature polypeptide of SEQ ID NO: 3, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 3; (iv) the mature polypeptide of SEQ ID NO: 4, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 4; (v) the mature polypeptide of SEQ ID NO: 5, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 5; and (vi) the mature polypeptide of SEQ ID NO: 6, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 6.

In an example embodiment, the fiber degrading enzyme blend comprises at least one polypeptide having cellobiohydrolase activity, endoglucanase activity, or beta-glucosidase activity, and a hemicellulolytic composition comprising a *Talaromyces* GH10 xylanase and a *Talaromyces* GH62 arabinofuranosidase, wherein the at least one polypeptide having cellobiohydrolase activity, endoglucanase activity, or beta-glucosidase activity comprises at least one, at least two, at least three, at least four, at least five polypeptides, or at least six polypeptides selected from the group consisting of: (i) the mature polypeptide of SEQ ID NO: 1, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, or at least 99% identity to SEQ ID NO: 1; (ii) the mature polypeptide of SEQ ID NO: 2, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 2; (iii) the mature polypeptide of SEQ ID NO: 3, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 3; (iv) the mature polypeptide of SEQ ID NO: 4, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 4; (v) the mature polypeptide of SEQ ID NO: 5, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 5; and (vi) the mature polypeptide of SEQ ID NO: 6, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 6.

In an example embodiment, the fiber degrading enzyme blend comprises at least one polypeptide having cellobiohydrolase activity, endoglucanase activity, or beta-glucosidase activity, and a hemicellulolytic composition comprising a *Talaromyces leycettanus* GH10 xylanase and a *Talaromyces pinophilus* GH62 arabinofuranosidase, wherein the at least one polypeptide having cellobiohydrolase activity, endoglucanase activity, or beta-glucosidase activity comprises at least one, at least two, at least three, at least four, at least five polypeptides, or at least six polypeptides selected from the group consisting of: (i) the mature polypeptide of SEQ ID NO: 1, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, or at least 99% identity to SEQ ID NO: 1; (ii) the mature polypeptide of SEQ ID NO: 2, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 2; (iii) the mature polypeptide of SEQ ID NO: 3, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 3; (iv) the mature polypeptide of SEQ ID NO: 4, or a polypeptide having at least 70% identity, at least 71% identity, at least 72%. identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 4; (v) the mature polypeptide of SEQ ID NO: 5, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 5; and (vi) the mature polypeptide of SEQ ID NO: 6, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 6.

In an example embodiment, the fiber degrading enzyme blend comprises at least one polypeptide having cellobiohydrolase activity, endoglucanase activity, or beta-glucosidase activity, wherein the at least one polypeptide having cellobiohydrolase activity, endoglucanase activity, or beta-glucosidase activity comprises at least one, at least two, at least three, at least four, at least five polypeptides, or at least six polypeptides selected from the group consisting of: (i) the mature polypeptide of SEQ ID NO: 1, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, or at least 99% identity to SEQ ID NO: 1; (ii) the mature polypeptide of SEQ ID NO: 2, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 2; (iii) the mature polypeptide of SEQ ID NO: 3, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 3; (iv) the mature polypeptide of SEQ ID NO: 4, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 4; (v) the mature polypeptide of SEQ ID NO: 5, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 5; and (vi) the mature polypeptide of SEQ ID NO: 6, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 6; and a hemicellulolytic composition comprising (i) a GH10 xylanase, such as one derived from a strain of the genus *Talaromyces*, such as a strain of *Talaromyces leycettanus*, such as the one disclosed as SEQ ID NO: 59, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 59; and (ii) a GH62 arabinofuranosidase, such as one derived from a strain of the genus *Talaromyces*, such as a strain of *Talaromyces pinophilus*, such as the one disclosed as SEQ ID NO: 60, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 60.

In an example embodiment, the fiber degrading enzyme blend comprises a cellulolytic composition and a hemicellulolytic composition, wherein the cellulolytic composition comprises two or three polypeptides selected from the group consisting of beta-glucosidase, cellobiohydrolase, and endoglucanase; and wherein the hemicellulolytic composition comprises an arabinofuranosidase and a xylanase.

In an example embodiment, the fiber degrading enzyme blend comprises a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises an arabinofuranosidase and a xylanase.

In an example embodiment, the fiber degrading enzyme blend comprises a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises a GH62 arabinofuranosidase and a GH10 xylanase.

In an example embodiment, the fiber degrading enzyme blend comprises a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises a *Talaromyces* GH62 arabinofuranosidase and a *Talaromyces* GH10 xylanase.

In an example embodiment, the fiber degrading enzyme blend comprises a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises a *Talaromyces pinophilus* GH62 arabinofuranosidase and a *Talaromyces leycettanus* GH10 xylanase.

In an example embodiment, the fiber degrading enzyme blend comprises a cellulolytic composition and a hemicellulolytic composition, wherein the cellulolytic composition comprises two or three polypeptides selected from the group consisting of beta-glucosidase, cellobiohydrolase I, and endoglucanase I; and wherein the hemicellulolytic composition comprises: (i) a GH10 xylanase, such as one derived from a strain of the genus *Talaromyces*, such as a strain of *Talaromyces leycettanus*, such as the one disclosed as SEQ ID NO: 59, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 59; and (ii) a GH62 arabinofuranosidase, such as one derived from a strain of the genus *Talaromyces*, such as a strain of *Talaromyces pinophilus*, such as the one disclosed as SEQ ID NO: 60, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least. 90% identity, at least 91% identity, at least-92% identity, at least 93% identity, at least 94% identity, at least 95% identity, at least 96% identity, at least 97% identity, at least 98% identity, or at least 99% identity to SEQ ID NO: 60.

In an example embodiment, the fiber degrading enzyme blend comprises a cellulolytic composition and a hemicellulolytic composition, wherein the cellulolytic composition comprises two or three polypeptides selected from the group consisting of an *Aspergillus* beta-glucosidase or a variant thereof; an *Aspergillus* cellobiohydrolase I; and a *Trichoderma* endoglucanase I; and wherein the hemicellulolytic composition comprises an arabinofuranosidase and a xylanase.

In an example embodiment, the fiber degrading enzyme blend comprises a cellulolytic composition and a hemicellulolytic composition, wherein the cellulolytic composition comprises two or three polypeptides selected from the group consisting of an *Aspergillus* beta-glucosidase or a variant thereof; an *Aspergillus* cellobiohydrolase I; and a *Trichoderma* endoglucanase I; and wherein the hemicellulolytic composition comprises an arabinofuranosidase and a xylanase, wherein the cellulolytic composition is derived from a strain of *Trichoderma*, such as *Trichoderma reesei*, or a strain of *Humicola*, such as *Humicola insolens*, or a strain of *Chrysosporium*, such as *Chrysosporium lucknowense.*

In an example embodiment, the fiber degrading enzyme blend comprises a cellulolytic composition and a hemicellulolytic composition, wherein the cellulolytic composition comprises two or three polypeptides selected from the group consisting of an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises an arabinofuranosidase and a xylanase.

In an example embodiment, the fiber degrading enzyme blend comprises a cellulolytic composition and a hemicellulolytic composition, wherein the cellulolytic composition comprises two or three polypeptides selected from the group consisting of an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises an arabinofuranosidase and a xylanase, wherein the cellulolytic composition is derived from a strain of *Trichoderma*, such as *Trichoderma reesei*, or a strain of *Humicola*, such as *Humicola insolens*, or a strain of *Chrysosporium*, such as *Chrysosporium lucknowense.*

In an example embodiment, the fiber degrading enzyme blend comprises a cellulolytic composition and a hemicellulolytic composition, wherein the cellulolytic composition comprises:

(i) an *Aspergillus fumigatus* beta-glucosidase disclosed in SEQ ID NO: 8 or a variant thereof with the following substitutions: F100D, S283G, N456E, F512Y having at least 70% identity, at least, 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 8;

(ii) a cellobiohydrolase I (CBH I), such as one derived from a strain of the genus *Aspergillus*, such as a strain of *Aspergillus fumigatus*, such as the CBHI disclosed as SEQ ID NO: 9, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 9; and (iii) an endoglucanase I (EGI), such as one derived from a strain of the genus *Trichoderma*, such as a strain of *Trichoderma reesei*, such as the EGI disclosed as SEQ ID NO: 29, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 29; and wherein the hemicellulolytic composition comprises an arabinofuranosidase and a xylanase.

In an example embodiment, the fiber degrading enzyme blend comprises a cellulolytic composition and a hemicellulolytic composition, wherein the cellulolytic composition comprises an *Aspergillus* beta-glucosidase or a variant thereof; an *Aspergillus* cellobiohydrolase I; and a *Trichoderma* endoglucanase I; and wherein the hemicellulolytic composition comprises an GH10 arabinofuranosidase and a GH10 xylanase.

In an example embodiment, the fiber degrading enzyme blend comprises a cellulolytic composition and a hemicellulolytic composition, wherein the cellulolytic composition comprises an *Aspergillus* beta-glucosidase or a variant thereof; an *Aspergillus* cellobiohydrolase I; and a *Trichoderma* endoglucanase I; and wherein the hemicellulolytic composition comprises a *Talaromyces* GH10 arabinofuranosidase and a *Talaromyces* GH10 xylanase.

In an example embodiment, the fiber degrading enzyme blend comprises a cellulolytic composition and a hemicellulolytic composition, wherein the cellulolytic composition comprises an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises an GH10 arabinofuranosidase and a GH10 xylanase.

In an example embodiment, the fiber degrading enzyme blend comprises a cellulolytic composition and a hemicellulolytic composition, wherein the cellulolytic composition comprises an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises a *Talaromyces pinophilus* GH10 arabinofuranosidase and a *Talaromyces leycettanus* GH10 xylanase.

In an example embodiment, the fiber degrading enzyme blend comprises a *Trichoderma* cellulolytic composition and a hemicellulolytic composition, wherein the cellulolytic composition comprises an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises a *Talaromyces pinophilus* GH10 arabinofuranosidase and a *Talaromyces leycettanus* GH10 xylanase.

In an example embodiment, the fiber degrading enzyme blend comprises a *Trichoderma reesei* cellulolytic composition and a hemicellulolytic composition, wherein the cellulolytic: composition comprises an *Aspergillus fumigatus* beta-glucosidase or a variant thereof; an *Aspergillus fumigatus* cellobiohydrolase I; and a *Trichoderma reesei* endoglucanase I; and wherein the hemicellulolytic composition comprises a *Talaromyces pinophilus* GH10 arabinofuranosidase and a *Talaromyces leycettanus* GH10 xylanase.

In an example embodiment, the fiber degrading enzyme blend comprises a *Trichoderma reesei* cellulolytic composition and a hemicellulolytic composition, wherein the cellulolytic composition comprises:

(i) an *Aspergillus fumigatus* beta-glucosidase disclosed in SEQ ID NO: 8 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 8;

(ii) a cellobiohydrolase I (CBH I), such as one derived from a strain of the genus *Aspergillus*, such as a strain of *Aspergillus fumigatus*, such as the CBHI disclosed as SEQ ID NO: 9, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 9; and (iii) an endoglucanase I (EGI), such as one derived from a strain of the genus *Trichoderma*, such as a strain of *Trichoderma reesei*, such as the EGI disclosed as SEQ ID NO: 29, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 29; and wherein the hemicellulolytic composition comprises:

(i) a GH10 xylanase, such as one derived from a strain of the genus *Talaromyces*, such as a strain of *Talaromyces leycettanus*, such as the one disclosed as SEQ ID NO: 59, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 59; and (ii) a GH62 arabinofuranosidase, such as one derived from a strain of the genus *Talaromyces*, such as a strain of *Talaromyces pinophilus*, such as the one disclosed as SEQ ID NO: 60, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 60.

The fiber degrading enzyme blend can be used in saccharification, fermentation, or simultaneous saccharification and fermentation together with one or more additional enzymes. Any enzyme described herein for use in saccharification, fermentation, of SSF can be used in combination with the fiber degrading enzyme blend.

In an embodiment, any of the fiber degrading enzyme blends above further comprises a glucoamylase. Any glucoamylase described herein is contemplated for inclusion in the fiber degrading enzyme blends described herein.

In an embodiment, any of the fiber degrading enzyme blends above further comprises a trehalase. Any trehalase described herein is contemplated for inclusion in the fiber degrading enzyme blends described herein.

In an embodiment, any of the fiber degrading enzyme blends above further comprises an alpha-amylase. Any alpha-amylase described herein is contemplated for inclusion in the fiber degrading enzyme blends described herein.

In an embodiment, the fiber degrading enzyme blend further comprises a glucoamylase or glucoamylase blend. In an embodiment, the fiber degrading enzyme blend comprises the glucoamylase of SEQ ID NO: 13, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 13.

In an embodiment, the fiber degrading enzyme blend comprises a glucoamylase blend, the glucoamylase blend comprising the glucoamylase of SEQ ID NO: 13, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 13, and a trehalase wherein the trehalase is the trehalase of SEQ ID NO: 12, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 12, or the trehalase is SEQ ID NO: 28 or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 28.

In an embodiment, the fiber degrading enzyme blend comprises a glucoamylase blend, the glucoamylase blend comprising a glucoamylase, a trehalase and an alpha-amylase, wherein the glucoamylase is the glucoamylase of SEQ ID NO: 13, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 13, wherein the trehalase is the trehalase of SEQ ID NO: 12, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 12, or the trehalase is SEQ ID NO: 28 or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 28, and wherein the alpha-amylase is the *Rhizomucor pusillus* alpha-amylase with *Aspergillus niger* glucoamylase linker and SBD disclosed as SEQ ID NO: 11 with the following substitutions: G128D+D143N (activity ratio AGU:AGU:FAU(F): approx. 30:7:1) or one having at least 60%, at least 65%, at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 11.

Polypeptides Having Cellulase Activity

Aspects described herein relate to polypeptide having cellobiohydrolase activity, endoglucanase activity, or beta-glucosidase activity. The present disclosure contemplates processes and enzyme blends or compositions comprising any polypeptides polypeptide having cellobiohydrolase activity, endoglucanase activity, or beta-glucosidase activity that when used alone, or in combination with each other or other enzymes or compositions described herein (e.g., cellulases/cellulolytic composition) result in an improvement in fermentation product yield (e.g., ethanol yield) compared to similar processes and/or enzyme blends or compositions lacking the polypeptides having cellobiohydrolase activity, endoglucanase activity, or beta-glucosidase activity.

Any polypeptide having polypeptide having cellobiohydrolase activity, endoglucanase activity, or beta-glucosidase activity described herein is also contemplated for expression by a fermenting organism or host cell.

In some embodiments, the present invention relates to isolated or purified polypeptides having a sequence identity of at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% or 100% identity to the mature polypeptide of SEQ ID NO: 1, which have cellobiohydrolase activity. In an aspect, the polypeptides differ by up to 10 amino acids, e.g., 1, 2, 3, 4, 5, 6, 7, 8, 9, or 10, from the mature polypeptide of SEQ ID NO: 1. The polypeptide preferably comprises, consists of, or consists essentially of the amino acid sequence of SEQ ID NO: 1 or the mature polypeptide thereof; or is a fragment thereof having cellobiohydrolase activity. In one aspect, the mature polypeptide is amino acids 19-520 of SEQ ID NO: 1.

In some embodiments, the present invention relates to isolated or purified polypeptides having a sequence identity of at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% or 100% identity to the mature polypeptide of SEQ ID NO: 2, which have cellobiohydrolase activity. In an aspect, the polypeptides differ by up to 10 amino acids, e.g., 1, 2, 3, 4, 5, 6, 7, 8, 9, or 10, from the mature polypeptide of SEQ ID NO: 2. The polypeptide preferably comprises, consists of, or consists essentially of the amino acid sequence of SEQ ID NO: 2 or the mature polypeptide thereof; or is a fragment thereof having cellobiohydrolase activity. In one aspect, the mature polypeptide is amino acids 1-503 of SEQ ID NO: 2.

In some embodiments, the present invention relates to isolated or purified polypeptides having a sequence identity of at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% or 100% identity to the mature polypeptide of SEQ ID NO: 3, which have cellobiohydrolase activity. In an aspect, the polypeptides differ by up to 10 amino acids, e.g., 1, 2, 3, 4, 5, 6, 7, 8, 9, or 10, from the mature polypeptide of SEQ ID NO: 3. The polypeptide preferably comprises, consists of, or consists essentially of the amino acid sequence of SEQ ID NO: 3 or the mature polypeptide thereof; or is a fragment thereof having cellobiohydrolase activity. In one aspect, the mature polypeptide is amino acids 26-533 of SEQ ID NO: 3.

In some embodiments, the present invention relates to isolated or purified polypeptides having a sequence identity of at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% or 100% identity to the mature polypeptide of SEQ ID NO: 4, which have cellobiohydrolase activity. In an aspect, the polypeptides differ by up to 10 amino acids, e.g., 1, 2, 3, 4, 5, 6, 7, 8, 9, or 10, from the mature polypeptide of SEQ ID NO: 4. The polypeptide preferably comprises, consists of, or consists essentially of the amino acid sequence of SEQ ID NO: 4 or the mature polypeptide thereof; or is a fragment thereof having cellobiohydrolase activity. In one aspect, the mature polypeptide is amino acids 20-456 of SEQ ID NO: 4.

In some embodiments, the present invention relates to isolated or purified polypeptides having a sequence identity of at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% or 100% identity to the mature polypeptide of SEQ ID NO: 5, which have endoglucanase activity. In an aspect, the polypeptides differ by up to 10 amino acids, e.g., 1, 2, 3, 4, 5, 6, 7, 8, 9, or 10, from the mature polypeptide of SEQ ID NO: 5. The polypeptide preferably comprises, consists of, or consists essentially of the amino acid sequence of SEQ ID NO: 5 or the mature polypeptide thereof; or is a fragment thereof having endoglucanase activity. In one aspect, the mature polypeptide is amino acids 20-410 of SEQ ID NO: 5.

In some embodiments, the present invention relates to isolated or purified polypeptides having a sequence identity of at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% or 100% identity to the mature polypeptide of SEQ ID NO: 1, which have beta-glucosidase activity. In an aspect, the polypeptides differ by up to 10 amino acids, e.g., 1, 2, 3, 4, 5, 6, 7, 8, 9, or 10, from the mature polypeptide of SEQ ID NO: 6. The polypeptide preferably comprises, consists of, or consists essentially of the amino acid sequence of SEQ ID NO: 6 or the mature polypeptide thereof; or is a fragment thereof having beta-glucosidase activity. In one aspect, the mature polypeptide is amino acids 19-520 of SEQ ID NO: 6.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Trichoderma, Lecanicillium, Simplicillium, Aspergillus, Cornyascus, Acrophialophora, Rhinocladiella, Nemania, Talaromyces, Collariella, Rigidoporous*, and/or *Loramyces* cell.

In another aspect, the cell is a *Trichoderma harzianum, Trichoderma atroviride, Trichoderma reesei, Lecanicillium primulinum, Simplicillium lameillicola, Aspergillus nidulans, Aspergillus wentii, Cornyascus sepedonium, Acrophialophora fusispora, Rhinocladiella* sp., *Nemania serpens, Talaromyces leycettanus, Collariella virescens, Rigidoporous* sp. 74222, and/or *Loramyces macrosporus* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid-state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the fermentation medium by conventional procedures including, but not limited to, collection, centrifugation, filtration, extraction, spray-drying, evaporation, or precipitation. In one aspect, a whole fermentation broth comprising the polypeptide is recovered.

The polypeptide may be polypeptide by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

The invention may further be described in the following numbered paragraphs:

Paragraph [1]. A process for producing a fermentation product, such as ethanol, from starch-containing material, the process comprising the steps of:

i) saccharifying the starch-containing material at a temperature below the initial gelatination temperature; and
ii) fermenting the saccharified starch-containing material using a fermenting organism;

wherein at least one polypeptide having cellobiohydrolase activity, endoglucanase activity, or beta-glucosidase activity is present or added during fermentation.

Paragraph [2]. A process for producing a fermentation product, such as ethanol, from starch-containing material, the process comprising the steps of:

i) liquefying the starch-containing material at a temperature above the initial gelatinization temperature using an alpha-amylase;
ii) saccharifying the liquefied starch-containing;
iii) fermenting saccharified starch-containing material using a fermenting organism;

wherein at least one polypeptide having cellobiohydrolase activity, endoglucanase activity, or beta-glucosidase activity is present or added during fermentation.

Paragraph [3]. The process of any of paragraphs [1] or [2], wherein at least one polypeptide having cellobiohydrolase activity is present or added during fermentation or simultaneous saccharification and fermentation.

Paragraph [4]. The process of any of paragraphs [1] or [2], wherein at least one polypeptide having endoglucanase activity is present or added during fermentation or simultaneous saccharification and fermentation.

Paragraph [5]. The process of any of paragraphs [1] or [2], wherein at least one polypeptide having beta-glucosidase activity is present or added during fermentation or simultaneous saccharification and fermentation.

Paragraph [6]. The process of any of paragraphs [1] to [5], wherein the at least one polypeptide having cellobiohydrolase activity, endoglucanase activity, or beta-glucosidase activity comprises at least one, at least two, at least three, at least four, at least five polypeptides, or at least six polypeptides selected from the group consisting of:

(i) the mature polypeptide of SEQ ID NO: 1, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, or at least 99% identity to SEQ ID NO: 1;

(ii) the mature polypeptide of SEQ ID NO: 2, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 2;

(iii) the mature polypeptide of SEQ ID NO: 3, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 3;

(iv) the mature polypeptide of SEQ ID NO: 4, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 4;

(v) the mature polypeptide of SEQ ID NO: 5, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 5; and (vi) the mature polypeptide of SEQ ID NO: 6, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 6.

Paragraph [7]. The process of any of paragraphs [1] to [6], wherein the at least one polypeptide having cellobiohydrolase activity, endoglucanase activity, or beta-glucosidase activity comprises or consists of SEQ ID NO: 1, SEQ ID NO: 2, SEQ ID NO: 3, SEQ ID NO: 4, SEQ ID NO: 5, SEQ ID NO: 6, or the mature polypeptide of SEQ ID NO: 1, SEQ ID NO: 2, SEQ ID NO: 3, SEQ ID NO: 4, SEQ ID NO: 5, SEQ ID NO: 6.

Paragraph [8]. The process of any one of paragraphs [1] to [7], wherein the mature polypeptide is amino acids 19 to 520 of SEQ ID NO: 1, amino acids 1 to 503 of SEQ ID NO: 2, amino acids 26 to 533 of SEQ ID NO: 3, amino acids 20 to 456 of SEQ ID NO: 4, amino acids 20 to 410 of SEQ ID NO: 5 and amino acids 20 to 855 of SEQ ID NO: 6.

Paragraph [9]. The process of any of paragraphs [1] to [8], wherein the at least one polypeptide having cellobiohydrolase activity, endoglucanase activity, or beta-glucosidase activity is a variant of the mature polypeptide of SEQ ID NO: 1, SEQ ID NO: 2, SEQ ID NO: 3, SEQ ID NO: 4, SEQ ID NO: 5, SEQ ID NO: 6 comprising a substitution, deletion, and/or insertion at one or more (e.g., several) positions.

Paragraph [10]. The process of any of paragraphs [1] to [8], wherein the at least one polypeptide having cellobiohydrolase activity, endoglucanase activity, or beta-glucosidase activity is a fragment of SEQ ID NO: 1, SEQ ID NO: 2, SEQ ID NO: 3, SEQ ID NO: 4, SEQ ID NO: 5, SEQ ID NO: 6, wherein the fragment has cellobiohydrolase activity, endoglucanase activity, or beta-glucosidase activity.

Paragraph [11]. The process of any of paragraphs [1] to [10], wherein the at least one polypeptide having cellobiohydrolase activity, endoglucanase activity, or beta-glucosidase activity are dosed in the range 0.1-1000 micro gram EP/g DS; 0.5-500 micro gram EP/g DS; 1-100 micro gram EP/g DS; such as 5-50 micro gram EP/g DS.

Paragraph [12]. The process of any of paragraphs [1] to [11], wherein saccharification and/or fermentation is performed in the presence of at least one additional cellulase in the form of a cellulolytic composition, for example, a cellulolytic composition that comprises the at least one polypeptide and the at least one additional cellulase.

Paragraph [13]. The process of paragraph [12], wherein the cellulolytic composition is derived from a strain of *Trichoderma*, such as *Trichoderma reesei*, or a strain of *Humicola*, such as *Humicola insolens*, or a strain of *Chrysosporium*, such as *Chrysosporium lucknowense*.

Paragraph [14]. The process of paragraph or [13], wherein the cellulolytic composition comprises two or three polypeptides selected from the group consisting of:

beta-glucosidase;

cellobiohydrolase I; and endoglucanase I.

Paragraph [15]. The process of any one of paragraphs to [14], wherein the cellulolytic composition comprises two or three of the following components:

(i) an *Aspergillus fumigatus* beta-glucosidase or a variant thereof;

(ii) an *Aspergillus fumigatus* cellobiohydrolase I; and (iii) a *Trichoderma reesei* endoglucanase I.

Paragraph [16]. The process of any one of paragraphs to [15], wherein the cellulolytic composition is a *Trichoderma reesei* cellulolytic composition further comprising:

(i) an *Aspergillus fumigatus* beta-glucosidase disclosed in SEQ ID NO: 8 or a variant thereof with the following substitutions: F100D, S283G, N456E, F512Y having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity; at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 8;

(ii) a cellobiohydrolase I (CBH I), such as one derived from a strain of the genus *Aspergillus*, such as a strain of *Aspergillus fumigatus*, such as the CBHI disclosed as SEQ ID NO: 9, or a CBHI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 9; and (iii) an endoglucanase I (EGI), such as one derived from a strain of the genus *Trichoderma*, such as a strain of

*Trichoderma reesei*, such as the EGI disclosed as SEQ ID NO: 29, or an EGI having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 29.

Paragraph [17]. The process of any of paragraphs to [16], wherein saccharification and/or fermentation is performed in the presence of a hemicellulolytic composition comprising a xylanase and an arabinofuranosidase.

Paragraph [18]. The process of any of paragraphs to [17], wherein the hemicellulolytic composition comprises:

(i) a GH10 xylanase; and (ii) a GH62 arabinofuranosidase.

Paragraph [19]. The process of any one of paragraphs to [18], wherein the hemicellulolytic composition comprises:

(i) a GH10 xylanase from *Talaromyces leycettanus*; and (ii) a GH62 arabinofuranosidase from *Talaromyces pinophilus*.

Paragraph [20]. The process of any one of paragraphs to [19], wherein the hemicellulolytic composition comprises:

(i) a GH10 xylanase, such as one derived from a strain of the genus *Talaromyces*, such as a strain of *Talaromyces leycettanus*, such as the one disclosed as SEQ ID NO: 59, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 59; and (ii) a GH62 arabinofuranosidase, such as one derived from a strain of the genus *Talaromyces*, such as a strain of *Talaromyces pinophilus*, such as the one disclosed as SEQ ID NO: 60, or one having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 60.

Paragraph [21]. The process of any one of paragraphs to [20], wherein saccharification and/or fermentation is performed in the presence of the cellulolytic composition of any one of paragraphs to and the hemicellulolytic composition of any one of paragraphs to [20].

Paragraph [22]. The process of any of paragraphs [2] to [21], wherein liquefaction is performed in the presence of a protease having a thermostability value of more than 20% determined as Relative Activity at 80° C./70° C.

Paragraph [23]. The process of any of paragraphs [2] to [22], wherein liquefaction is performed in the presence of a glucoamylase.

Paragraph [24]. The process of any of paragraphs [1] to [23], wherein the carbohydrate-source generating enzyme(s) is at least a glucoamylase and optionally in combination with a fungal acid alpha-amylase.

Paragraph [25]. The process of any of paragraphs [1] toi [24], wherein the fermentation product is an alcohol, preferably ethanol, especially fuel ethanol, potable ethanol and/or industrial ethanol.

Paragraph [26]. The process of any of paragraphs [2] to [25], wherein the alpha-amylase is a bacterial or fungal alpha-amylase.

Paragraph [27]. The process of any of paragraphs [2] to [26], wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 14, or alpha-amylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 30.

Paragraph [28]. The process of paragraph [27], wherein the *Bacillus stearothermophilus* alpha-amylase comprises a deletion of two amino acids in the region corresponding to positions 179-182 using SEQ ID NO: 14 for numbering.

Paragraph [29]. The process of paragraph [28], wherein the deletion is selected from the group consisting of 179*+180*, 179*+181*, 179*+182*, 180*+181*, 180*+182*, and 181*+182*, particularly I181*+G182*.

Paragraph [30]. The process according to any of paragraphs [2] to [29], wherein the alpha-amylase. comprises a substitution N193F using SEQ ID NO: 14 for numbering.

Paragraph [31]. The process of any of paragraphs to wherein the *Bacillus stearothermophilus* alpha-amylase has a substitution in position S242, preferably S242Q substitution using SEQ ID NO: 14 for numbering.

Paragraph [32]. The process of any of paragraphs to [31], wherein the *Bacillus stearothermophilus* alpha-amylase has a substitution in position E188, preferably E188P substitution using SEQ ID NO: 14 for numbering.

Paragraph [33]. The process of any of paragraphs [2] to [32], wherein the alpha-amylase has a T½ (min) at pH 4.5, 85° C., 0.12 mM $CaCl_2$)) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

Paragraph [34]. The process of any of paragraphs [2] to [33], wherein the alpha-amylase is selected from the following group of *Bacillus stearothermophilus* alpha-amylase variants (using SEQ ID NO: 14 for numbering):

I181*+G182*+N193F+E129V+K177L+R179E;
I181*+G182*+N193F+V59A+Q89R+E129V+K177L+R179E+H208Y+K220P+N224L+Q254S
I181*+G182*+N193F+V59A+Q89R+E129V+K177L+R179E+Q254S+M284V;
I181*+G182*+N193F+V59A+E129V+K177L+R179E+Q254S+M284V;
I181*+G182*+N193F+E129V+K177L+R179E+K220P+N224L+S242Q+Q254S;
I181*+G182*+V59A+E129V+K177L+R179E+Q254S+M284V+V212T+Y268G+N293Y+T297N;
I181*+G182*+V59A+E129V+K177L+R179E+Q254S+M284V+V212T+Y268G+N293Y+T297N+S173N+E188P+H208Y+S242Y+K2791;
I181*+G182*+V59A+E129V+K177L+R179S+Q254S+M284V+V212T+Y268G+N293Y+T297N+A184Q+E188P+T191N
I181*+G182*+V59A+E129V+K177L+R179S+Q254S+M284V+V212T+Y268G+N293Y+T297N+A184Q+E188P+T191N+S242Y+K2791;
I181*+G182*+V59A+E129V+K177L+R179E+Q254S+M284V+V212T+Y268G+N293Y+T297N+E188P+K279W;
I181*+G182*+V59A+E129V+K177L+R179E+Q254S+M284V+V212T+Y268G+N293Y+T297N+W115D+D117Q+T133P; and wherein the variant has at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 14.

Paragraph [35]. The process of any of paragraphs [2] to [34], wherein a protease with a thermostability value of more than 25% determined as Relative Activity at 80° C./70° C. is present in liquefaction step i).

Paragraph [36]. The process of paragraph [35], wherein the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

Paragraph [37]. The process of paragraph or [36], wherein the protease has a thermostability of between 20% and 50%, such as between 20% and 40%, such as 20% and 30% determined as Relative Activity at 80° C./70° C.

Paragraph [38]. The process of any of paragraphs to [37], wherein the protease has a thermostability between 50% and 115%, such as between 50% and 70%, such as between 50% and 60%, such as between 100% and 120%, such as between 105% and 115% determined as Relative Activity at 80° C./70° C.

Paragraph [39]. The process of any of paragraphs to [38], wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

Paragraph [40]. The process of any of paragraphs to [39], wherein the protease has thermostability of between 10% and 50%, such as between 10% and 30%, such as between 10% and 25% determined as Relative Activity at 85° C./70° C.

Paragraph [41]. The process of any of paragraphs to [40], wherein the protease has a thermostability above 60%, such as above 90%, such as above 100%, such as above 110% at 85° C. as determined using the Zein-BCA assay.

Paragraph [42]. The process of any of paragraphs to [41], wherein the protease has a thermostability between 60-120, such as between 70-120%, such as between 80-120%, such as between 90-120%, such as between 100-120%, such as 110-120% at 85° C. as determined using the Zein-BCA assay.

Paragraph [43]. The process of any of paragraphs to [42], wherein the protease is of fungal or bacterial origin.

Paragraph [44]. The process of any of paragraphs to [43], wherein the protease is a metallo protease or a serine protease.

Paragraph [45]. The process of paragraph [44], wherein the protease is a variant of the metallo protease derived from a strain of the genus *Thermoascus*, preferably a strain of *Thermoascus aurantiacus*, especially *Thermoascus aurantiacus* CGMCC No. 0670.

Paragraph [46]. The process of paragraph [45], wherein the protease is a variant of the metallo protease disclosed as SEQ ID NO: 15 with the following mutations:

D79L+S87P+A112P+D142L;
D79L+S87P+D142L; or
A27K+D79L+Y82F+S87G+D104P+A112P+A126V+D142L; and wherein the protease has at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 15.

Paragraph [47]. The process of paragraph [45], wherein the protease is a serine protease, particularly an S8 serine protease derived from a strain of *Pyrococcus*, preferably a strain of *Pyrococcus furiosus*, or derived from a strain of *Thermococcus*, preferably *Thermococcus thioreducens* or *Thermococcus* nautili, or derived from a strain of *Palaeococcus*, preferably *Palaeococcus ferrophilus*.

Paragraph [48]. The process of paragraph [47], wherein the protease is derived from a strain of *Pyrococcus*, preferably a strain of *Pyrococcus furiosus*.

Paragraph [49]. The process of paragraph [48], wherein the protease is the one shown in SEQ ID NO: 16, or a protease having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 16.

Paragraph [50]. The process of any of paragraphs to [49], wherein the protease is derived from a strain of *Thermobifida*, preferably a strain of *Thermobifida cellulosytica.*

Paragraph [51]. The process of paragraph [50], wherein the protease is the one shown in SEQ ID NO: 18, or a protease having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 18.

Paragraph [52]. The process of any of paragraphs [1] to [51], wherein a glucoamylase is present and/or added during saccharification and/or fermentation.

Paragraph [53]. The process of paragraph [52], wherein the glucoamylase present and/or added during saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *Talaromyces emersonii*, or a strain of *Trametes*, preferably *Trametes cingulata*, or a strain of *Pycnoporus*, or a strain of *Gloeophyllum*, such as a strain of *Gloeophyllum sepiarium* or *Gloeophyllum trabeum* or a strain of the *Nigrofomes.*

Paragraph [54]. The process of paragraphs or [53], wherein the glucoamylase present and/or added during saccharification and/or fermentation is a blend comprising *Talaromyces emersonii* glucoamylase of SEQ ID NO: 27, or glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 27, a *Trametes cingulata* glucoamylase of SEQ ID NO: 24, or glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 24, and a *Rhizomucor pusillus* alpha-amylase with an *Aspergillus niger* glucoamylase linker and starch-binding domain (SBD), of SEQ ID NO: 11, and comprising the following substitutions: G128D+D143N, and having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 40.

Paragraph [55]. The process of any of paragraphs to [54], wherein the glucoamylase present and/or added during saccharification and/or fermentation is a blend comprising *Gloeophyllum sepiarium* glucoamylase shown as SEQ ID NO: 13, or a glucoamylase having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 13, and an alpha-amylase from *Rhizomucor pusillus* with an *Aspergillus niger* glucoamylase linker and starch-binding domain (SBD), disclosed SEQ ID NO: 11 with the following substitutions: G128D+D143N, and having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 40.

Paragraph [56]. The process of any one of paragraphs [1] to [55], wherein a trehalase is present and/or added during saccharification and/or fermentation.

Paragraph [57]. The process of paragraph [56], wherein the trehalase present and/or added during saccharification and/or fermentation is a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the mature polypeptide of SEQ ID NO: 12 and having trehalase activity.

Paragraph [58]. The process of paragraph [56], wherein the trehalase present and/or added during saccharification and/or fermentation is a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to the mature polypeptide of SEQ ID NO: 28 and having trehalase activity.

Paragraph [59]. The process of any of paragraphs [1] to [58], wherein saccharification and fermentation are carried out sequentially or simultaneously.

Paragraph [60]. The process of any of paragraphs [1] to [59], wherein fermentation or simultaneous saccharification and fermentation (SSF) are carried out at a temperature from 25° C. to 40° C., such as from 28° C. to 35° C., such as from 30° C. to 34° C., preferably around about 32° C.

Paragraph [61]. The process of any of paragraphs [1] to [60], wherein the fermentation product is recovered after fermentation, such as by distillation.

Paragraph [62]. The process of any of paragraphs [1] to [61], wherein the starch-containing starting material is whole grains.

Paragraph [63]. The process of any of paragraphs [1] to [62], wherein the starch-containing material is derived from corn, wheat, barley, rye, milo, sago, cassava, manioc, tapioca, sorghum, rice or potatoes.

Paragraph [64]. The process of any of paragraphs [1] to [63], wherein the organism applied in fermentation is a yeast, particularly a *Saccharomyces* spp., more particular *Saccharomyces cerevisiae.*

Paragraph [65]. An isolated polypeptide having cellobiohydrolase activity, endoglucanase activity, or beta-glucosidase activity selected from the group consisting of:

- (i) the mature polypeptide of SEQ ID NO: 1, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, or at least 99% identity to SEQ ID NO: 1;
- (ii) the mature polypeptide of SEQ ID NO: 2, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 2;
- (iii) the mature polypeptide of SEQ ID NO: 3, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 3;
- (iv) the mature polypeptide of SEQ ID NO: 4, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 4;
- (v) the mature polypeptide of SEQ ID NO: 5, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 5; and
- (vi) the mature polypeptide of SEQ ID NO: 6, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 6.

Paragraph [66]. The polypeptide of paragraph [65], wherein the amino acid sequence comprises or consists of SEQ ID NO: 1, SEQ ID NO: 2, SEQ ID NO: 3, SEQ ID NO: 4, SEQ ID NO: 5, SEQ ID NO: 6, or the mature polypeptide of SEQ ID NO: 1, SEQ ID NO: 2, SEQ ID NO: 3, SEQ ID NO: 4, SEQ ID NO: 5, SEQ ID NO: 6.

Paragraph [67]. The polypeptide of paragraph or [66], wherein the mature polypeptide is amino acids 19 to 520 of SEQ ID NO: 1, amino acids 1 to 503 of SEQ ID NO: 2, amino acids 26 to 533 of SEQ ID NO: 3, amino acids 20 to 456 of SEQ ID NO: 4, amino acids 20 to 410 of SEQ ID NO: 5 and amino acids 20 to 855 of SEQ ID NO: 6.

Paragraph [68]. The polypeptide of paragraph [65], which is a variant of the mature polypeptide of SEQ ID NO: 1, SEQ ID NO: 2, SEQ ID NO: 3, SEQ ID NO: 4, SEQ ID NO: 5, SEQ ID NO: 6 comprising a substitution, deletion, and/or insertion at one or more (e.g., several) positions.

Paragraph [69]. The polypeptide of paragraph [65], which is a fragment of SEQ ID NO: 1, SEQ ID NO: 2, SEQ ID NO: 3, SEQ ID NO: 4, SEQ ID NO: 5, SEQ ID NO: 6, wherein the fragment has cellobiohydrolase activity, endoglucanase activity, or beta-glucosidase activity.

Paragraph [70]. An enzyme blend or enzyme composition comprising at least one polypeptide having cellobiohydrolase activity, endoglucanase activity, or beta-glucosidase activity of any one of paragraphs to [70].

Paragraph [71]. The blend or composition of paragraph [70], further comprising a carbohydrate-source generating enzyme, particularly a glucoamylase.

Paragraph [72]. The blend or composition of paragraph or [71], further comprising a cellulase/cellulolytic composition comprising a beta-glucosidase, a cellobiohydrolase and an endoglucanase.

Paragraph [73]. The blend or composition of paragraph [72], wherein the cellulases/cellulolytic composition comprises one or more polypeptides selected from the group consisting of:

GH61 polypeptide having cellulolytic enhancing activity, beta-glucosidase;

Cellobiohydrolase I;

Cellobiohydrolase II;

or a mixture of two, three, or four thereof.

Paragraph [74]. The blend or composition of paragraph or [73], wherein the cellulases/cellulolytic composition comprises one or more of the following components:

(i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof; and (iv) a *Penicillium* sp. GH61 polypeptide having cellulolytic enhancing activity; or homologs thereof.

Paragraph [75]. The blend or composition of any one of paragraphs to [74], further comprising a trehalase.

Paragraph [76]. An isolated polynucleotide encoding the polypeptide of any of paragraphs to [69].

Paragraph [77]. A nucleic acid construct or expression vector comprising the polynucleotide of paragraph operably linked to one or more control sequences that direct the production of the polypeptide in an expression host.

Paragraph [78]. A recombinant host cell comprising the polynucleotide of paragraph operably linked to one or more control sequences that direct the production of the polypeptide.

Paragraph [79]. A method of producing a polypeptide having cellobiohydrolase activity, endoglucanase activity, or beta-glucosidase activity, comprising:

(a) cultivating the host cell of paragraph under conditions conducive for production of the polypeptide; and (b) recovering the polypeptide.

Paragraph [80]. A transgenic plant, plant part or plant cell transformed with a polynucleotide encoding the polypeptide of any of paragraphs to [69].

Paragraph [81]. A method of producing a polypeptide having cellobiohydrolase activity, endoglucanase activity, or beta-glucosidase activity, comprising:

(a) cultivating the transgenic plant or plant cell of paragraph under conditions conducive for production of the polypeptide; and (b) recovering the polypeptide.

Paragraph [82]. A method of producing a mutant of a parent cell, comprising inactivating a polynucleotide encoding the polypeptide of any of paragraphs to [69], which results in the mutant producing less of the polypeptide than the parent cell.

Paragraph [83]. A mutant cell produced by the method of paragraph [82].

Paragraph [84]. A method of producing a protein, comprising:

(a) cultivating the mutant cell of paragraph under conditions conducive for production of the protein; and (b) recovering the protein.

Paragraph [85]. A recombinant host cell comprising at least one heterologous polynucleotide encoding a polypeptide having cellobiohydrolase activity, endoglucanase activity, or beta-glucosidase activity selected from the group consisting of:

(i) the mature polypeptide of SEQ ID NO: 1, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, or at least 99% identity to SEQ ID NO: 1;

(ii) the mature polypeptide of SEQ ID NO: 2, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 2;

(iii) the mature polypeptide of SEQ ID NO: 3, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 3;

(iv) the mature polypeptide of SEQ ID NO: 4, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity or at least 99% identity to SEQ ID NO: 4;

(v) the mature polypeptide of SEQ ID NO: 5, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 5; and (vi) the mature polypeptide of SEQ ID NO: 6, or a polypeptide having at least 70% identity, at least 71% identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO: 6.

Paragraph [86]. The recombinant host cell of paragraph [85], wherein the at least one heterologous polynucleotide encoding a polypeptide having cellobiohydrolase activity, endoglucanase activity, or beta-glucosidase activity comprises or consists of SEQ ID NO: 1, SEQ ID NO: 2, SEQ ID NO: 3, SEQ ID NO: 4, SEQ ID NO: 5, SEQ ID NO: 6, or the mature polypeptide of SEQ ID NO: 1, SEQ ID NO: 2, SEQ ID NO: 3, SEQ ID NO: 4, SEQ ID NO: 5, SEQ ID NO: 6.

Paragraph [87]. The recombinant host cell of paragraphs or [86], wherein the mature polypeptide is amino acids 19 to 520 of SEQ ID NO: 1, amino acids 1 to 503 of SEQ ID NO: 2, amino acids 26 to 533 of SEQ ID NO: 3, amino acids 20 to 456 of SEQ ID NO: 4, amino acids 20 to 410 of SEQ ID NO: 5 and amino acids 20 to 855 of SEQ ID NO: 6.

Paragraph [88]. The recombinant host cell of paragraph [85], wherein the at least one heterologous polynucleotide encoding a polypeptide having cellobiohydrolase activity, endoglucanase activity, or beta-glucosidase activity is a variant of the mature polypeptide of SEQ ID NO: 1, SEQ ID NO: 2, SEQ ID NO: 3, SEQ ID NO: 4, SEQ ID NO: 5, SEQ ID NO: 6 comprising a substitution, deletion, and/or insertion at one or more (e.g., several) positions.

Paragraph [89]. The recombinant host cell of paragraph [85], wherein the at least one heterologous polynucleotide encoding a polypeptide having cellobiohydrolase activity, endoglucanase activity, or beta-glucosidase activity is a fragment of SEQ ID NO: 1, SEQ ID NO: 2, SEQ ID NO: 3, SEQ ID NO: 4, SEQ ID NO: 5, SEQ ID NO: 6, wherein the fragment has cellobiohydrolase activity, endoglucanase activity, or beta-glucosidase activity.

Paragraph [90]. The recombinant host cell of any of paragraphs to [89], wherein the cell further comprises a heterologous polynucleotide encoding a glucoamylase.

Paragraph [91]. The recombinant host cell of paragraph [90], wherein the heterologous polynucleotide encoding the glucoamylase is operably linked to a promoter that is foreign to the polynucleotide.

Paragraph [92]. The recombinant host cell of any of paragraphs to [91], wherein the cell further comprises a heterologous polynucleotide encoding an alpha-amylase.

Paragraph [93]. The recombinant host cell of paragraph [92], wherein the heterologous polynucleotide encoding the alpha-amylase is operably linked to a promoter that is foreign to the polynucleotide.

Paragraph [94]. The recombinant host cell of any of paragraphs to [93], wherein the cell further comprises a heterologous polynucleotide encoding a protease.

Paragraph [95]. The recombinant host cell of paragraph [94], wherein the heterologous polynucleotide encoding the protease is operably linked to a promoter that is foreign to the polynucleotide.

Paragraph [96]. The recombinant host cell of any of paragraphs to [95], wherein the cell further comprises a disruption to an endogenous gene encoding a glycerol 3-phosphate dehydrogenase (GPD).

Paragraph [97]. The recombinant host cell of any of paragraphs to [96], wherein the cell further comprises a disruption to an endogenous gene encoding a glycerol 3-phosphatase (GPP).

Paragraph [98]. The recombinant host cell of any of paragraphs to [97], wherein the cell is a yeast cell.

Paragraph [99]. The recombinant host cell of any of paragraphs to [98], wherein the cell is a *Saccharomyces, Rhodotorula, Schizosaccharomyces, Kluyveromyces, Pichia, Hansenula, Rhodosporidium, Candida, Yarrowia, Lipomyces, Cryptococcus*, or Dekkera sp. cell.

Paragraph [100]. The recombinant host cell of any of paragraphs to [99], wherein the cell is a *Saccharomyces cerevisiae* cell.

Paragraph [101]. A composition comprising the recombinant host cell of any of paragraphs to and one or more naturally occurring and/or non-naturally occurring components, such as components are selected from the group consisting of: surfactants, emulsifiers, gums, swelling agents, and antioxidants.

Paragraph [102]. Use of a recombinant host cell of any of paragraphs to in the production of ethanol.

The invention described and claimed herein is not to be limited in scope by the specific aspects or embodiments herein disclosed, since these aspects/embodiments are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. All references are specifically incorporated by reference for that which is described.

The following examples are offered to illustrate certain aspects/embodiments of the present invention, but not in any way intended to limit the scope of the invention as claimed.

EXAMPLES

Enzymes Used in the Examples:

Alpha-Amylase 369 (AA369): *Bacillus stearothermophilus* alpha-amylase of SEQ ID NO: 14 with the mutations: I181*+G182*+N193F+V59A+Q89R+E129V+K177L+R179E+Q254S+M284V truncated to 491 amino acids.

Protease PfuS: Protease derived from *Pyrococcus furiosus* shown in SEQ ID NO: 16 herein Alpha-amylase blend X: Blend of Amylase AA369 and Protease PfuS.

Trehalase Ms: *Myceliophthora sepedonium* trehalase disclosed herein as SEQ ID NO:28.

Trehalase Tf: *Talaromyces funiculosus* trehalase disclosed herein as SEQ ID NO: 12.

Glucoamylase Blend A: Blend comprising *Gloeophyllum sepiarium* glucoamylase disclosed in SEQ ID NO: 13 and Trehalase Ms.

Glucoamylase Blend B: Blend comprising *Gloeophyllum sepiarium* glucoamylase disclosed in SEQ ID NO: 13, Trehalase Tf and *Rhizomucor pusillus* alpha-amylase with *Aspergillus niger* glucoamylase linker and SBD disclosed as SEQ ID NO: 11 with the following substitutions: G128D+D143N (activity ratio AGU:AGU:FAU(F): approx. 30:7:1).

Cellulolytic Composition: Cellulolytic composition derived from *Trichoderma reesei* comprising *Aspergillus fumigatus* beta-glucosidase (SEQ ID NO: 2 in WO 2005/047499 SEQ ID NO:

8 herein) variant F100D, S283G, N456E, F512Y) disclosed in WO 2012/044915; *Aspergillus fumigatus* Cel7A CBH1 disclosed as SEQ ID NO: 6 in WO2011/057140 (SEQ ID NO: 9 herein) and *Trichoderma reesei* endoglucanase 1 (Tr EG1) disclosed as SEQ ID NO: 29 herein.

GH10 xylanase: *Talaromyces leycettanus* xylanase disclosed herein as SEQ ID NO: 59.

GH62 arabinofuranosidase: *Talaromyces pinophilus* arabinofuranosidase disclosed herein as SEQ ID NO: 60.

Hemicellulolytic Composition: composition comprising GH10 xylanase and GH62 arabinofuranosidase.

Media and Solutions:

The following media or solutions were autoclaved at 121° C. for 20 minutes unless otherwise specified. Chemicals used as buffers and substrates were commercial products of at least reagent grade.

PDA plate was composed of 39 g of potato dextrose agar in a final volume of 1 L with deionized water.

YG plate was composed of 5 g of yeast extract, 10 g of glucose and 20 g of agar, in a final volume 1 L with deionized water.

YPG medium was composed of 0.4% yeast extract, 0.1% $KH_2PO_4$, 0.05% $MgSO_4 \cdot 7H_2O$ and 1.5% glucose in deionized water.

LB medium was composed of 10 g of Bacto-tryptone, 5 g of yeast extract and 5 g of sodium chloride, in a final volume of 1 L with deionized water.

LBA medium (LB+Ampicillin) was prepared by adding 100 mg/ml Ampicillin to LB medium at 1:1000 at room temperature.

LBA plate was prepared by adding 15 g of agar to LB medium in a final volume of 1 L prior autoclaving, and adding 100 mg/ml Ampicillin at 1:1000 when cooling to 60° C.

Minimal medium plate was composed of 342 g of sucrose, 20 g of agar powder and 20 ml of COVE salt solution, in a final volume of 1 L with deionized water. After autoclaving, the medium was then supplemented with 10 ml of 1M Acetamide (filter sterilized) when cooling to 60° C.

COVE salt solution was composed of 26 g of $MgSO_4 \cdot 7H_2O$, 26 g of KCL, 76 g of $KH_2PO_4$ and 50 ml of COVE trace metal solution, in a final volume of 1 L with deionized water.

COVE trace metal solution was composed of 0.04 g of $Na_2B_4O_7 \cdot 10H_2O$, 0.4 g of $CuSO_4 \cdot 5H_2O$, 0.8 g of $FeSO_4 \cdot 7H_2O$, 0.8 g of $MnSO_4 \cdot H_2O$, 0.8 g of $Na_2MoO_4$: $2H_2O$ and 8 g of $ZnSO_4 \cdot 7H_2O$, in a final volume of 1 L with deionized water.

TOP agar medium was composed of 6 g SeaKem GTG agarose, 20 ml of COVE salt solution and 342 g sucrose, in a final volume of 1 L with deionized water. After autoclaving, the medium was then supplemented with 10 ml of 1M Acetamide when cooling to 60° C.

COVE medium reisolation plate was composed of 30 g of sucrose, 20 ml of COVE salt solution and 20 g of agar, in a final volume of 1 L with deionized water. After autoclaving, the medium was then supplemented with 100 μl of Triton X-100 and 10 ml of 1M Acetamide when cooling to 60° C.

COVE medium slant was composed of 30 g of sucrose, 20 ml of COVE salt solution and 20 g of agar, in a final volume up to 1 L with deionized water. After autoclaving, the medium was supplemented with 10 ml of 1M Acetamide when cooling to 60° C.

60% PEG4000 (W/V) was prepared by dissolving 60 g of PEG4000 in 40 ml of deionized water and then adding $CaCl_2$ and Tris/HCl pH7.5 to a final concentration of 10 mM each. The final volume was adjusted to 1 L with deionized water.

DAP4C medium was composed of 0.5 g yeast extract, 10 g maltose, 20 g glucose, 11 g $MgSO_4 \cdot 7H_2O$, 1 g $KH_2PO_4$, 2.2 g Citric acid·$H_2O$, 5.2 g $K_3PO_4 \cdot H_2O$ and 0.5 ml of AMG Trace element solution, in a final volume of up to 1 L with deionized water, dissolving by stirring. Then 400 ml was aliquoted to a shake flask of 2 L. One tablet of 0.5 g Calcium carbonate was added to each flask. After autoclaving, 3.3 ml of 20% lactic acid (autoclaved) and 9.3 ml of 50% $(NH_4)_2HPO_4$ (filter sterilized) were added to each flask.

AMG Trace element solution was composed of 6.8 g $ZnCl_2$, 2.5 g $CuSO_4 \cdot 5H_2O$, 0.24 g $NiCl_2 \cdot 5H_2O$, 13.9 g $FeSO_4 \cdot 7H_2O$, 13.6 g $MnSO_4 \cdot 5H_2O$ and 3 g Citric acid·$H_2O$, in a final volume of 1 L with deionized water.

YPM medium was composed of 10 g of yeast extract, 20 g of peptone and 20 g of maltose, in a final volume 1 L with deionized water.

Strains:

The fungal strain NN053878 was obtained from the Institute of Microbiology, Chinese Academy of Sciences, and identified as *Penicillium swiecickii*, based on both morphological characteristics and ITS rDNA sequence.

The fungal strain NN046799 was isolated from a soil sample collected in China, by dilution plate method with YG medium, pH7, 37° C. The strain was then purified by transferring a single conidium onto a PDA agar plate, and identified as *Talaromyces verruculosus*, based on both morphological characteristics and ITS rDNA sequence.

The fungal strain NN046877 was isolated from a soil sample collected in China, by dilution plate method with YG medium, pH7, 37° C. The strain was then purified by transferring a single conidium onto a PDA agar plate, and identified as *Talaromyces pinophilus*, based on both morphological characteristics and ITS rDNA sequence.

The fungal strain NN058608 was purchased from Centraalbureau voor Schimmelcultures (CBS, Utrecht, Netherlands) with access number of CBS690.92. The strain NN058608 was identified as *Cladosporium antarcticum*, based on both morphological characteristics and ITS rDNA sequence.

*Escherichia coli* Top10 strain was purchased from TIANGEN (TIANGEN Biotech Co. Ltd., Beijing, China) and used to propagate the expression vectors.

*Aspergillus oryzae* strain MT3568 was described in WO2014026630A1.

*Aspergillus oryzae* strain DAu785 was described in WO2018113745.

*Aspergillus oryzae* strain HowB101 was described in WO9535385.

Yeast strain MEJI797 is MBG5012 of WO2019/161227 further expressing a *Pycnopous sanguineus* glucoamylase (SEQ ID NO: 4 of WO2011/066576) and a hybrid *Rhizomucor pusillus* alpha amylase expression cassette (as described in WO2013/006756).

Example 1: Cloning and Identification of *Penicillium swiecickii* CBHI

Genomic DNA Extraction

The *Penicillium swiecickii* strain NN053878 was inoculated onto a PDA plate and incubated for 7 days at 20° C. in darkness. Several mycelia-PDA plugs were inoculated into 500 ml shake flasks containing 100 ml of YPG medium. The flasks were incubated for 4 days at 20° C. with shaking at 160 rpm.

The mycelia were collected by filtration through MIRACLOTH® and frozen under liquid nitrogen. Frozen mycelia were ground, by a mortar and a pestle, to a fine powder, and genomic DNA was isolated using DNeasy® Plant Maxi Kit (24) (QIAGEN GmbH, Hilden, Germany) following the manufacturer's instruction.

Genome Sequencing, Assembly and Annotation

The extracted genomic DNA sample of NN053878 was delivered to Fasteris (Switzerland) for genome sequencing using an ILLUMINA® HiSeq 2000 System (Illumina, Inc., San Diego, CA, USA). The raw reads were assembled at Novozymes Denmark using program Idba (Peng, Yu et al., 2010, *Research in Computational Molecular Biology,* 6044: 426-440. Springer Berlin Heidelberg). The assembled sequences were analyzed using standard bioinformatics methods for gene identification and function prediction. GeneMark-ES fungal version (Ter-Hovhannisyan V et al., 2008, *Genome Research* 18 (12): 1979-1990) was used for gene prediction. Blastall version 2.2.25 (Altschul et al., 1990, *Journal of Molecular Biology,* 215 (3): 403-410) and HMMER version 2.1.1 (National Center for Biotechnology Information (NCBI), Bethesda, MD, USA) were used to predict function based on structural homology. The *Penicillium swiecickii* GH7 cellobiohydrolase I (CBH1) gene was identified directly by analysis of the Blast results. The Agene program (Munch and Krogh, 2006, *BMC Bioinformatics,* 7:263) and SignalP program (Nielsen et al., 1997, *Protein Engineering,* 10:1-6) were used to identify start codons. SignalP program was further used to predict signal peptides. Pepstats (Rice et al., 2000, *Trends Genet,* 16 (6): 276-277) was used to predict isoelectric points and molecular weights.

Cloning of the *Penicillium swiecickii* GH7 CBH1 Gene from Genomic DNA

The above identified *Penicillium swiecickii* GH7 CBH1 gene was cloned to the expression vector pCaHj505 ($EP2748189B_1$) and heterologously expressed in *Aspergillus oryzae* strain MT3568.

| | DNA sequence | Protein sequence |
|---|---|---|
| *Penicillium swiecickii* GH7 CBH1 | SEQ ID NO: 30 | SEQ ID NO: 3 |

Based on the DNA information obtained from genome sequencing, oligonucleotide primers, shown below, were designed to amplify the coding sequences of the *Penicillium swiecickii* GH7 CBH1 gene from the genomic DNA of NN053878. The primers were synthesized by Invitrogen, Beijing, China.

```
Forward Primer:
                                        (SEQ ID NO: 33)
5'-ACACAACTGGGGATCCACCatggcctccactctttc-3'

Reverse Primer:
                                        (SEQ ID NO: 34)
5'-CCCTCTAGATCTCGAGcgccacatggtcataacatcaag-3'
```

Lowercase characters of forward primers represented the coding regions of the genes while lowercase characters of reverse primers represented the complementary downstream flanking regions of the coding sequences of both genes. Bold characters represented a region homologous to insertion sites of pCaHj505. The four letters underlined in the forward primers represented the Kozark sequence as the initiation of translation process.

For the amplification of the *Penicillium swiecickii* GH7 CBH1 gene, 10 μmol of the forward and reverse primers (SEQ ID NOs: 33 and 34) were used in a PCR reaction composed of 2 μl of genomic DNA of NN053878, 10 μl of 5× Phusion® GC Buffer (Finnzymes Oy, Espoo, Finland), 1.5 ul of DMSO, 1 ul of 2.5 mM each of dATP, dTTP, dGTP, and dCTP, and 0.6 unit of PHUSION™ High-Fidelity DNA Polymerase (Finnzymes Oy, Espoo, Finland) and double distilled water to a final volume of 50 μl. The amplification was performed using a Peltier Thermal Cycler (MJ Research Inc., South San Francisco, CA, USA) programmed for denaturing at 94° C. for 3 minutes; 10 cycles of each denaturing at 94° C. for 40 seconds, annealing at 69° C. for 30 seconds, with a 1° C. decrease per cycle and elongation at 72° C. for 2 minutes; then 25 cycles of each at 94° C. for 40 seconds, 59° C. for 40 seconds, and 72° C. for 2 minutes; and a final extension at 72° C. for 7 minutes.

The PCR products were isolated by 1.0% agarose gel electrophoresis using 90 mM Tris-borate and 1 mM EDTA (TBE) buffer where a single product band of ~1.7 kb for the *Penicillium swiecickii* GH7 CBH1 gene were visualized under UV light. The PCR product was then purified from solutions by using the Illustra™ GFX™ PCR DNA and Gel Band Purification Kit (GE Healthcare, Buckinghamshire, UK) according to the manufacturers' instructions.

The plasmid of pCaHj505 was digested with BamHI and XhoI. The linearized vector product was isolated by 1.0% agarose gel electrophoresis using TBE buffer and purified using an ILLUSTRA™ GFX™ PCR DNA and Gel Band Purification Kit.

For cloning, the In-Fusion® HD Cloning Kit (Clontech Laboratories, Inc., Mountain View, CA, USA) was used. Briefly, 0.8 ul of linearized pCaHj505, 3.2 ul of the *Penicillium swiecickii* GH7 CBH1 PCR product were added to 1 ul of 5× In-Fusion mix. Then the ligation reaction solution was incubated at 50° C. for 15 minutes, and kept on ice till *E. coli* transformation.

The ligation reaction solution was used to transform *E. coli* TOP10 competent cells (TIANGEN Biotech Co. Ltd., Beijing, China) following the manufacturers' instructions. 20-30 transformants were obtained. Several *E. coli* transformants were selected and sent for sequencing using 3730XL DNA Analyzers (Applied Biosystems Inc, Foster City, CA, USA) in SinoGenoMax (SinoGenoMax Company Limited, Beijing, China). The one that was confirmed with the right gene insertion and the correct sequence was selected for plasmid DNA preparation. The selected transformants were inoculated to LBA medium and grown at 37° C., 200 rpm, overnight. Plasmid DNA was prepared using a QIAPREP® Spin Miniprep Kit (QIAGEN GmbH, Hilden, Germany). This resulted in plasmid p505-GH7_Pesw, in which transcription of the coding sequence of the *Penicillium swiecickii* GH7 CBH1 gene was under the control of a TAKA-amylase promoter derived from *Aspergillus oryzae*.

Expression of the *Penicillium swiecickii* GH7 CBH1 Gene in *Aspergillus oryzae*

*Aspergillus oryzae* strain MT3568 was used for the heterologous expression of the gene encoding the *Penicillium swiecickii* GH7 CBH1.

Protoplasts of were prepared and transformed according to the method of Christensen et al., 1988, *Bio/Technology* 6:1419-1422.

Plasmid p505-GH7_Pesw was used to transform MT3568. In brief, 3 μg plasmid DNA was added to 100 ul of protoplasts and after incubation at room temperature for 10 minutes, 300 ul of 60% PEG was added and mixed with protoplasts. Then after another 30 minutes incubation at room temperature, protoplasts were resuspended in ~6 ml of top agar medium and spread onto the Minimal medium plate. The plate was incubated at 37° C. until transformants were visible and started to sporulate.

The transformation yielded about 20 transformants. Four transformants were isolated on COVE medium reisolation plates and were then inoculated separately into 3 ml of YPM medium in 24-well deep well plate and incubated at 30° C., 150 rpm. After 3 days incubation, 20 ul of supernatant from the culture was analyzed on NUPAGER NOVEX® 4-12% Bis-Tris Gel with 50 mM MES (Invitrogen Corporation, Carlsbad, CA, USA) according to the manufacturer's instructions. The resulting gel was stained with INSTANTBLUE™ (Expedeon Ltd., Babraham Cambridge, UK). SDS-PAGE profiles of the cultures showed that the majority of the transformants had a major band of approximately ~56 kDa for the *Penicillium swiecickii* GH7 CBH1. The expression strain was then designated O62JNC.

Fermentation of *Aspergillus oryzae* Expression Strains 062JNC

Two fully sporulated slants of the expression strain O62JNC were each washed with 5 ml of DAP4C and inoculated into 14 2-liter flasks each containing 400 ml of DAP4C medium, shaking at 30° C., 80 rpm. The culture broths were harvested on day 3 and filtered by using a 1000 ml Rapid-Flow Bottle Top Filter 0.2 um aPES membrane (ThermoFisher Scientific, Waltham, Massachusetts, USA). The filtered broth sample was purified as described below.

Purification of Recombinant *Penicillium swiecickii* CBHI from *Aspergillus oryzae* 062JNC A 5600 ml volume of filtered supernatant of *Aspergillus oryzae* O62JNC was precipitated with ammonium sulfate (80% saturation), the protein was re-dissolved in $ddH_2O$, followed by adjusting conductivity to 145 ms/cm with $(NH_4)_2SO_4$, and filtered through a 0.45 μm filter. The final volume was 130 ml. The solution was applied to a 40 ml Phenyl Sepharose high performance column (GE Healthcare, Buckinghamshire, UK), protein was washed with a linear 1.2-0 M $(NH_4)_2SO_4$ gradient.

Fractions were analyzed by SDS-PAGE using a NUPAGE® NOVEX® 4-12% Bis-Tris Gel with 50 mM MES. The resulting gel was stained with INSTANTBLUE™. Fractions containing a band at approximately 56 kDa were pooled. Then the pooled solution was concentrated by ultrafiltration.

Example 2: Cloning and Identification of *Talaromyces verruculosus* CBH2

Genomic DNA Extraction

The *Talaromyces verruculosus* strain NN046799 was inoculated onto a PDA plate and incubated for 7 days at 37° C. in the darkness. Several mycelia-PDA plugs were inoculated into 500 ml shake flasks containing 100 ml of YPG medium. The flasks were incubated for 4 days at 37° C. with shaking at 160 rpm.

The mycelia were collected by filtration through MIRACLOTH® and frozen under liquid nitrogen. Frozen mycelia were ground, by a mortar and a pestle, to a fine powder, and genomic DNA was isolated using DNeasy® Plant Maxi Kit (24) (QIAGEN GmbH, Hilden, Germany) following the manufacturer's instruction.

Genome Sequencing, Assembly and Annotation

The extracted genomic DNA sample of NN046799 was delivered to Novozymes A/S for genome sequencing using an ILLUMINA® MiSeq System (Illumina, Inc., San Diego, CA, USA). The raw reads were assembled at Novozymes Denmark using program Spades (Anton Bankevich et al., 2012, *Journal of Computational Biology,* 19 (5): 455-477). The assembled sequences were analyzed using standard bioinformatics methods for gene identification and function prediction. GeneMark-ES fungal version was used for gene prediction. Blastall version 2.2.10 (Altschul et al., 1990, *Journal of Molecular Biology,* 215 (3): 403-410) and HMMER version 2.1.1 were used to predict function based on structural homology. The *Talaromyces verruculosus* GH6 cellobiohydrolase II (CBH2) gene was identified directly by analysis of the Blast results. The Agene program and SignalP program were used to identify start codons. SignalP program was further used to predict signal peptides. Pepstats was used to predict isoelectric points and molecular weights.

Cloning of the *Talaromyces verruculosus* GH6 CBH2 Gene from Genomic DNA

The above identified *Talaromyces verruculosus* GH6 CBH2 gene was cloned to the expression vector pCaHj505 ($EP2748189B_1$) and heterologously expressed in *Aspergillus oryzae* strain MT3568.

| | DNA sequence | Protein sequence |
|---|---|---|
| *Talaromyces verruculosus* GH6 CBH2 | SEQ ID NO: 23 | SEQ ID NO: 4 |

Based on the DNA information obtained from genome sequencing, oligonucleotide primers, shown below, were designed to amplify the coding sequences of the *Talaromyces verruculosus* GH6 CBH2 gene from NN046799. The primers were synthesized by Invitrogen, Beijing, China.

```
Forward Primer:
                                            (SEQ ID NO: 35)
5'-ACACAACTGGGGATCCACCatgctgcgatatctttccattgtt-3'
```

-continued

```
Reverse Primer:
                                         (SEQ ID NO: 36)
5'-CCCTCTAGATCTCGAGaaaggatattggtgcagtcaaagctg-3'
```

Lowercase characters of forward primers represented the coding regions of the genes while lowercase characters of reverse primers represented the complementary downstream flanking regions of the coding sequences of both genes. Bold characters represented a region homologous to insertion sites of pCaHj505. The 4 letters underlined in the forward primers represented the Kozark sequence as the initiation of translation process.

For the amplification of the *Talaromyces verruculosus* GH6 CBH2 gene, 10 μmol of the forward and reverse primers (SEQ ID NO:35 & 36) were used in a PCR reaction composed of 2 μl of genomic DNA of NN046799, 10 μl of 5× Phusion® GC Buffer, 1.5 μl of DMSO, 1.5 ul of 2.5 mM each of dATP, dTTP, dGTP, and dCTP, and 0.6 unit of PHUSION™ High-Fidelity DNA Polymerase and ddH2O to a final volume of 50 ul. The amplification was performed using a Peltier Thermal programmed for denaturing at 98° C. for 1 minute; 10 cycles of each denaturing at 98° C. for 30 seconds, annealing at 70° C. for 30 seconds, with a 1° C. decrease per cycle and elongation at 72° C. for 2 minutes and 30 seconds; then 25 cycles each at 98° C. for 30 seconds, 60° C. for 30 seconds, and 72° C. for 2 minutes and 30 seconds; and a final extension at 72° C. for 7 minutes.

The PCR products were isolated by 1.0% agarose gel electrophoresis using 90 mM Tris-borate and 1 mM EDTA (TBE) buffer where a single product band of ~1.8 kb band for the *Talaromyces verruculosus* GH6 CBH2 gene was visualized under UV light. The PCR product was then purified from solutions by using the Illustra™ GFX™ PCR DNA and Gel Band Purification Kit (GE Healthcare, Buckinghamshire, UK) according to the manufacturers' instructions.

The plasmid of pCaHj505 was digested with BamHI and XhoI. The linearized vector product was isolated by 1.0% agarose gel electrophoresis using TBE buffer and purified using an ILLUSTRA™ GFX™ PCR DNA and Gel Band Purification Kit.

For cloning, the In-Fusion® HD Cloning Kit (Clontech Laboratories, Inc., Mountain View, CA, USA) was used. Briefly, 1 ul of linearized pCaHj505, 3 ul of the *Talaromyces verruculosus* GH6 CBH2 PCR product were added to 1 ul of the 5× In-fusion mix. Then the ligation reaction solution was incubated at 50° C. for 15 minutes, and kept on ice till *E. coli* transformation.

The ligation reaction solution was used to transform *E. coli* TOP10 competent cells (TIANGEN. Biotech Co. Ltd., Beijing, China) following the manufacturers' instructions. 20-30 transformants were obtained in each transformation. Several *E. coli* transformants from each transformation were selected and sent for sequencing using 3730XL DNA Analyzers (Applied Biosystems Inc, Foster City, CA, USA) in SinoGenoMax (SinoGenoMax Company Limited, Beijing, China). The one that was confirmed with the right gene insertion and the correct sequence was selected for plasmid DNA preparation. The selected transformants were inoculated to LBA medium and grown at 37° C., 200 rpm, overnight. Plasmid DNA was prepared using a QIAPREP® Spin Miniprep Kit (QIAGEN GmbH, Hilden, Germany). This resulted in plasmid p505-GH6_Tave, in which the transcriptions of the coding sequences of the *Talaromyces verruculosus* GH6 CBH2 gene was under the control of a TAKA-amylase promoter derived from *Aspergillus oryzae.*

Expression of the *Talaromyces verruculosus* GH6 CBH2 Gene in *Aspergillus oryzae*

*Aspergillus oryzae* strain MT3568 was used for the heterologous expression of the gene encoding the *Talaromyces verruculosus* GH6 CBH2.

Protoplasts were prepared and transformed according to the method of Christensen et al., 1988, *Bio/Technology* 6:1419-1422.

Plasmid p505-GH6_Tave was used to transform MT3568. In brief, 3 μg plasmid DNA was added to 100 ul of protoplasts and after incubation at room temperature for 10 minutes, 300 ul of 60% PEG was added and mixed with protoplasts. Then after another 30 minutes incubation at room temperature, protoplasts were resuspended in ~6 ml of top agar medium and spread onto the Minimal medium plate. The plate was incubated at 37° C. until transformants were visible and started to sporulate.

The transformation yielded about 20 transformants. Four transformants were isolated on COVE medium reisolation plates and were then inoculated separately into 3 ml of YPM medium in 24-well deep well plate and incubated at 30° C., 150 rpm. After 3 days incubation, 20 ul of supernatant from the culture was analyzed on NUPAGER NOVEX® 4-12% Bis-Tris Gel with 50 mM MES (Invitrogen Corporation, Carlsbad, CA, USA) according to the manufacturer's instructions. The resulting gel was stained with INSTANTBLUE™ (Expedeon Ltd., Babraham Cambridge, UK). SDS-PAGE profiles of the cultures showed that the majority of the transformants had a major band of approximately ~65 kDa for the *Talaromyces verruculosus* GH6 CBH2. The expression strain was then designated as O13UA4 accordingly.

Fermentation of *Aspergillus oryzae* Expression Strain 013UA4

Five fully sporulated slants of the expression strain 013UA4 was each washed with 5 ml of DAP4C and inoculated into 28 2-liter flasks each containing 400 ml of DAP4C medium, shaking at 30° C., 80 rpm. The culture was harvested on day 3 and filtered by using a 0.2 μm aPES Membrane. The filtered broth sample was purified as described below.

Purification of recombinant *Talaromyces verruculosus* CBHII from *Aspergillus oryzae* O13UA4

A 11200 ml volume of filtered supernatant of *Aspergillus oryzae* O13UA4 was precipitated with ammonium sulfate (80% saturation), the protein was re-dissolved in $ddH_2O$, followed by adjusting conductivity to 145 ms/cm with $(NH_4)_2SO_4$, and filtered through a 0.45 μm filter. The final volume was 130 ml. The solution was applied to a 40 ml Phenyl Sepharose high performance column, proteins were washed with a linear 1.2-0 M $(NH_4)_2SO_4$ gradient. Fractions were analyzed by SDS-PAGE using a NUPAGER NOVEX® 4-12% Bis-Tris Gel with 50 mM MES. The resulting gel was stained with INSTANTBLUE™. Fractions containing a band at approximately 65 kDa were pooled. Then the pooled solution was concentrated by ultrafiltration.

Example 3: Cloning and Identification of *Cladosporium antarcticum* EG2

Genomic DNA Extraction

The fungal strain NN058608 was inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm. The mycelia were collected by filtration through MIRA- CLOTH® (Calbiochem, La Jolla, CA, USA) and frozen under liquid nitrogen. Frozen mycelia were ground, by a mortar and a pestle, to a fine powder, and genomic DNA was isolated using MP Fast DNA spin kit for soil (MP Biomedicals, Santa Ana, California, USA) following the manufacturer's instruction.

Genome Sequencing, Assembly and Annotation

The extracted genomic DNA sample of NN058608 was delivered to Exiqon A/S (Denmark) for genome sequencing using an ILLUMINA® MiSeq System (Illumina, Inc., San Diego, CA, USA). The raw reads were assembled at Novozymes Denmark using program Spades (Anton Bankevich et al., 2012, *Journal of Computational Biology,* 19 (5): 455-477). The assembled sequences were analyzed using standard bioinformatics methods for gene identification and function prediction. GeneMark-ES fungal version (Ter-Hovhannisyan V et al., 2008, *Genome Research* 18 (12): 1979-1990) was used for gene prediction. Blastall version 2.2.10 (Altschul et al., 1990, *Journal of Molecular Biology,* 215 (3): 403-410) and HMMER version 2.1.1 (National Center for Biotechnology Information (NCBI), Bethesda, MD, USA) were used to predict function based on structural homology. The *Cladosporium antarcticum* family GH5 endo-beta-1,4-glucanase (SEQ ID NO: 31 for the DNA sequence and SEQ ID NO: 5 for the deduced amino acid sequence) was identified directly by analysis of the Blast results. The Agene program (Munch and Krogh, 2006, *BMC Bioinformatics,* 7:263) and SignalP program (Nielsen et al., 1997, *Protein Engineering,* 10:1-6) were used to identify start codons. SignalP program was further used to predict signal peptides. Pepstats (Rice et al., 2000, *Trends Genet,* 16 (6): 276-277) was used to predict isoelectric points and molecular weights.

Cloning of the *Cladosporium antarcticum* GH5 Endo-Beta-1,4-Glucanase Gene from Genomic DNA The above identified *Cladosporium antarcticum* GH5 endo-beta-1,4-glucanase gene was cloned to expression vectors and recombinantly expressed in *Aspergillus oryzae.* Details were listed in Table 2 below.

TABLE 2

| | DNA sequence | Protein sequence | Vector | Host strain |
|---|---|---|---|---|
| *Cladosporium antarcticum* GH5 endo-beta-1,4-glucanase | SEQ ID NO: 31 | SEQ ID NO: 5 | pDAU724 | Dau785 |

The expression vector pDAU724 was described in WO2016/026938.

Based on the DNA information obtained from genome sequencing, oligonucleotide primers, shown below, were designed to amplify the coding sequence of the *Cladosporium antarcticum* GH5 endo-beta-1,4-glucanase from the genomic DNA of NN058608.

Forward Primer:

(SEQ ID NO: 37)

5'-ACACAACTGGGGATC<u>CACC</u>atgaagtcttctttcatcgctgttgc a-3'

Reverse Primer:

(SEQ ID NO: 38)

5'-GTCACCCTCTAGATCTcgagcgactggactacaaatccagcaaa gatc-3'

Lowercase characters of forward primers represent the coding regions of the genes while lowercase characters of reverse primers represent the downstream flanking regions of the coding sequence. Bold characters represent a region homologous to insertion sites of pPFJO355 or pDAU724. The 4 letters underlined in the forward primers represent the Kozark sequence as the initiation of translation process.

For the amplification of the *Cladosporium antarcticum* GH5 endo-beta-1,4-glucanase gene, 10 μmol of the forward and reverse primers (SEQ ID NO: 37 & 38) were used in a PCR reaction composed of 2 μl of genomic DNA of *Cladosporium antarcticum* strain NN058608, 10 μl of 5× Phusion® GC Buffer (Finnzymes Oy, Espoo, Finland), 1 ul of 2.5 mM each of dATP, dTTP, dGTP, and dCTP, and 0.6 unit of PHUSION™ High-Fidelity DNA Polymerase (Finnzymes Oy, Espoo, Finland) and double distilled water to a final volume of 50 ul. The amplification was performed using a Peltier Thermal Cycler (MJ Research Inc., South San Francisco, CA, USA) programmed for denaturing at 98° C. for 1 minute; 10 cycles of denaturing each at 98° C. for 30 seconds, annealing at 68° C. for 30 seconds, with a 1° C. decrease per cycle and elongation at 72° C. for 1 minute; then 26 cycles each at 98° C. for 30 seconds, 58° C. for 30 seconds, and 72° C. for 1 minute; and a final extension at 72° C. for 10 minutes.

The PCR product was isolated by 1.0% agarose gel electrophoresis using 90 mM Tris-borate and 1 mM EDTA (TBE) buffer where a single product band of approximately 1.4 kb for *Cladosporium antarcticum* GH5 endo-beta-1,4-glucanase gene was visualized under UV light. The PCR product was then purified from solution by using the Illustra™ GFX™ PCR DNA and Gel Band Purification Kit (GE Healthcare, Buckinghamshire, UK) according to the manufacturers' instructions.

The expression vector was linearized by restriction digestion. The plasmid of pDAU724 was digested with BamHI and XhoI. The linearized vector product was isolated by 1.0% agarose gel electrophoresis using TBE buffer and purified using an ILLUSTRA™ GFX™ PCR DNA and Gel Band Purification Kit.

For cloning of the *Cladosporium antarcticum* GH5 endo-beta-1,4-glucanase gene, the In-Fusion® HD Cloning Kit (Clontech Laboratories, Inc., Mountain View, CA, USA) was used. Briefly, 0.3 ul of linearized pDAU724 vector and 3.7 ul of GH5 endo-beta-1,4-glucanase PCR product were added to 1 ul of the 5× in-fusion mix. Then the ligation reaction solution was incubated at 50° C. for 15 minutes. It was kept on ice till *E. coli* transformation.

The ligation reaction solution was used to transform *E. coli* TOP10 competent cells (TIANGEN Biotech Co. Ltd., Beijing, China) following the manufacturers' instructions. 20-30 transformants were obtained in each transformation. Two *E. coli* transformants from the transformation were selected and sent for sequencing using 3730XL DNA Analyzers (Applied Biosystems Inc, Foster City, CA; USA) in SinoGenoMax (SinoGenoMax Company Limited, Beijing, China). The one that was confirmed with the right gene insertion and the correct sequence was selected for plasmid DNA preparation. The selected transformants were inoculated to LBA medium and grown at 37° C., 200 rpm, overnight. Plasmid DNA was prepared using a QIAPREP® Spin Miniprep Kit (QIAGEN GmbH, Hilden, Germany). This resulted in plasmids pDau724-GH5_Clan1, in which the transcription of the *Cladosporium antarcticum* GH5 endo-beta-1,4-glucanase gene coding sequence was under the control of a NA2TPI promoter.

Expression of *Cladosporium antarcticum* GH5 Endo-Beta-1,4-Glucanase Gene in *Aspergillus oryzae*

*Aspergillus oryzae* strain DAu785 was used for the heterologous expression of the gene encoding the *Cladosporium antarcticum* GH5 endo-beta-1,4-glucanase. Protoplasts were prepared and transformed according to the method of Christensen et al., 1988, *Bio/Technology* 6:1419-1422.

Plasmids pDau724-GH5_Clan1 was used to transform Dau785. In brief, 3 µg DNA was added to 100 ul of protoplasts and after incubation at room temperature for 10 minutes, 300 ul of 60% PEG was added and mixed with protoplasts. After another 30 minutes incubation at room temperature, protoplasts were resuspended in ~6 ml of top agar medium and spread onto the Minimal medium plate. The plate was incubated at 37° C. until transformants were visible and started to sporulate.

The transformations yielded about 20 transformants. Four transformants were isolated on COVE medium reisolation plates and were then inoculated separately into 3 ml of YPM medium in 24-well deep well plate and incubated at 30° C., 150 rpm. After 3 days incubation, 20 ul of supernatant from each culture were analyzed on NUPAGER NOVEX® 4-12% Bis-Tris Gel with 50 mM MES (Invitrogen Corporation, Carlsbad, CA, USA) according to the manufacturer's instructions. The resulting gel was stained with INSTANTBLUE™ (Expedeon Ltd., Babraham Cambridge, UK). SDS-PAGE profiles of the cultures showed that the majority of the transformants had a major band of approximately 43 kDa for the *Cladosporium antarcticum* GH5 endo-beta-1,4-glucanase. The resulting expression strain was designated as 054U3N.

Fermentation of *Aspergillus oryzae* Expression Strain 054U3N

Two fully sporulated slants of the expression strain O54U3N were washed with 10 ml of DAP4C and inoculated into 10 2-liter flasks each containing 400 ml of DAP4C medium, shaking at 30° C., 80 rpm. The culture broth was harvested by using a 1000 ml Rapid-Flow Bottle Top Filter 0.2 µm aPES membrane (ThermoFisher Scientific, Waltham, Massachusetts, USA). The filtered broth sample was purified as described below.

Purification of Recombinant *Cladosporium antarcticum* GH5 Endo-Beta-1,4-Glucanase from *Aspergillus oryzae* 054U3N 4000 ml supernatant of the recombinant strain 054U3N was precipitated with ammonium sulfate (80% saturation), the protein was re-dissolved in ddH2O, followed by adjusting conductivity to 145 ms/cm with $(NH_4)_2SO_4$, and filtered through a 0.45 µm filter. The final volume was 90 ml. The solution was applied to a 40 ml Phenyl hydrophobic column (GE Healthcare, Buckinghamshire, UK), proteins were washed with a linear 1.8-0.0 M $(NH_4)_2SO_4$ gradient. Fractions were analyzed by SDS-PAGE using a NUPAGE® NOVEX® 4-12% Bis-Tris Gel with 50 mM MES. The resulting gel was stained with INSTANTBLUE™. Fractions containing a band at approximately 43 kDa were pooled. The pooled solution was adjusted conductivity to 145 ms/cm with $(NH_4)_2SO_4$ and applied to a 20 ml: Phenyl Sepharose High Performance column (GE Healthcare, Buckinghamshire, UK), proteins were washed with a linear 1.5-0.0 M $(NH_4)_2SO_4$ gradient. Fractions were analyzed by SDS-PAGE using a NUPAGER NOVEX® 4-12% Bis-Tris Gel with 50 mM MES. The resulting gel was stained with INSTANTBLUE™. Fractions containing a band at approximately 43 kDa were pooled. Then the pooled solution was concentrated by ultrafiltration.

Example 4: Cloning and Identification of *Talaromyces pinophilus* GH3 Beta-Glucosidase Genomic DNA Extraction The fungal strain NN046877 was inoculated onto a PDA plate and incubated for 7 days at 37° C. in the darkness. Several mycelia-PDA plugs were inoculated into 500 ml shake flasks containing 100 ml of YPG medium. The flasks were incubated for 3 days at 37° C. with shaking at 160 rpm. The mycelia were collected by filtration through MIRACLOTH® and frozen under liquid nitrogen. Frozen mycelia were ground, by a mortar and a pestle, to a fine powder, and genomic DNA was isolated using DNeasy® Plant Maxi Kit (24) (QIAGEN GmbH, Hilden, Germany) following the manufacturer's instruction.

Genome Sequencing, Assembly and Annotation

The extracted genomic DNA sample of NN046877 was delivered to Beijing Genome Institute (BGI, Shenzhen, China) for genome sequencing using an ILLUMINA® GA2 System (Illumina, Inc., San Diego, CA, USA). The raw reads were assembled at BGI using program SOAPdenovo (Li et al., 2010, *Genome Research,* 20:265-72). The assembled sequences were analyzed using standard bioinformatics methods for gene identification and functional prediction. GeneMark-ES fungal version (Ter-Hovhannisyan V et al., 2008, *Genome Research,* 18 (12): 1979-1990) was used for gene prediction. Blastall version 2.2.25 (Altschul et al., 1990, *Journal of Molecular Biology,* 215 (3): 403-410) and HMMER version 2.1.1 (National Center for Biotechnology Information (NCBI), Bethesda, MD, USA) were used to predict function based on structural homology. The *Talaromyces pinophilus* family GH3 beta-glucosidase (SEQ ID NO: 32 for the DNA sequence and SEQ ID NO: 6 for the deduced amino acid sequence) was identified directly by analysis of the Blast results. The Agene program (Munch and Krogh, 2006, *BMC Bioinformatics,* 7:263) and SignalP program (Nielsen et al., 1997, *Protein Engineering,* 10:1-6) were used to identify start codons. SignalP program was further used to predict signal peptides. Pepstats (Rice et al., 2000, *Trends Genet,* 16 (6): 276-277) was used to predict isoelectric points and molecular weights.

Cloning of the *Cladosporium antarcticum* GH5 Endo-Beta-1,4-Glucanase and the *Talaromyces Pinophilus* GH3 Beta-Glucosidase Genes from Genomic DNA The above identified *Talaromyces pinophilus* GH3 beta-glucosidase gene was cloned to expression vectors and recombinantly expressed in *Aspergillus oryzae*. Details were listed in Table 3 below.

TABLE 3

| | DNA sequence | Protein sequence | Vector | Host strain |
|---|---|---|---|---|
| *Talaromyces pinophilus* GH3 beta-glucosidase | SEQ ID NO: 32 | SEQ ID NO: 6 | pPFJO355 | HowB101 |

The expression vector pPFJO355 was described in WO 2011/005867.

Based on the DNA information obtained from genome sequencing, oligonucleotide primers, shown below, were designed to amplify the coding sequence of the *Talaromyces pinophilus* GH3 beta-glucosidase from NN046877.

Forward Primer:

(SEQ ID NO: 39)
5'-ACACAACTGGGGATCCACCatgcggaacagtttattgatttcg-3'

Reverse Primer:

(SEQ ID NO: 40)
5'-GTCACCCTCTAGATCTacaaaagggtggaagccgatc-3'

Lowercase characters of forward primers represent the coding regions of the genes while lowercase characters of reverse primers represent the downstream flanking regions of the coding sequence. Bold characters represent a region homologous to insertion sites of pPFJO355. The four letters underlined in the forward primers represent the Kozark sequence as the initiation of translation process.

For the amplification of the *Talaromyces pinophilus* GH3 beta-glucosidase gene, 20 μmol of the forward and reverse primers (SEQ ID NO: 39 & 40) were used in a PCR reaction composed of 2 ul of genomic DNA of *Talaromyces pinophilus* strain NN046877, 10 μl of 5× Phusion® GC Buffer, 1.5 ul of DMSO, 1.5 ul of 2.5 mM each of dATP, dTTP, dGTP, and dCTP, and 0.6 unit of PHUSION™ High-Fidelity DNA Polymerase and ddH2O to a final volume of 50 ul. The amplification was performed using a Peltier Thermal programmed for denaturing at 98° C. for 1 minute; 6 cycles of denaturing each at 98° C. for 15 seconds, annealing at 66° C. for 30 seconds, with a 1° C. decrease per cycle and elongation at 72° C. for 1 minute and 45 seconds; then 25 cycles each at 98° C. for 15 seconds, 62° C. for 30 seconds, and 72° C. for 1 minute and 45 seconds; and a final extension at 72° C. for 5 minutes.

The PCR product was isolated by 1.0% agarose gel electrophoresis using 90 mM Tris-borate and 1 mM EDTA (TBE) buffer where a single product band of approximately 3.0 kb band for *Talaromyces pinophilus* GH3 beta-glucosidase gene were visualized under UV light. The PCR product was then purified from solution by using the Illustra™ GFX™ PCR DNA and Montage™ PCR96 Clean-Up (Millipore Corporation, Billerica, MA 01821, USA) according to the manufacturers' instructions.

The expression vector was linearized by restriction digestion. The plasmid of pPFJO355 was digested with BamHI and BglII. The linearized vector product was isolated by 1.0% agarose gel electrophoresis using TBE buffer and purified using an ILLUSTRA™ GFX™ PCR DNA and Gel Band Purification Kit.

For cloning of the *Talaromyces pinophilus* GH3 beta-glucosidase gene, the In-Fusion 2.0 CF dry down Cloning kit (Clontech Laboratories, Inc., Mountain View, CA, USA) was used. The In-Fusion Dry Down pellet was suspended in 3 ul of ddH2O and 1 ul of the linearized pPFJO355 vector. Then 2 ul of the suspension solution was added to 3 ul of GH3 beta-glucosidase gene PCR product. The ligation reaction solution was incubated at 37° C. for 15 minutes followed by 50° C. for 15 minutes. It was kept at room temperature till the *E. coli* transformation.

The ligation reaction solution was used to transform *E. coli* TOP10 competent cells (TIANGEN Biotech Co. Ltd., Beijing, China) following the manufacturers' instructions. 20-30 transformants were obtained in each transformation. Two *E. coli* transformants were selected and sent for sequencing using 3730XL DNA Analyzers (Applied Biosystems Inc, Foster City, CA, USA) in SinoGenoMax (SinoGenoMax Company Limited, Beijing, China). The one that was confirmed with the right gene insertion and the correct sequence was selected for plasmid DNA preparation. The selected transformants were inoculated to LBA medium and grown at 37° C., 200 rpm, overnight. Plasmid DNA was prepared using a QIAPREP® Spin Miniprep Kit (QIAGEN GmbH, Hilden, Germany). This resulted in plasmid pGH3_ZY503522_84, in which the transcription of the *Talaromyces pinophilus* GH3 beta-glucosidase gene coding sequence was under the control of an *Aspergillus oryzae* alpha-amylase gene promoter.

Expression of *Talaromyces pinophilus* GH3 Beta-Glucosidase Gene in *Aspergillus oryzae*

*Aspergillus oryzae* strain HowB101 was used for the heterologous expression of the gene encoding the *Talaromyces pinophilus* GH3 beta-glucosidase. Protoplasts were prepared and transformed according to the method of Christensen et al., 1988, *Bio/Technology* 6:1419-1422.

Plasmids pGH3_ZY503522_84 was used to transform HowB101. In brief, 3 μg DNA was added to 100 ul of protoplasts and after incubation at room temperature for 10 minutes, 300 ul of 60% PEG was added and mixed with protoplasts. After another 30 minutes incubation at room temperature, protoplasts were resuspended in ~6 ml of top agar medium and spread onto the Minimal medium plate. The plate was incubated at 37° C. until transformants were visible and started to sporulate.

The transformations yielded about 20 transformants each. Four transformants were isolated on COVE medium reisolation plates and were then inoculated separately into 3 ml of YPM medium in 24-well deep well plate and incubated at 30° C., 150 rpm. After 3 days incubation, 20 ul of supernatant from each culture were analyzed on NUPAGE® NOVEX® 4-12% Bis-Tris Gel with 50 mM MES (Invitrogen Corporation, Carlsbad, CA, USA) according to the manufacturer's instructions. The resulting gel was stained with INSTANTBLUE™ (Expedeon Ltd., Babraham Cambridge, UK). SDS-PAGE profiles of the cultures showed that the majority of the transformants had a major band of approximately 90 kDa for the *Talaromyces pinophilus* GH3 beta-glucosidase. The resulting expression strain was designated O3XUX.

Fermentation of *Aspergillus oryzae* Expression Strain O3XUX

One fully sporulated slant of the expression strain O3XUX was washed with 10 ml of YPM and inoculated into 4 2-liter flasks each containing 400 ml of YPM medium, shaking at 30° C., 80 rpm. The culture was harvested on day 3 and filtered using a 0.45 μm DURAPORE Membrane (Millipore, Bedford, MA, USA). The filtered broth sample was purified as described below.

Purification of Recombinant *Penicillium Pinophilum* GH3 Beta-Glucosidase from *Aspergillus oryzae* 03XUX 1600 ml supernatant of the recombinant strain O3XUX was precipitated with ammonium sulfate (80% saturation) and re-dissolved in 80 ml of 20 mM Tris-HCl buffer, pH7.0, then dialyzed against the same buffer and filtered through a 0.45 mm filter, the final volume was 95 ml. The solution was applied to a 40 ml Q FF column (GE) equilibrated in 20 mM Tris-HCl buffer, pH7.0, and the proteins was eluted with a linear NaCl gradient (0-0.4M). Fractions eluted with 0.1-0.3M NaCl were collected. The collected sample was dialyzed against 20 mM Tris-HCl buffer, pH7.0, and applied to the same column again, the proteins was eluted with a linear NaCl gradient (0.1-0.3M). Fractions were evaluated by SDS-PAGE (NP0336BOX, NUPAGE 4-12% BT GEL 1.5MM15W). Fractions containing a band of approximately 90 kDa were pooled. Then the pooled solution was concentrated by ultrafiltration.

Example 5: Construction of Yeast Strains Expressing a *Talaromyces pinophilus* GH3 Beta-Glucosidase This example describes the construction of yeast cells expressing the *Talaromyces pinophilus* GH3 beta-glucosidase of SEQ ID NO: 6 under the control of one *S. cerevisiae* promoter: pTDH3, which is a strong constitutive promoter. Three pieces of DNA containing promoters, genes and terminators were designed to allow for homologous recombination between the 3 DNA fragments and into the XII-2 locus of the yeast MeJi797. The resulting strain would have one 5' homology containing fragment with a promoter, 1 promoter and gene containing fragment, and one 3' homology fragment with a terminator integrated into the *S. cerevisiae* genome at the XII-2 locus.

Construction of the 5' XII-2 Homology Containing Fragment with pTDH3 (Left Fragment 1)

The linear DNA containing 500 bp homology to the XII-2 site and the *S. cerevisiae* pTDH3 promoter was PCR amplified from HP30 plasmid DNA with primers 1230183 (5'-TCTTT TCGCG CCCTG GAAA-3'; SEQ ID NO: 41) and 1230194 (5'-TTTGT TTGTT TATGT GTGTT TATTC GAAAC TAAGT TC-3'; SEQ ID NO: 42). Fifty pmoles each of forward and reverse primer was used in a PCR reaction containing 5 ng of plasmid DNA as template, 1× Platinum SuperFi HF Buffer (Thermo Fisher Scienctific), and 2 units SuperFi DNA polymerase in a final volume of 50 μL. The PCR was performed in a T100™ Thermal Cycler (Bio-Rad Laboratories, Inc.) programmed for one cycle at 98° C. for 30 seconds followed by 35 cycles each at 98° C. for 10 seconds, 60° C. for 10 seconds, and 72° C. for 1.5. minutes with a final extension at 72° C. for 5 minutes. Following thermocycling, the PCR reaction products gel isolated and cleaned up using the QIAquick Gel Extraction kit (Qiagen).

Construction of the 3' XII-2 Homology Containing Fragment with tPRM9 (Right Fragment 1)

The linear DNA containing 500 bp homology to the XII-2 site and the *S. cerevisiae* tPRM9 terminator was PCR amplified from TH12 plasmid DNA with primers 1230177 (5'-ACAGA AGACG GGAGA CACTA GC-3'; SEQ ID NO: 43) and 1230216 (5'-TCAGT CCAAT GACAG TATTT TCTCC TTCTC AC-3'; SEQ ID NO: 44). Fifty pmoles each of forward and reverse primer was used in a PCR reaction containing 5 ng of plasmid DNA as template, 1× Platinum SuperFi HF Buffer (Thermo Fisher Scienctific), and 2 units SuperFi DNA polymerase in a final volume of 50 μL. The PCR was performed in a T100™ Thermal Cycler (Bio-Rad Laboratories, Inc.) programmed for one cycle at 98° C. for 30 seconds followed by 35 cycles each at 98° C. for 10 seconds, 60° C. for 10 seconds, and 72° C. for 1.5 minutes with a final extension at 72° C. for 5 minutes. Following thermocycling, the PCR reaction products gel isolated and cleaned up using the QIAquick Gel Extraction kit (Qiagen).

Integration of the Left, Middle and Right-Hand Fragments

The yeast MeJi797 was transformed with the left, middle and right integration fragments described above. In each transformation pool, the left fragment and right fragment with 50 ng of each fragment was used. There was 1 set of the left and right fragment pools used. There is also an additional middle fragment consisted of a beta-glucosidase gene and a signal peptide with ~50 ng of each fragment (200 ng total). The synthetic beta-glucosidase DNA fragment contains genes for: P23WFT. To aid homologous recombination of the left, middle and right fragments at the genomic XII-2 sites a plasmid containing MAD7 and guide RNA specific to XII-2 (pMIBa638) was also used in the transformation. The one synthetic middle component was combined with the left and right fragments and transformed into the into *S. cerevisiae* strain MeJi797 following a yeast electroporation protocol. Transformants were selected on YPD+cloNAT to select for transformants that contain the Mad7 plasmid pMIBa638. Transformants were either picked manually by hand onto YPD plates or by using a Q-pix Colony Picking System (Molecular Devices) to inoculate 1 well of 96-well plate containing YPD media. The plates were grown for 2 days then glycerol was added to 20% final concentration and the plates were stored at −80° C. until needed. Integration of the beta-glucosidase construct was verified by PCR with locus specific primers and subsequent sequencing. The resulting strains generated in MeJi797 in this example are shown in Table 4.

TABLE 4

Strains with beta-glucoside gene P23WFT to MeJi797

| Strain ID | Promoter1 | BG gene |
|---|---|---|
| MeJi797 | | |
| S833-E04 | pTDH3 | P23WFT |
| S833-G04 | pTDH3 | P23WFT |

Example 6: Construction of Yeast Strains Expressing a *Talaromyces verruculosus* CBH2

This example describes the construction of yeast cells expressing a *Talaromyces verruculosus* CBH2 of SEQ ID NO: 4 under the control of one *S. cerevisiae* promoter: pSeTDH3, which is a strong constitutive promoter. Three pieces of DNA containing promoters, genes and terminators were designed to allow for homologous recombination between the 3 DNA fragments and into the X-3 locus of the yeast S709-A06 (MeJi797 with *A. fumigatus* beta-glucosidase). The resulting strain would have one 5' homology containing fragment with a promoter, 1 promoter and gene containing fragment, and one 3' homology fragment with a terminator integrated into the *S. cerevisiae* genome at the X-3 locus.

Construction of the 5' X-3 Homology Containing Fragment with pSeTDH3 (Left Fragment 2)

The linear DNA containing 500 bp homology to the X-3 site and the *S. cerevisiae* pSeTDH3 promoter was PCR amplified from HP6 plasmid DNA with primers 1230181 (5'-AACGA CAGCA CAAAG GAACT TTCAC-3'; SEQ ID NO: 45) and 1230196 (5'-TTTTA TTGTA TGTGT GTGTG TTTGA AACTA AAGTT CTTG-3'; SEQ ID NO: 46). Fifty pmoles each of forward and reverse primer was used in a PCR reaction containing 5 ng of plasmid DNA as template, 1× Platinum SuperFi HF Buffer (Thermo Fisher Scienctific), and 2 units SuperFi DNA polymerase in a final volume of 50 μL. The PCR was performed in a T100™ Thermal Cycler (Bio-Rad Laboratories, Inc.) programmed for one cycle at 98° C. for 30 seconds followed by 35 cycles each at 98° C. for 10 seconds, 60° C. for 10 seconds, and 72° C. for 1.5 minutes with a final extension at 72° C. for 5 minutes. Following thermocycling, the PCR reaction products gel isolated and cleaned up using the QIAquick Gel Extraction kit (Qiagen).

Construction of the 3' X-3 Homology Containing Fragment with tPDC6 (Right Fragment 2)

The linear DNA containing 500 bp homology to the X-3 site and the *S. cerevisiae* tPDC6 terminator was PCR amplified from TH39 plasmid DNA with primers 1230179 (5'-GCCAT TAGTA GTGTA CTCAA ACGAA TTATT G-3'; SEQ ID NO: 47) and 1230745 (5'-GGCTA CTGAT TTTGT TAAGC AACTC ATCAA G-3'; SEQ ID NO: 48. Fifty pmoles each of forward and reverse primer was used in a PCR reaction containing 5 ng of plasmid DNA as template, 1× Platinum SuperFi HF Buffer (Thermo Fisher Scienctific), and 2 units SuperFi DNA polymerase in a final volume of 50 µL. The PCR was performed in a T100™ Thermal Cycler (Bio-Rad Laboratories, Inc.) programmed for one cycle at 98° C. for 30 seconds followed by 35 cycles each at 98° C. for 10 seconds, 60° C. for 10 seconds, and 72° C. for 1.5 minutes with a final extension at 72° C. for 5 minutes. Following thermocycling, the PCR reaction products gel isolated and cleaned up using the QIAquick Gel Extraction kit (Qiagen).

Integration of the Left, Middle and Right-Hand Fragments to Generate Yeast Strains with P43VY6

The yeast S709-A06 (MeJi797 expressing the *A. fumigatus* beta-glucosidase of SEQ ID NO: 8) was transformed with the left, middle and right integration fragments described above. In each transformation pool, the left fragment and right fragment with 50 ng of each fragment was used. There was 1 set of the left and right fragment pools used. There is also an additional middle fragment consisted of a CBH2 gene and a signal peptide with ~50 ng of each fragment (200 ng total). The synthetic CBH2 DNA fragment contains genes for: P43VY6. To aid homologous recombination of the left, middle and right fragments at the genomic X-3 sites a plasmid containing MAD7 and guide RNA specific to X-3 (pMIBa647) was also used in the transformation. The one synthetic middle component was combined with the left and right fragments and transformed into the into *S. cerevisiae* strain S709-A06 following a yeast electroporation protocol. Transformants were selected on YPD+cloNAT to select for transformants that contain the Mad7 plasmid pMIBa647. Transformants were either picked manually by hand onto YPD plates or by using a Q-pix Colony Picking System (Molecular Devices) to inoculate 1 well of 96-well plate containing YPD media. The plates were grown for 2 days then glycerol was added to 20% final concentration and the plates were stored at −80° C. until needed. Integration of the CBH2 construct was verified by PCR with locus specific primers and subsequent sequencing. The strains generated in S709-A06 of this example are were designated S1131-A05 and S1131-B05.

Example 7: Construction of Yeast Strains Expressing a *Penicillium emersonii* CBH1 and a *Trichoderma reesei* Endo-Glucanase This example describes the construction of yeast cells expressing the *Penicillium emersonii* CBH1 of SEQ ID NO: 1 under the control of one *S. cerevisiae* promoter: pSeTDH3, which is a strong constitutive promoter, while also expressing the *Trichoderma reesei* EG1 of SEQ ID NO: 29 under the control of one *S. cerevisiae* promoter: pSKTDH3. Five pieces of DNA containing promoters, genes and terminators were designed to allow for homologous recombination between the 5 DNA fragments and into the X-3 locus of the yeast S709-A06 (MeJi797 expressing the *A. fumigatus* beta-glucosidase of SEQ ID NO: 8). The resulting strain would have one 5' homology containing fragment with a promoter, 2 promoter and gene containing fragments, 1 terminator and promoter containing fragment, and one 3' homology fragment with a terminator integrated into the *S. cerevisiae* genome at the X-3 locus.

Construction of the pSKTDH3 Containing Fragment with tPDC6 (Middle Fragment 1)

The linear DNA containing 143 bp homology to the *S. cerevisiae* tPDC6 terminator and the pSKTDH3 promoter was PCR amplified from TP46 plasmid DNA with primers 1230179 (5'-GCCAT TAGTA GTGTA CTCAA ACGAA TTATT G-3'; SEQ ID NO: 49) and 1230197 (5'-GTTTA GTTAA TTATA GTTCG TTGAC TGTGT TTCTT G-3'; SEQ ID NO: 50). Fifty pmoles each of forward and reverse primer was used in a PCR reaction containing 5 ng of plasmid DNA as template, 1× Platinum SuperFi HF Buffer (Thermo Fisher Scienctific), and 2 units SuperFi DNA polymerase in a final volume of 50 µL. The PCR was performed in a T100™ Thermal Cycler (Bio-Rad Laboratories, Inc.) programmed for one cycle at 98° C. for 30 seconds followed by 35 cycles each at 98° C. for 10 seconds, 60° C. for 10 seconds, and 72° C. for 1.5 minutes with a final extension at 72° C. for 5 minutes. Following thermocycling, the PCR reaction products gel isolated and cleaned up using the QIAquick Gel Extraction kit (Qiagen).

Construction of the P33517 Containing Fragment with tENO2 (Middle Fragment 2)

The linear DNA containing 143 bp homology to the *S. cerevisiae* tENO2 terminator and the pSKTDH3 promoter was PCR amplified from S709-H08 genomic DNA with primers 1230248 (5'-GGTCT CCTTT CTTTC AAGAA ACACA GTC-3'; SEQ ID NO: 51) and 1230232 (5'-ATGAT GAAAA AATAA GCAGA AAAGA CTAAT AATTC TTAG-3'; SEQ ID NO: 52). Fifty pmoles each of forward and reverse primer was used in a PCR reaction containing 5 ng of plasmid DNA as template, 1× Platinum SuperFi HF Buffer (Thermo Fisher Scienctific), and 2 units SuperFi DNA polymerase in a final volume of 50 µL. The PCR was performed in a T100™ Thermal Cycler (Bio-Rad Laboratories, Inc.) programmed for one cycle at 98° C. for 30 seconds followed by 35 cycles each at 98° C. for 10 seconds, 60° C. for 10 seconds, and 72° C. for 1.5 minutes with a final extension at 72° C. for 5 minutes. Following thermocycling, the PCR reaction products gel isolated and cleaned up using the QIAquick Gel Extraction kit (Qiagen).

Construction of the 3' X-3 Homology Containing Fragment with tENO2 (Right Fragment 3)

The linear DNA containing 500 bp homology to the X-3 site and the *S. cerevisiae* tENO2 terminator was PCR amplified from TH36 plasmid DNA with primers 1230176 (5'-AGTGC TTTTA ACTAA GAATT ATTAG TCTTT TCTGC-3'; SEQ ID NO: 53) and 1230745 (5'-GGCTA CTGAT TTTGT TAAGC AACTC ATCAA G-3'; SEQ ID NO: 54). Fifty pmoles each of forward and reverse primer was used in a PCR reaction containing 5 ng of plasmid DNA as template, 1× Platinum SuperFi HF Buffer (Thermo Fisher Scienctific), and 2 units SuperFi DNA polymerase in a final volume of 50 µL. The PCR was performed in a T100™ Thermal Cycler (Bio-Rad Laboratories, Inc.) programmed for one cycle at 98° C. for 30 seconds followed by 35 cycles each at 98° C. for 10 seconds, 60° C. for 10 seconds, and 72° C. for 1.5 minutes with a final extension at 72° C. for 5 minutes. Following thermocycling, the PCR reaction products gel isolated and cleaned up using the QIAquick Gel Extraction kit (Qiagen).

Integration of the Left, Middle and Right-Hand Fragments to Generate Yeast Strains with CBH1 and EG1

The yeast S709-A06 was transformed with the left, two middle and right integration fragments described above. In each transformation pool, the left fragment and right fragment with 50 ng of each fragment was used. There was 1 set of the left, two middle, and one right fragment pools used:

left fragment 2 (supra), middle fragment 1 (supra), middle fragment 2 (supra), and right fragment 3 (supra), designated Blend 1 master mix. There is also an additional middle fragment consisted of a signal peptide and CBH1 gene and a signal peptide with ~50 ng of each fragment (200 ng total). The synthetic CBH1 DNA fragment contains genes for: P244YG. To aid homologous recombination of the left, two middle and right fragments at the genomic X-3 sites a plasmid containing MAD7 and guide RNA specific to X-3 (pMIBa647) was also used in the transformation. The one synthetic middle component was combined with the Blend 1 master mix and transformed into the into *S. cerevisiae* strain S709-A06 following a yeast electroporation protocol. Transformants were selected on YPD+cloNAT to select for transformants that contain the Mad7 plasmid pMIBa647. Transformants were either picked manually by hand onto YPD plates or by using a Q-pix Colony Picking System (Molecular Devices) to inoculate 1 well of 96-well plate containing YPD media. The plates were grown for 2 days then glycerol was added to 20% final concentration and the plates were stored at −80° C. until needed. Integration of the CBH1 and EG1 construct was verified by PCR with locus specific primers and subsequent sequencing. The strains generated in S709-A06 in this example resulted in strains.

Example 8: Construction of Yeast Strains Expressing an *Aspergillus fumigatus* CBH1 and a *Cladosporium antareticum* Endo-Glucanase This example describes the construction of yeast cells expressing an *Aspergillus fumigatus* CBH1 of SEQ ID NO: 9 under the control of one *S. cerevisiae* promoter: pSeTDH3, which is a strong constitutive promoter, while also expressing the *Cladosporium antareticum* EG2 of SEQ ID NO: 5 under the control of one *S. cerevisiae* promoter: pSKTDH3. Five pieces of DNA containing promoters, genes and terminators were designed to allow for homologous recombination between the 5 DNA fragments and into the X-3 locus of the yeast S709-A06 (MeJi797 expressing the *A. fumigatus* beta-glucosidase of SEQ ID NO: 8). The resulting strain would have one 5' homology containing fragment with a promoter, 2 promoter and gene containing fragments, 1 terminator and promoter containing fragment, and one 3' homology fragment with a terminator integrated into the *S. cerevisiae* genome at the X-3 locus.

Construction of the P64DAT Containing Fragment with tENO2 (Middle Fragment 3)

The linear DNA containing 143 bp homology to the *S. cerevisiae* tENO2 terminator and the pSkTDH3 promoter was PCR amplified from P64DAT synthetic TWIST DNA with primers 1230248 (5'-GGTCT CCTTT CTTTC AAGAA ACACA GTC-3'; SEQ ID NO: 55) and 1230232 (5'-ATGAT GAAAA AATAA GCAGA AAAGA CTAAT AATTC TTAG-3'; SEQ ID NO: 56). Fifty pmoles each of forward and reverse primer was used in a PCR reaction containing 5 ng of plasmid DNA as template, 1× Platinum SuperFi HF Buffer (Thermo Fisher Scienctific), and 2 units SuperFi DNA polymerase in a final volume of 50 μL. The PCR was performed in a T100™ Thermal Cycler (Bio-Rad Laboratories, Inc.) programmed for one cycle at 98° C. for 30 seconds followed by 35 cycles each at 98° C. for 10 seconds, 60° C. for 10 seconds, and 72° C. for 1.5 minutes with a final extension at 72° C. for 5 minutes. Following thermocycling, the PCR reaction products gel isolated and cleaned up using the QIAquick Gel Extraction kit (Qiagen).

Integration of the Left, Middle and Right-Hand Fragments to Generate Yeast Strains with CBH1 and EG2

The yeast S709-A06 was transformed with the left, two middle and right integration fragments described above. In each transformation pool, the left fragment and right fragment with 50 ng of each fragment was used. There was 1 set of the left, two middle, and one right fragment pools used: left fragment 2 (Example 6), middle fragment 1 (Example 7), middle fragment 3 (Example 7), and right fragment 3 (supra), designated Blend 2 master mix. There is also an additional middle fragment consisted of a signal peptide and CBH1 gene and a signal peptide with ~50 ng of each fragment (200 ng total). The synthetic CBH1 DNA fragment contains genes for: P54TVX. To aid homologous recombination of the left, two middle and right fragments at the genomic X-3 sites a plasmid containing MAD7 and guide RNA specific to X-3 (pMIBa647) was also used in the transformation. The one synthetic middle component was combined with the Blend 2 master mix and transformed into the into *S. cerevisiae* strain S709-A06 following a yeast electroporation protocol. Transformants were selected on YPD+cloNAT to select for transformants that contain the Mad7 plasmid pMIBa647. Transformants were either picked manually by hand onto YPD plates or by using a Q-pix Colony Picking System (Molecular Devices) to inoculate 1 well of 96-well plate containing YPD media. The plates were grown for 2 days then glycerol was added to 20% final concentration and the plates were stored at −80° C. until needed. Integration of the CBH1 and EG2 construct was verified by PCR with locus specific primers and subsequent sequencing.

Example 9: Construction of Yeast Strains Expressing an *Aspergillus fumigatus* CBH1 and a *Cladosporium antareticum* Endo-Glucanase This example describes the construction of yeast cells containing a CBH2 under the control of one *S. cerevisiae* promoter: pSeTDH3, which is a strong constitutive promoter. It also contains an EG2 under the control of one *S. cerevisiae* promoter: pSKTDH3. Five pieces of DNA containing promoters, genes and terminators were designed to allow for homologous recombination between the 5 DNA fragments and into the X-3 locus of the yeast S709-A06 (MeJi797 expressing the *A. fumigatus* beta-glucosidase of SEQ ID NO: 8). The resulting strain would have one 5' homology containing fragment with a promoter, 2 promoter and gene containing fragments, 1 terminator and promoter containing fragment, and one 3' homology fragment with a terminator integrated into the *S. cerevisiae* genome at the X-3 locus.

Integration of the Left, Middle and Right-Hand Fragments to Generate Yeast Strains with CBH2 and EG2

The yeast S709-A06 was transformed with the left, two middle and right integration fragments described above. In each transformation pool, the left fragment and right fragment with 50 ng of each fragment was used. There was 1 set of the left, two middle, and one right fragment pools used: left fragment 2 (supra), middle fragment 1 (supra), middle fragment 3 (supra), and right fragment 3 (supra), designated Blend 2 master mix. There is also an additional middle fragment consisted of a signal peptide and CBH2 gene and a signal peptide with ~50 ng of each fragment (200 ng total). The synthetic CBH1 DNA fragment contains genes for: P43VY6. To aid homologous recombination of the left, two middle and right fragments at the genomic X-3 sites a plasmid containing MAD7 and guide RNA specific to X-3

(pMIBa647) was also used in the transformation. The one synthetic middle component was combined with the Blend 2 master mix and transformed into the into *S. cerevisiae* strain S709-A06 following a yeast electroporation protocol. Transformants were selected on YPD+cloNAT to select for transformants that contain the Mad7 plasmid pMIBa647. Transformants were either picked manually by hand onto YPD plates or by using a Q-pix Colony Picking System (Molecular Devices) to inoculate 1 well of 96-well plate containing YPD media. The plates were grown for 2 days then glycerol was added to 20% final concentration and the plates were stored at −80° C. until needed. Integration of the CBH2 and EG2 construct was verified by PCR with locus specific primers and subsequent sequencing. The strains generated in S709-A06 in this example were designated S1130-$B_{11}$ and S1130-$H_{11}$.

Example 10: Evaluation of Yeast Strains Expressing Polypeptides Having Cellobiohydrolase Activity, Endoglucanase Activity, or Beta-Glucosidase Activity Corn Mash Fermentation Procedure Yeast strains described supra were incubated overnight in 50 mL YPD media (6% w/v. D-glucose, 2% peptone, 1% yeast extract) in 125 ml baffled shake flasks at 32° C. at 150 rpm at 32° C. Cells were harvested after 24 hours incubation. Cells were collected by centrifugation and washed in DI water prior to resuspending in 10 mL DI water for dosing. Industrially obtained liquefied corn mash, where liquefaction was carried out using the Fortiva product from Novozymes, was supplemented with 3 ppm penicillin and 500 ppm of urea. Simultaneous saccharification and fermentation (SSF) was performed via mini-scale fermentations. Approximately 4 g of corn mash was added to 15 ml conical tubes. Each tube was dosed with $1\times10^7$ cells/g of mash with one of the yeast strains shown in Table X followed by the addition of 0.42 AGU/g of dry solids of an exogenous glucoamylase enzyme product (Innova Ultra F). Eight replicate tube fermentations were conducted for each yeast strain. Glucoamylase and yeast dosages were administered based on the exact weight of corn slurry in each vial. Tubes were incubated at 32° C. and mixed two to three times per day via brief vortex. After 70 hours fermentation time, tubes were centrifuged @3500 rpm for 5 min. Supernatant samples were filtered with 0.2 μm syringe filters into vials for analysis of final ethanol level via HPLC.

Results

Figure 2:
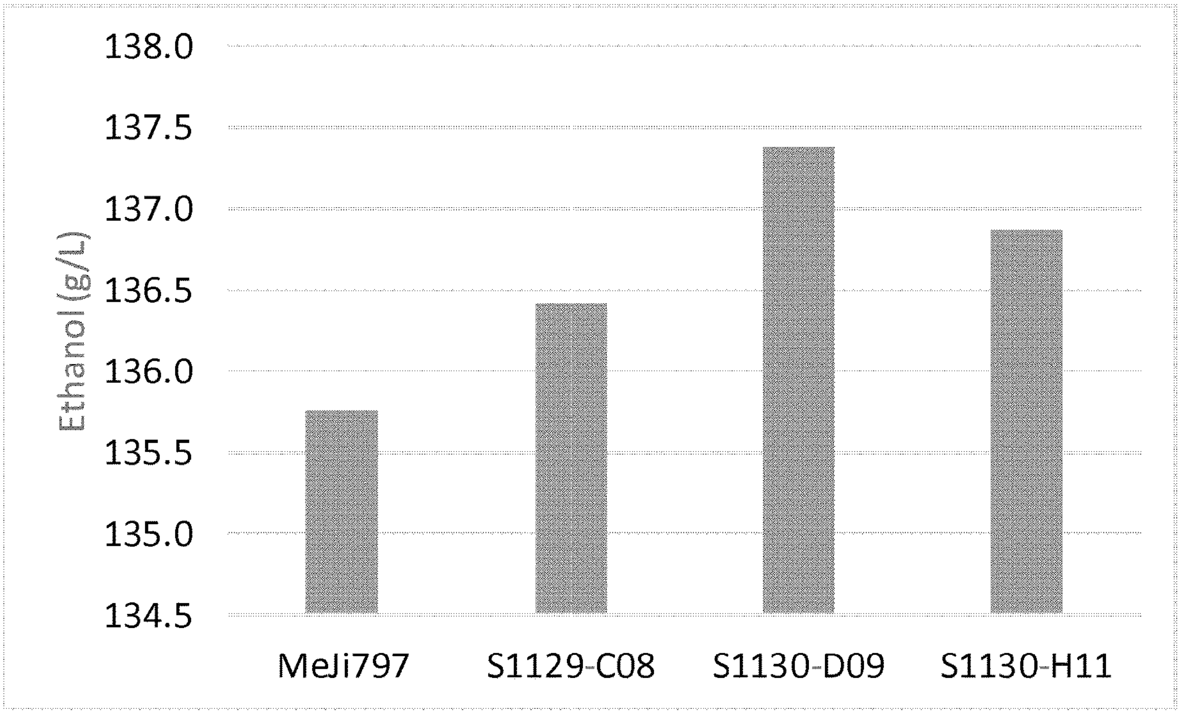
FIG. 2 shows the final ethanol yield following SSF for control strain MeJi797 and strains S1129-C08, S1130-D09 and S11130-H11.

Final ethanol level results from the corn mash fermentation described above are shown in FIGS. 1 and 2. Yeast strain (S833-E04) expressing *T. pinophilus* beta-glucosidase of SEQ ID NO: 6 showed significantly higher ethanol yield as compare to control strain MeJi797. Yeast strain (S1129-C08) expressing the *P. emersonii* cellobiohydrolase of SEQ ID NO: 1+*Trichoderma reesei* endoglucanase of SEQ ID NO: 29+*A. fumigatus* beta-glucosidase of SEQ ID NO: 8 had higher ethanol yield as compare to control strain MeJi797. Yeast strain (S1130-D09) expressing the *A. fumigatus* cellobiohydrolase of SEQ ID NO: 9+*A. fumigatus* beta-glucosidase of SEQ ID NO: 8+*Cladosporium antareticum* endoglucanase of SEQ ID NO: 5 had higher ethanol yield as compare to control strain MeJi797. Yeast strain (S1130-$H_{11}$) expressing the *Talaromyces verruculosus* cellobiohydrolase of SEQ ID NO: 4+*A. fumigatus* beta-glucosidase of SEQ ID NO: 8+*Cladosporium antareticum* endoglucanase of SEQ ID NO: 5 had higher ethanol yield as compare to control strain MeJi797.

Example 11: Evaluation of Ethanol Yield Comparing the Addition an *A. Nidulans* Cellobiohydrolase or *P. emersonii* Cellobiohydrolase to an *A. Fumigatus* Cellobiohydrolase in Simultaneous Saccharification and Fermentation (SSF)

Liquified corn mash was obtained from Show Me Ethanol plant. A 500 ppm urea and 3 ppm penicillin were added, and slurry pH was adjusted to 5.0 (if needed). The % dry solid (DS) of the mash was determined by HX204 moisture analyzer (Mettler Toledo) at 120 C drying temperature. Prior to SSF, the corn mash was weighed at 40 g in each 125 ml bottle.

A day prior to SSF, yeast propagation was carried out by propagating 50 ul MeJi797 cream yeast in 50 ml 6% YPT medium at 32C for about 22 hours. The propagated yeast was centrifuged at 3300 rpm for 5 minutes. The precipitate yeast solid was dissolved with 40 ml deionized water and centrifuging 2nd time, then the precipitate solid was suspended with 7.5 ml deionized water. The yeast counting of the suspended yeast solution was carried out with Nucleo-Counter YC-100 (Chemometec) after 1000× dilution with lysis buffer.

SSF was carried out in three replicates. Enzymes in Table 5 were added accordingly, and the propagated yeast MeJi797 were dosed at 10 million per gram fermentation slurry. The total dry solid of SSF slurry was adjusted to 31% DS with addition of tap water. SSF bottles were placed in an air shaker at 100 rpm and 32 C for 65 hours.

TABLE 5

| Name | Origin | Activity/ Protein Content | unit/ ml | ID |
|---|---|---|---|---|
| Innova Ultra F | Novozymes glucoamylase product | 1450 | AGU/g | NS50527 |
| WA Cellulase Complex | Novozymes product | 285.5 | mgEP/ ml | WAM00001 |
| cellobiohydrolase | *Aspergillus fumigatus* (SEQ ID NO: 9) | 86.36 | mgEP/ ml | P168Y8 |
| cellobiohydrolase | *Aspergillus nidulans* (SEQ ID NO: 2) | 3.3 | mgEP/ ml | P16C21 |
| cellobiohydrolase | *Penicillium emersonii* (SEQ ID NO: 1) | 36 | mgEP/ ml | P244YG |
| Endoglucanase-1 | *Trichoderma reesei* (SEQ ID NO: 29) | 10.68 | mgEP/ ml | P33516 |
| beta-glucosidase | *Aspergillus fumigatus* (SEQ ID NO: 8) | 26.5 | mgEP/ ml | P3EW |
| CBH1&2 double deletion Tr strain | *Trichoderma reesei* | 115.9 | mgEP/ ml | |

After SSF, fermentation bottles were cooled down in 20C water for 15 min. Approximately 5 g fermentation slurry was transferred to each 15 ml tube and fermentation was stopped by adding 50 ul 37% $H_2SO_4$ and mixing well. Tubes were centrifuged at 3000 rpm for 10 minutes. The supernatant was filtered through 0.2 μm syringe filter in a HPLC vial. Ethanol contents were analyzed with Agilent HPLC system.

The ethanol concentrations from SSF are in Table 6 below. Compared to WA cellulase complex or Af CBH1 mix (a mimic WA complex), it's clear that replacing *Aspergillus fumigatus* cellobiohydrolase of SEQ ID NO: 9 with the *Aspergillus nidulans* cellobiohydrolase of SEQ ID NO: 2, or the *Penicillium emersonii* cellobiohydrolase of SEQ ID NO: 1 resulted in higher ethanol yield.

TABLE 6

| No: | Corn mash g | Ultra F (agu/g DS) | WA (ug/g DS) | CBHI (ug/g DS) | Af BG ug/g DS | DD Tr Strain ug/g DS | Average Ethanol g/l | Ethanol STDEV |
|---|---|---|---|---|---|---|---|---|
| 1 | 40 | 0.42 | | | | | 135.9 | 0.98 |
| 2 | 40 | 0.42 | 100 | | | | 136.7 | 0.69 |
| 3 | 40 | 0.42 | | Af CBH1 30 | 20 | 50 | 136.5 | 0.31 |
| 4 | 40 | 0.42 | | An CBH1 30 | 20 | 50 | 137.1 | 0.45 |
| 5 | 40 | 0.42 | | Pe CBH1 30 | 20 | 50 | 137.2 | 0.59 |

Example 12: Evaluation of Ethanol Yield Impact During SSF for the Addition of a *Cladosporium Antareticum* Endoglucanase A 500 ppm urea and 3 ppm penicillin was added to liquified corn mash, and the slurry was pH adjusted to 5.0. The % dry solid (DS) of the mash was determined by HX204 moisture analyzer (Mettler Toledo) at 120C drying temperature. Prior to SSF, the corn mash was pipetted at 3.75 ml (4 g) in each 12 ml tube.

A day prior to SSF, yeast propagation was carried out by propagating 50 ul MeJi797 cream yeast in 50 ml 6% YPT medium at 32C for about 22 hours. The propagated yeast was centrifuged at 3300 rpm for 5 minutes. The precipitate yeast solid was dissolved with 40 ml deionized water and centrifuged a 2nd time, then the precipitate solid was suspended with 7.5 ml deionized water. The yeast counting of the suspended yeast solution was carried out with NucleoCounter YC-100 (Chemometec) after 1000× dilution with lysis buffer.

SSF was carried out in six replicates. Enzymes in Table 7 were added accordingly to Table 8, and the propagated Innova Force yeast were dosed at 10 million per gram fermentation slurry. And the total dry solid of SSF slurry was adjusted to 33.5% DS with addition of tap water. SSF tubes were placed in 32C constant temperature chamber for 66 hours, tubes were vortexed once a day.

TABLE 7

| No | Name | Origin | Activity (unit) | | P# |
|---|---|---|---|---|---|
| 1 | Innova Ultra F | Novozymes glucoamylase product | 1450 | AGU/g | |
| 2 | WA cellulase complex | Novozymes product | 285.5 | mgEP/ml | WAM00001 |
| 3 | Endoglucanase-1 | *Trichoderma reesei* (SEQ ID NO: 29) | 10.68 | mgEP/ml | P33516 |
| 4 | Endoglucanase-2 | *Trichoderma reesei* (SEQ ID NO: 57) | 9.21 | mgEP/ml | P24KEK |
| 5 | Endoglucanase-2 | *Cladosporium antareticum* (SEQ ID NO: 5) | 7.3 | mgEP/ml | P64DAT |
| 6 | cellobiohydrolase | *Aspergillus fumigatus* (SEQ ID NO: 9) | 86.36 | mgEP/ml | P3EX |
| 7 | cellobiohydrolase | *Penicillium emersonii* (SEQ ID NO: 1) | 36 | mgEP/ml | P244YG |
| 8 | cellobiohydrolase | *Aspergillus nidulans* (SEQ ID NO: 2) | 3.3 | mgEP/ml | P16C21 |
| 9 | beta-glucosidase | *Aspergillus fumigatus* (SEQ ID NO: 58) | 26.5 | mgEP/ml | P23VYK |
| 9 | beta-glucosidase | *Talaromyces pinophilus* (SEQ ID NO: 6) | 2.7 | mgEP/ml | P23WFT |
| 10 | QD Tr Strain | *Trichoderma reesei* | 34.7 | mgEP/ml | |

Note:
QD Tr Strain is *Trichoderma reesei* strain with gene deletion of EG1, GH11 xylanase, CBH1 and CBH2.

TABLE 8

| | Ultra F AGU/g | Tr EG1 ug/g DS | Tr EG2 ug/g DS | Ca EG2 ug/g DS | Af CBHI ug/g DS | Pe CBH1 ug/g DS | An CBH1 ug/g DS | Af BG4M ug/g DS | QD Tr Strain ug/g DS |
|---|---|---|---|---|---|---|---|---|---|
| 1 | 0.42 | | | | | | | | |
| 2 | 0.42 | 5 | | | 15 | | | 10 | 15 |
| 3 | 0.42 | 5 | 5 | | 15 | | | 10 | 15 |
| 4 | 0.42 | 5 | | 5 | 15 | | | 10 | 15 |
| 5 | 0.42 | 5 | | | | 15 | | 10 | 15 |
| 6 | 0.42 | 5 | 5 | | | 15 | | 10 | 15 |
| 7 | 0.42 | 5 | | 5 | | 15 | | 10 | 15 |
| 8 | 0.42 | 5 | | | | | 15 | 10 | 15 |
| 9 | 0.42 | 5 | 5 | | | | 15 | 10 | 15 |
| 10 | 0.42 | 5 | | 5 | | | 15 | 10 | 15 |

After SSF, fermentation tubes were cooled down in 20C water for 15 min. The fermentation was stopped by adding 50 ul 38% $H_2SO_4$ in each tube and mixing well. Tubes were centrifuged at 3000 rpm for 10 minutes. The supernatant was filtered through 0.2 μm syringe filter in a HPLC vial. Ethanol contents were analyzed with Agilent HPLC system.

The ethanol concentrations from SSF are in Table 9 below. The results show that the addition of any CBH1 cellulase mix resulted in higher ethanol yield compared to no cellulase control. The addition of either *Trichoderma reesei* endoglucanase-2 of SEQ ID NO: 57, or *Cladosporium antareticum* endoglucanase-2 of SEQ ID NO: 5 increased the ethanol yield compared to without the endoglucanase-2. The addition of *Cladosporium antareticum* endoglucanase-2 of SEQ ID NO: 5 in each cellobiohydrolase cellulase mixture resulted the highest ethanol yield.

TABLE 9

| | Average | | | | STDEV | | | |
|---|---|---|---|---|---|---|---|---|
| | no Cellulase | w/o EG2 | w/Tr EG2 | w/Ca EG2 | no Cellulase | w/o EG2 | w/Tr EG2 | w/Ca EG2 |
| UF w/o cellulase | 138.84 | | | | 0.69 | | | |
| UF + Af CBH1 Mix | | 139.04 | 139.43 | 139.76 | | 0.49 | 0.55 | 0.65 |
| UF + Pe CBH1 Mix | | 139.25 | 139.45 | 139.68 | | 0.37 | 0.53 | 0.66 |
| UF + An CBH1 Mix | | 139.25 | 139.35 | 140.02 | | 0.77 | 0.64 | 0.20 |

Example 13: Evaluation of Ethanol Yield Impact During SSF with the Addition of a *Talaromyces Pinophilus* Beta-Glucosidase A 500 ppm urea and 3 ppm penicillin was added to liquified corn mash, and the slurry was pH adjusted to 5.0. The % dry solid (DS) of the mash was determined by HX204 moisture analyzer (Mettler Toledo) at 120C drying temperature. Prior to SSF, the corn mash was weighed at 40 g in each 125 ml bottle.

A day prior to SSF, yeast propagation was carried out by propagating 50 ul MeJi797 cream yeast in 50 ml 6% YPT medium at 32C for about 22 hours. The propagated yeast was centrifuged at 3300 rpm for 5 minutes. The precipitate yeast solid was dissolved with 40 ml deionized water and centrifuging 2nd time, then the precipitate solid was suspended with 7.5 ml deionized water. The yeast counting of the suspended yeast solution was carried out with NucleoCounter YC-100 (Chemometec) after 1000× dilution with lysis buffer.

SSF was carried out in three replicates. Enzymes of Table 10 below were added accordingly, and the propagated Innova Force yeast were dosed at 10 million per gram fermentation slurry. And the total dry solid of SSF slurry was adjusted to 34.5% DS with addition of tap water. SSF bottles were placed in an air shaker at 100 rpm and 32 C for 66 hours.

TABLE 10

| No | Name | Origin | Activity (unit) | | ID |
|---|---|---|---|---|---|
| 1 | Innova Ultra F | Novozymes glucoamylase product | 1450 | AGU/g | NS50527 |
| 2 | cellobiohydrolase | *Aspergillus fumigatus* (SEQ ID NO: 9) | 86.36 | mgEP/ml | P3EX |
| 3 | cellobiohydrolase | *Penicillium emersonii* (SEQ ID NO: 1) | 36 | mgEP/ml | P244YG |
| 4 | Endoglucanase-1 | *Trichoderma reesei* (SEQ ID NO: 29) | 10.68 | mgEP/ml | P33516 |
| 5 | Endoglucanase-2 | *Cladosporium antareticum* (SEQ ID NO: 5) | 7.3 | mgEP/ml | P64DAT |
| 6 | QD Tr Strain | *Trichoderma reesei* | 34.7 | mgEP/ml | |
| 7 | beta-glucosidase | *Aspergillus fumigatus* (SEQ ID NO: 58) | 26.5 | mgEP/ml | P23VYK |
| 8 | beta-glucosidase | *Talaromyces pinophilus* (SEQ ID NO: 6) | 2.7 | mgEP/ml | P23WFT |

Note:
QD Tr Strain is *Trichoderma reesei* strain with gene deletion of EG1, GH11 xylanase, CBH1 and CBH2.

After SSF, fermentation bottles were cooled down in 20C water for 15 min. Approximately 5 g fermentation slurry was transferred to each 15 ml tube and fermentation was stopped by adding 50 ul 38% $H_2SO_4$ and mixing well. Tubes were centrifuged at 3000 rpm for 10 minutes. The supernatant was filtered through 0.2 μm syringe filter in a HPLC vial. Ethanol contents were analyzed with Agilent HPLC system.

The ethanol concentrations from SSF are in Table 11 below. By replacing *Aspergillus fumigatus* beta-glucosidase of SEQ ID NO: 58 with the *Talaromyces pinophilus* beta-glucosidase in-two different cellobiohydrolase cellulase mixtures, a higher ethanol yield was observed.

TABLE 11

| Corn mash g | Ultra F agu/g DS | CBHI (ug/g DS) | Af BG4M ug/g DS | Tb BG ug/g DS | QD Tr ug/g DS | Tr EG1 ug/g DS | Ca EG2 ug/g DS | Average Ethanol g/l | STDEV Ethanol |
|---|---|---|---|---|---|---|---|---|---|
| 40 | 0.42 | AfCBH1 30 | 20 | | 30 | 10 | 10 | 141.45 | 0.54 |
| 40 | 0.42 | PeCBH1 30 | 20 | | 30 | 10 | 10 | 141.62 | 0.28 |
| 40 | 0.42 | AfCBH1 30 | | 20 | 30 | 10 | 10 | 141.57 | 0.44 |
| 40 | 0.42 | PeCBH1 30 | | 20 | 30 | 10 | 10 | 141.88 | 0.38 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Example 14

Figure 3:
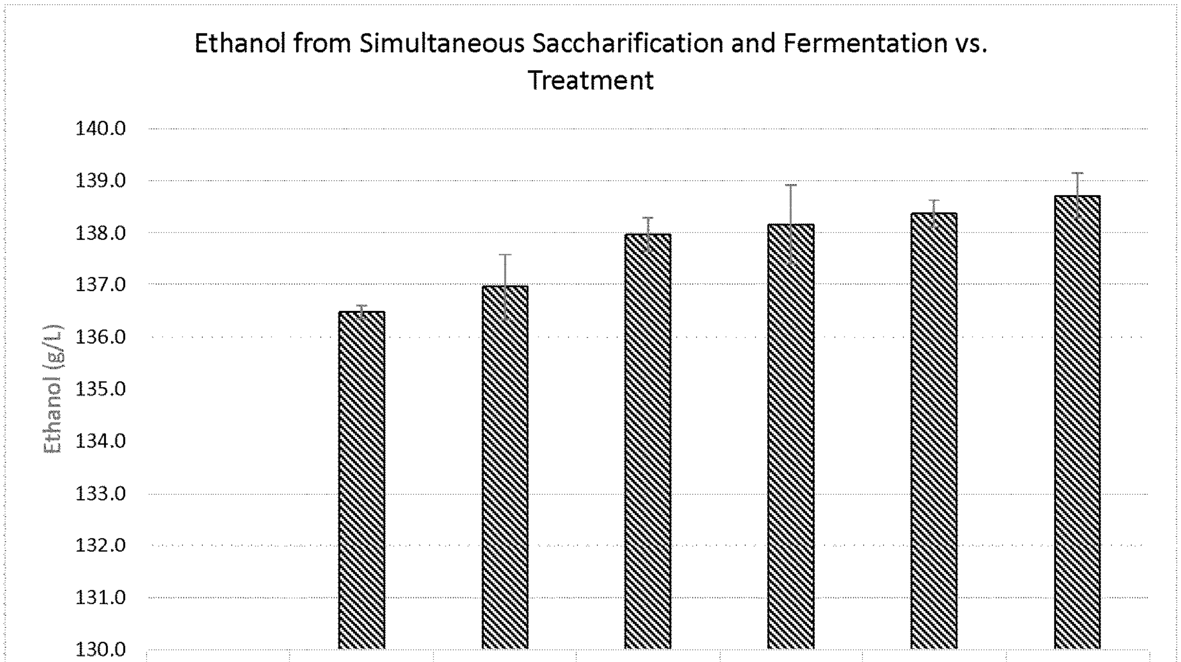
FIG. 3 shows the ethanol yield from synergistic blends of GH10 xylanase and GH62 arabinofuranosidase in simultaneous saccharification and fermentation with a cellulolytic composition.

This example illustrates the synergy between an enzyme blend comprising a GH10 xylanase and GH62 arabinofuranosidase enhances the ethanol yield during simultaneous saccharification and fermentation in conjunction with a cellulolytic composition derived from *Trichoderma reesei* and a glucoamylase blend. Simultaneous saccharification and fermentation (SSF) was performed using industrial corn mash liquefied using Alpha-amylase blend X (Novozymes A/S). An industrial yeast strain (Ethanol Red; Lesaffre) was cultivated for 18 hours in standard YPD media containing 6% glucose at 32° C. and 120 RPM. After the cultivation the yeast propagation was centrifuged, the supernatant decanted, and the yeast cells resuspended in deionized water. The resuspended cells were enumerated using a NucleoCounter YC-100 (ChemoMetric, Allerod, Denmark). The corn mash. was supplemented with 500 ppm of urea and dosed with 0.42 AGU/g-DS of an exogenous glucoamylase blend (Glucoamylase Blend A; Novozymes A/S) and/or 50-100 μg/g-DS of an exogenous Cellulolytic Composition (Novozymes A/S), and/or 25-50 μg/g-DS of an exogenous xylanase product containing a GH10 xylanase (Novozymes A/S), and/or 25-50 μg/g-DS of an exogenous xylanase product containing a GH62 arabinofuranosidase (Novozymes A/S). Approximately 50 g of corn mash with a solids content of 34.5% wt. dry solids was dispensed into a 250 ml glass media bottle (Thermo Fisher Scientific, Hampton, NH) for each sample, followed by the addition of approximately 10^8 yeast cells/g of corn mash from the overnight culture. Bottles were. incubated at 32° C. on an orbital shaker at 150 RPM for 52 hr. Fermentation was stopped by the addition of 500 μL of 42% sulfuric acid followed by centrifugation at 3000 RPM for 10 minutes. The supernatant was analyzed for ethanol using HPLC-RID. The fermentation results with the combination of Cellulolytic Composition, GH10 xylanase, and GH62 arabinofuranosidase is shown in FIG. 3.

Example 15

Figure 4:
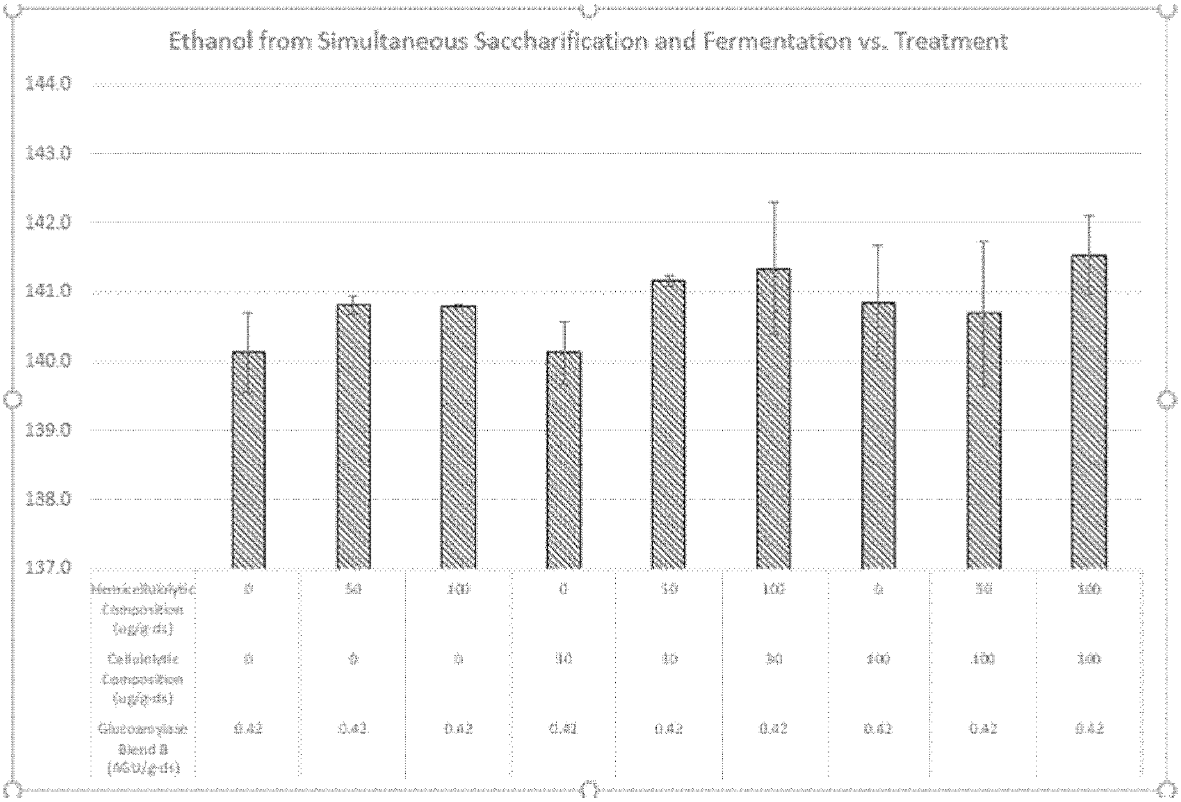
FIG. 4 shows the ethanol yield from an increasing dose of a hemicelluloytic composition comprising GH10 xylanase and GH62 arabinofuranosidase in simultaneous saccharification and fermentation with a cellulolytic composition.

This example illustrates the synergy between an enzyme blend comprising a GH10 xylanase and GH62 arabinofuranosidase enhances the ethanol yield during simultaneous saccharification and fermentation in conjunction with a cellulolytic composition derived from *Trichoderma reesei* and a glucoamylase blend. Simultaneous saccharification and fermentation (SSF) was performed using industrial corn mash liquified using Alpha-amylase blend X (Novozymes A/S). An industrial yeast *Saccharomyces* strain MEJI797 (Novozymes A/S) was cultivated for 18 hours in standard YPD media containing 6% glucose at 32° C. and 120 RPM. After the cultivation the yeast propagation was centrifuged, the supernatant decanted, and the yeast cells resuspended in deionized water. The resuspended cells were enumerated using a NucleoCounter YC-100 (ChemoMetric, Allerod, Denmark). The corn mash was supplemented with 500 ppm of urea and dosed with 0.42 AGU/g-DS of an exogenous glucoamylase blend (Glucoamylase Blend B; Novozymes A/S) and/or 50-100 μg/g-DS of an exogenous Cellulolytic Composition (Novozymes A/S), and/or 50-100 μg/g-DS of an exogenous xylanase product containing a GH10 xylanase and GH62 arabinofuranosidase (Hemicellulolytic Composition; Novozymes A/S). Approximately 50 g of corn mash with a solids content of 33.0% wt. dry solids was dispensed into a 250 ml glass media bottle (Thermo Fisher Scientific, Hampton, NH) for each sample, followed by the addition of approximately 10^8 yeast cells/g of corn mash from the overnight culture. Bottles were incubated at 32° C. on an orbital shaker at 150 RPM for 68 hr. Fermentation was stopped by the addition of 500 μL of 42% sulfuric acid followed by centrifugation at 3000 RPM for 10 minutes. The supernatant was analyzed for ethanol using HPLC-RID. The fermentation results with the combination of Cellulolytic Composition and Hemicellulolytic Composition is shown in FIG. 4.

The invention claimed is:

1. A process for producing a fermentation product from starch-containing material, the process comprising the steps of:

i) liquefying the starch-containing material at a temperature above the initial gelatinization temperature using an alpha-amylase;

ii) saccharifying the liquefied starch-containing;

iii) fermenting saccharified starch-containing material using a fermenting organism;

wherein at least one polypeptide having cellobiohydrolase activity, endoglucanase activity, or beta-glucosidase activity is present or added during fermentation; and wherein the at least one polypeptide is selected from the group consisting of:

(i) a polypeptide having cellobiohydrolase activity and at least 90% identity to the mature polypeptide of SEQ ID NO: 3;

(ii) a polypeptide having endoglucanase activity and at least 90% identity to the mature polypeptide of SEQ ID NO: 5;

(iii) a polypeptide having cellobiohydrolase activity and at least 99% identity to the mature polypeptide of SEQ ID NO: 4; and (iv) a polypeptide having beta-glucosidase activity and and an amino acid sequence that comprises or consists of the mature polypeptide of SEQ ID NO: 6.

2. The process of claim 1, wherein the at least one polypeptide having cellobiohydrolase activity, endoglucanase activity, or beta-glucosidase activity comprises or consists of the mature polypeptide of SEQ ID NO: 3, SEQ ID NO: 5, SEQ ID NO: 4, or SEQ ID NO: 6.

3. The process of claim 1, wherein the at least one polypeptide having cellobiohydrolase activity, endoglucanase activity, or beta-glucosidase activity is a fragment of SEQ ID NO: 3 having cellobiohydrolase activity, or a fragment of SEQ ID NO: 5 having endoglucanase activity.

4. The process of claim 1, wherein the at least one polypeptide is selected from the group consisting of:

(i) a polypeptide having cellobiohydrolase activity and at least 95% identity to the mature polypeptide of SEQ ID NO: 3; and (ii) a polypeptide having endoglucanase activity and at least 95% identity to the mature polypeptide of SEQ ID NO: 5.

5. The process of claim 1, wherein the at least one polypeptide is selected from the group consisting of:

(i) a polypeptide having cellobiohydrolase activity and at least 98% identity to the mature polypeptide of SEQ ID NO: 3; and (ii) a polypeptide having endoglucanase activity and at least 98% identity to the mature polypeptide of SEQ ID NO: 5.

6. A nucleic acid construct or expression vector comprising a polynucleotide encoding a polypeptide, wherein the polynucleotide is operably linked to one or more control sequences that direct the production of the polypeptide in an expression host, and wherein the polypeptide is selected from the group consisting of:

a polypeptide having cellobiohydrolase activity and at least 90% identity to the mature polypeptide of SEQ ID NO: 3;

a polypeptide having cellobiohydrolase activity and at least 99% identity to the mature polypeptide of SEQ ID NO: 4;

a polypeptide having endoglucanase activity and at least 90% identity to the mature polypeptide of SEQ ID NO: 5; and a polypeptide having beta-glucosidase activity and an amino acid sequence that comprises or consists of the mature polypeptide of SEQ ID NO: 6.

7. The nucleic acid construct or expression vector of claim 6 wherein the polypeptide has cellobiohydrolase activity and at least 95% identity to the mature polypeptide of SEQ ID NO: 3.

8. The nucleic acid construct or expression vector of claim 6, wherein the polypeptide has cellobiohydrolase activity and at least 98% identity to the mature polypeptide of SEQ ID NO: 3.

9. The nucleic acid construct or expression vector of claim 6, wherein the polypeptide has cellobiohydrolase activity and an amino acid sequence that comprises or consists of the mature polypeptide of SEQ ID NO: 3.

10. The nucleic acid construct or expression vector of claim 6, wherein the polypeptide has cellobiohydrolase activity and is a variant of the mature polypeptide of SEQ ID NO: 3 comprising a substitution, deletion, or insertion at one or more positions.

11. The nucleic acid construct or expression vector of claim 6, wherein the polypeptide is a fragment of SEQ ID NO: 3 having cellobiohydrolase activity.

12. The nucleic acid construct or expression vector of claim 6, wherein the polypeptide has cellobiohydrolase activity and an amino acid sequence that comprises or consists of the mature polypeptide of SEQ ID NO: 4.

13. The nucleic acid construct or expression vector of claim 6, wherein the polypeptide has cellobiohydrolase activity and is a variant of the mature polypeptide of SEQ ID NO: 4 comprising a substitution, deletion, or insertion at one or more positions.

14. The nucleic acid construct or expression vector of claim 6, wherein the polypeptide has endoglucanase activity and at least 95% identity to the mature polypeptide of SEQ ID NO: 5.

15. The nucleic acid construct or expression vector of claim 6, wherein the polypeptide has endoglucanase activity and at least 98% identity to the mature polypeptide of SEQ ID NO: 5.

16. The nucleic acid construct or expression vector of claim 6, wherein the polypeptide has endoglucanase activity and an amino acid sequence comprising of consisting that comprises or consists of the mature polypeptide of SEQ ID NO: 5.

17. The nucleic acid construct or expression vector of claim 6, wherein the polypeptide has endoglucanase activity and is a variant of the mature polypeptide of SEQ ID NO: 5 comprising a substitution, deletion, or insertion at one or more positions.

18. The nucleic acid construct or expression vector of claim 6, wherein the polypeptide has beta-glucosidase activity and an amino acid sequence that comprises or consists of the mature polypeptide of SEQ ID NO: 6.

19. An isolated transformed host cell comprising at least one heterologous polynucleotide encoding a polypeptide selected from the group consisting of:

(i) a polypeptide having cellobiohydrolase activity and at least 90% identity to the mature polypeptide of SEQ ID NO: 3;

(ii) a polypeptide having endoglucanase activity and at least 90% identity to the mature polypeptide of SEQ ID NO: 5;

(iii) a polypeptide having cellobiohydrolase activity and at least 99% identity to the mature polypeptide of SEQ ID NO: 4; and (iv) a polypeptide having beta-glucosidase activity and an amino acid sequence that comprises or consists of the mature polypeptide of SEQ ID NO: 6.

20. The isolated transformed host cell of claim 19, wherein the polypeptide comprises or consists of the mature polypeptide of SEQ ID NO: 3, SEQ ID NO: 5.

21. The isolated transformed host cell of claim 19, wherein the polypeptide is a fragment of SEQ ID NO: 3 having cellobiohydrolase activity, or a fragment of SEQ ID NO: 5 having endoglucanase activity.

22. The isolated transformed host cell of claim 19, wherein the polypeptide is selected from the group consisting of:

(i) a polypeptide having cellobiohydrolase activity and at least 95% identity to the mature polypeptide of SEQ ID NO: 3; and (ii) a polypeptide having endoglucanase activity and at least 95% identity to the mature polypeptide of SEQ ID NO: 5.

23. The isolated transformed host cell of claim 19, wherein the polypeptide is selected from the group consisting of:

(i) a polypeptide having cellobiohydrolase activity and at least 98% identity to the mature polypeptide of SEQ ID NO: 3; and (ii) a polypeptide having endoglucanase activity and at least 98% identity to the mature polypeptide of SEQ ID NO: 5.

24. The isolated transformed host cell of claim 19, wherein the cell further comprises a heterologous polynucleotide encoding a glucoamylase.

25. The isolated transformed host cell of claim 19, wherein the cell further comprises a heterologous polynucleotide encoding an alpha-amylase.

26. The isolated transformed host cell of claim 19, wherein the cell is a yeast cell.

27. The isolated transformed host cell of claim 26, wherein the cell is a *Saccharomyces cerevisiae* cell.

28. A method of producing a polypeptide having cellobiohydrolase activity, endoglucanase activity, or beta-glucosidase activity, said method comprising:

(a) cultivating the isolated transformed host cell of claim 19 under conditions conducive for production of the polypeptide; and (b) recovering the polypeptide.

29. The isolated transformed host cell of claim 19, wherein the polypeptide has cellobiohydrolase activity and an amino acid sequence that comprises or consists of the mature polypeptide of SEQ ID NO: 3.

30. The isolated transformed host cell of claim 19, wherein the polypeptide has cellobiohydrolase activity and an amino acid sequence that comprises or consists of the mature polypeptide of SEQ ID NO: 4.

31. The isolated transformed host cell of claim 19, wherein the polypeptide has endoglucanase activity and an amino acid sequence that comprises or consists of the mature polypeptide of SEQ ID NO: 5.

32. The isolated transformed host cell of claim 19, wherein the polypeptide has beta-glucanase activity and an amino acid sequence that comprises or consists of the mature polypeptide of SEQ ID NO: 6.

* * * * *

SEQUENCE LISTING

<160> NUMBER OF SEQ ID NOS: 60

<210> SEQ ID NO 1
<211> LENGTH: 520
<212> TYPE: PRT
<213> ORGANISM: Penicillium emersonii

<400> SEQUENCE: 1

Met Leu Arg Arg Ala Leu Leu Leu Ser Ser Ser Ala Ile Leu Ala Val
1 5 10 15

Lys Ala Gln Gln Ala Gly Thr Ala Thr Ala Glu Asn His Pro Pro Leu
20 25 30

Thr Trp Gln Glu Cys Thr Ala Pro Gly Ser Cys Thr Thr Gln Asn Gly
35 40 45

Ala Val Val Leu Asp Ala Asn Trp Arg Trp Val His Asp Val Asn Gly
50 55 60

Tyr Thr Asn Cys Tyr Thr Gly Asn Thr Trp Asn Pro Thr Tyr Cys Pro
65 70 75 80

Asp Asp Glu Thr Cys Ala Gln Asn Cys Ala Leu Asp Gly Ala Asp Tyr
85 90 95

Glu Gly Thr Tyr Gly Val Thr Ser Ser Gly Ser Ser Leu Lys Leu Asn
100 105 110

Phe Val Thr Gly Ser Asn Val Gly Ser Arg Leu Tyr Leu Leu Gln Asp
115 120 125

Asp Ser Thr Tyr Gln Ile Phe Lys Leu Leu Asn Arg Glu Phe Thr Phe
130 135 140

Asp Val Asp Val Ser Asn Leu Pro Cys Gly Leu Asn Gly Ala Leu Tyr
145 150 155 160

Phe Val Ala Met Asp Ala Asp Gly Gly Val Ser Lys Tyr Pro Asn Asn
165 170 175

Lys Ala Gly Ala Lys Tyr Gly Thr Gly Tyr Cys Asp Ser Gln Cys Pro
180 185 190

Arg Asp Leu Lys Phe Ile Asp Gly Glu Ala Asn Val Glu Gly Trp Gln
195 200 205

Pro Ser Ser Asn Asn Ala Asn Thr Gly Ile Gly Asp His Gly Ser Cys
210 215 220

Cys Ala Glu Met Asp Val Trp Glu Ala Asn Ser Ile Ser Asn Ala Val
225 230 235 240

Thr Pro His Pro Cys Asp Thr Pro Gly Gln Thr Met Cys Ser Gly Asp
245 250 255

Asp Cys Gly Gly Thr Tyr Ser Asn Asp Arg Tyr Ala Gly Thr Cys Asp
260 265 270

Pro Asp Gly Cys Asp Phe Asn Pro Tyr Arg Met Gly Asn Thr Ser Phe
275 280 285

Tyr Gly Pro Gly Lys Ile Ile Asp Thr Thr Lys Pro Phe Thr Val Val
290 295 300

Thr Gln Phe Leu Thr Asp Asp Gly Thr Asp Thr Gly Thr Leu Ser Glu
305 310 315 320

Ile Lys Arg Phe Tyr Val Gln Asn Gly Asn Val Ile Pro Gln Pro Asn
325 330 335

Ser Asp Ile Ser Gly Val Thr Gly Asn Ser Ile Thr Thr Glu Phe Cys
340 345 350

Thr Ala Gln Lys Gln Ala Phe Gly Asp Thr Asp Asp Phe Ser Gln His
355 360 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Ser Asn Pro Gly Gly Gly Thr Thr Thr
    450                 455                 460

Thr Thr Thr Thr Gln Pro Thr Thr Thr Thr Thr Thr Ala Gly Asn Pro
465                 470                 475                 480

Gly Gly Thr Gly Val Ala Gln His Tyr Gly Gln Cys Gly Gly Ile Gly
                485                 490                 495

Trp Thr Gly Pro Thr Thr Cys Ala Ser Pro Tyr Thr Cys Gln Lys Leu
            500                 505                 510

Asn Asp Tyr Tyr Ser Gln Cys Leu
        515                 520

<210> SEQ ID NO 2
<211> LENGTH: 503
<212> TYPE: PRT
<213> ORGANISM: Aspergillus nidulans

<400> SEQUENCE: 2

Gln Lys Val Gly Thr Gln Gln Ala Glu Val His Pro Gly Leu Thr Trp
1               5                   10                  15

Gln Thr Cys Thr Ser Ser Gly Ser Cys Thr Thr Val Asn Gly Glu Val
            20                  25                  30

Thr Ile Asp Ala Asn Trp Arg Trp Leu His Thr Val Asn Gly Tyr Thr
        35                  40                  45

Asn Cys Tyr Thr Gly Asn Glu Trp Asp Thr Ser Ile Cys Thr Ser Asn
    50                  55                  60

Glu Val Cys Ala Glu Gln Cys Ala Val Asp Gly Ala Asn Tyr Ala Ser
65                  70                  75                  80

Thr Tyr Gly Ile Thr Thr Ser Gly Ser Ser Leu Arg Leu Asn Phe Val
                85                  90                  95

Thr Gln Ser Gln Gln Lys Asn Ile Gly Ser Arg Val Tyr Leu Met Asp
            100                 105                 110

Asp Glu Asp Thr Tyr Thr Met Phe Tyr Leu Leu Asn Lys Glu Phe Thr
        115                 120                 125

Phe Asp Val Asp Val Ser Glu Leu Pro Cys Gly Leu Asn Gly Ala Val
    130                 135                 140

Tyr Phe Val Ser Met Asp Ala Asp Gly Gly Lys Ser Arg Tyr Ala Thr
145                 150                 155                 160

Asn Glu Ala Gly Ala Lys Tyr Gly Thr Gly Tyr Cys Asp Ser Gln Cys
                165                 170                 175

Pro Arg Asp Leu Lys Phe Ile Asn Gly Val Ala Asn Val Glu Gly Trp
            180                 185                 190

Glu Ser Ser Asp Thr Asn Pro Asn Gly Gly Val Gly Asn His Gly Ser
        195                 200                 205

Cys Cys Ala Glu Met Asp Ile Trp Glu Ala Asn Ser Ile Ser Thr Ala
    210                 215                 220

```
Phe Thr Pro His Pro Cys Asp Thr Pro Gly Gln Thr Leu Cys Thr Gly
225                 230                 235                 240

Asp Ser Cys Gly Gly Thr Tyr Ser Asn Asp Arg Tyr Gly Gly Thr Cys
            245                 250                 255

Asp Pro Asp Gly Cys Asp Phe Asn Ser Tyr Arg Gln Gly Asn Lys Thr
            260                 265                 270

Phe Tyr Gly Pro Gly Leu Thr Val Asp Thr Asn Ser Pro Val Thr Val
        275                 280                 285

Val Thr Gln Phe Leu Thr Asp Asp Asn Thr Asp Thr Gly Thr Leu Ser
    290                 295                 300

Glu Ile Lys Arg Phe Tyr Val Gln Asn Gly Val Val Ile Pro Asn Ser
305                 310                 315                 320

Glu Ser Thr Tyr Pro Ala Asn Pro Gly Asn Ser Ile Thr Thr Glu Phe
            325                 330                 335

Cys Glu Ser Gln Lys Glu Leu Phe Gly Asp Val Asp Val Phe Ser Ala
            340                 345                 350

His Gly Gly Met Ala Gly Met Gly Ala Ala Leu Glu Gln Gly Met Val
        355                 360                 365

Leu Val Leu Ser Leu Trp Asp Asp Asn Tyr Ser Asn Met Leu Trp Leu
    370                 375                 380

Asp Ser Asn Tyr Pro Thr Asp Ala Asp Pro Thr Gln Pro Gly Ile Ala
385                 390                 395                 400

Arg Gly Thr Cys Pro Thr Asp Ser Gly Val Pro Ser Glu Val Glu Ala
            405                 410                 415

Gln Tyr Pro Asn Ala Tyr Val Val Tyr Ser Asn Ile Lys Phe Gly Pro
            420                 425                 430

Ile Gly Ser Thr Phe Gly Asn Gly Gly Gly Ser Gly Pro Thr Thr Thr
        435                 440                 445

Val Thr Thr Ser Thr Ala Thr Ser Thr Thr Ser Ser Ala Thr Ser Thr
    450                 455                 460

Ala Thr Gly Gln Ala Gln His Trp Glu Gln Cys Gly Gly Asn Gly Trp
465                 470                 475                 480

Thr Gly Pro Thr Val Cys Ala Ser Pro Trp Ala Cys Thr Val Val Asn
            485                 490                 495

Ser Trp Tyr Ser Gln Cys Leu
            500


<210> SEQ ID NO 3
<211> LENGTH: 533
<212> TYPE: PRT
<213> ORGANISM: Penicillium swiecickii

<400> SEQUENCE: 3

Met Ala Ser Thr Leu Ser Phe Asn Ile Tyr Lys Asn Ala Leu Leu Phe
1               5                   10                  15

Ala Ala Phe Leu Gly Ala Ala Lys Ala Gln Gln Val Gly Thr Asn Thr
            20                  25                  30

Ala Glu Val His Pro Ser Leu Thr Trp Gln Lys Cys Thr Ala Gly Gly
        35                  40                  45

Thr Cys Thr Ser Gln Ser Gly Lys Val Val Val Asp Ala Asn Trp Arg
    50                  55                  60

Trp Leu His Ser Thr Ser Gly Ser Thr Asn Cys Tyr Thr Gly Asn Thr
65                  70                  75                  80

Trp Asp Ala Thr Leu Cys Pro Asp Asp Val Thr Cys Ala Thr Asn Cys
```

```
                85                  90                  95

Ala Leu Asp Gly Ala Asp Tyr Thr Gly Thr Tyr Gly Val Thr Ala Ser
            100                 105                 110

Gly Ser Ser Leu Arg Leu Asn Phe Val Thr Thr Ala Ser Gln Lys Asn
        115                 120                 125

Ile Gly Ser Arg Leu Tyr Leu Met Glu Asn Asp Thr Lys Tyr Gln Met
    130                 135                 140

Phe Gln Leu Leu Asn Gln Glu Phe Thr Phe Asp Val Asp Val Ser Asn
145                 150                 155                 160

Leu Pro Cys Gly Leu Asn Gly Ala Leu Tyr Phe Val Ser Met Asp Ser
                165                 170                 175

Asp Gly Gly Met Ala Arg Tyr Pro Ala Asn Lys Ala Gly Ala Lys Tyr
            180                 185                 190

Gly Thr Gly Tyr Cys Asp Ser Gln Cys Pro Arg Asp Leu Lys Phe Ile
        195                 200                 205

Asn Gly Gln Ala Asn Val Glu Gly Trp Val Pro Ser Ser Asn Asp Val
    210                 215                 220

Asn Ala Gly Thr Gly Asn His Gly Ser Cys Cys Ala Glu Met Asp Ile
225                 230                 235                 240

Trp Glu Ala Asn Ser Ile Ser Asn Ala Val Thr Pro His Pro Cys Asp
                245                 250                 255

Thr Pro Thr Gln Val Gln Cys Thr Gly Asp Ala Cys Gly Gly Thr Tyr
            260                 265                 270

Ser Ser Asp Arg Tyr Gly Gly Thr Cys Asp Pro Asp Gly Cys Asp Phe
        275                 280                 285

Asn Pro Tyr Arg Gln Gly Asn Gln Ser Phe Tyr Gly Pro Ser Lys Ile
    290                 295                 300

Val Asp Thr Thr Ser Pro Phe Thr Val Val Thr Gln Phe Ile Thr Asn
305                 310                 315                 320

Asp Gly Thr Ser Thr Gly Thr Leu Ser Glu Ile Lys Arg Phe Tyr Val
                325                 330                 335

Gln Asn Gly Lys Val Ile Pro Gln Ser Val Ser Thr Ile Ser Ala Val
            340                 345                 350

Ser Gly Asn Ser Ile Thr Asp Ser Tyr Cys Ala Ala Gln Lys Lys Ala
        355                 360                 365

Phe Gly Asp Thr Asp Val Phe Thr Lys His Gly Gly Met Ala Gly Met
    370                 375                 380

Gly Ala Gly Leu Asp Glu Gly Met Val Leu Val Met Ser Leu Trp Asp
385                 390                 395                 400

Asp His Ala Ala Asn Met Leu Trp Leu Asp Ser Ile Tyr Pro Thr Thr
                405                 410                 415

Ala Thr Ser Thr Thr Pro Gly Ala Ala Arg Gly Ser Cys Asp Ile Ser
            420                 425                 430

Ser Gly Thr Pro Thr Asp Val Glu Ala Asn His Ala Asn Ala Tyr Val
        435                 440                 445

Ile Tyr Ser Asn Ile Lys Val Gly Pro Leu Gly Ser Thr Phe Asn Ser
    450                 455                 460

Gly Ser Ser Gly Ser Gly Thr Thr Thr Thr Thr Thr Thr Lys Ala Thr
465                 470                 475                 480

Thr Thr Thr Thr Thr Lys Ala Thr Thr Thr Thr Thr Gly Ser Thr Thr
                485                 490                 495

Thr Gly Ala Ala His Tyr Ala Gln Cys Gly Gly Ser Ser Trp Thr Gly
            500                 505                 510
```

```
Ala Thr Thr Cys Ala Ser Pro Tyr Thr Cys Gln Lys Gln Asn Asp Phe
        515                 520                 525

Tyr Ser Gln Cys Leu
    530


<210> SEQ ID NO 4
<211> LENGTH: 456
<212> TYPE: PRT
<213> ORGANISM: Talaromyces verruculosus

<400> SEQUENCE: 4

Met Leu Arg Tyr Leu Ser Ile Val Ala Ala Thr Ala Ile Leu Thr Gly
1               5                   10                  15

Val Glu Ala Gln Gln Ser Val Trp Gly Gln Cys Gly Gly Gln Gly Trp
            20                  25                  30

Thr Gly Ala Thr Ser Cys Ala Ala Gly Ser Thr Cys Ser Thr Leu Asn
        35                  40                  45

Pro Tyr Tyr Ala Gln Cys Ile Pro Ala Thr Ala Thr Ser Thr Thr Leu
    50                  55                  60

Ala Thr Thr Thr Ser Ser Thr Ser Val Gly Thr Thr Ser Pro Pro Thr
65                  70                  75                  80

Thr Thr Thr Thr Lys Ala Thr Thr Thr Ala Thr Thr Ala Ala Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Ile Pro Ser Leu Thr Gly Thr Leu Ala
        115                 120                 125

Ala Ala Ala Thr Lys Ala Ala Glu Ile Pro Ser Phe Val Trp Leu Asp
    130                 135                 140

Thr Ala Ala Lys Val Pro Thr Met Gly Thr Tyr Leu Ala Asn Ile Gln
145                 150                 155                 160

Ala Ala Asn Lys Ala Gly Ala Ser Pro Pro Ile Ala Gly Ile Phe Val
                165                 170                 175

Val Tyr Asp Leu Pro Asp Arg Asp Cys Ala Ala Ala Ala Ser Asn Gly
            180                 185                 190

Glu Tyr Thr Val Ala Asn Asn Gly Val Ala Asn Tyr Lys Ala Tyr Ile
        195                 200                 205

Asp Ser Ile Val Ala Gln Leu Lys Ala Tyr Pro Asp Val His Thr Ile
    210                 215                 220

Leu Ile Ile Glu Pro Asp Ser Leu Ala Asn Met Val Thr Asn Leu Ser
225                 230                 235                 240

Thr Ala Lys Cys Ala Glu Ala Gln Ser Ala Tyr Tyr Glu Cys Val Asn
                245                 250                 255

Tyr Ala Leu Ile Asn Leu Asn Leu Ala Asn Val Ala Met Tyr Ile Asp
            260                 265                 270

Ala Gly His Ala Gly Trp Leu Gly Trp Pro Ala Asn Leu Thr Pro Ala
        275                 280                 285

Ala Gln Leu Phe Ala Ala Val Tyr Lys Asn Ala Ser Ala Pro Ala Ala
    290                 295                 300

Leu Arg Gly Leu Ala Thr Asn Val Ala Asn Tyr Asn Ala Trp Ser Ile
305                 310                 315                 320

Ser Ser Pro Pro Ser Tyr Thr Ser Gly Asp Ser Asn Tyr Asp Glu Gln
                325                 330                 335

Leu Tyr Ile Asn Ala Leu Ser Pro Leu Leu Thr Ala Asn Gly Trp Pro
```

```
            340                 345                 350

Asn Ala His Phe Ile Met Asp Thr Ser Arg Asn Gly Val Gln Pro Thr
        355                 360                 365

Lys Gln Gln Ala Trp Gly Asp Trp Cys Asn Val Ile Gly Thr Gly Phe
    370                 375                 380

Gly Val Pro Phe Thr Thr Ser Thr Gly Asp Ala Leu Glu Asp Ala Phe
385                 390                 395                 400

Val Trp Val Lys Pro Gly Gly Glu Ser Asp Gly Thr Ser Asn Ser Ser
                405                 410                 415

Ser Thr Arg Tyr Asp Tyr His Cys Gly Tyr Ser Asp Ala Leu Gln Pro
            420                 425                 430

Ala Pro Glu Ala Gly Thr Trp Phe Gln Ala Tyr Phe Ala Gln Leu Leu
        435                 440                 445

Thr Asn Ala Asn Pro Ala Leu Ala
    450                 455


<210> SEQ ID NO 5
<211> LENGTH: 410
<212> TYPE: PRT
<213> ORGANISM: Cladosporium antareticum

<400> SEQUENCE: 5

Met Lys Ser Ser Phe Ile Ala Val Ala Ala Ala Ser Thr Val Gly Ser
1               5                   10                  15

Ala Tyr Ala Gln Gly Gln Ala Tyr Ala Gln Cys Gly Gly Val Gly Trp
            20                  25                  30

Ser Gly Ser Thr Ser Cys Val Ser Gly Tyr Thr Cys Thr Lys Thr Asn
        35                  40                  45

Asp Tyr Tyr Ser Gln Cys Leu Pro Gly Gly Gly Ser Asn Pro Thr Thr
    50                  55                  60

Thr Thr Arg Pro Ser Thr Thr Thr Thr Ser Arg Thr Gly Gly Ser Pro
65                  70                  75                  80

Thr Gly Gly Ser Gly Ser Gly Arg Val Ser Asn Ala Gly Val Asn Ile
                85                  90                  95

Ala Gly Leu Asp Phe Gly Cys Thr Ile Asp Gly Thr Cys Lys Thr Ala
            100                 105                 110

Asn Ile Val Asp Pro Gly Gln Ile Gly Ile Asp Gln Met Gln His Phe
        115                 120                 125

Val Lys Asp Asp Gly Leu Asn Thr Phe Arg Ile Pro Val Gly Trp Gln
    130                 135                 140

Phe Leu Leu Asn Asn Asn Leu Gly Gly Thr Leu Asp Ser Asn Asn Trp
145                 150                 155                 160

Asn Thr Tyr Asp Lys Gln Ile Gln Gly Cys Leu Asn Thr Gly Ala Ala
                165                 170                 175

Leu Cys Ile Val Asp Ile His Asn Tyr Ala Arg Trp Asn Gly Ala Ile
            180                 185                 190

Val Gly Gln Gly Gly Pro Thr Asn Ala Gln Phe Thr Ser Leu Trp Ser
        195                 200                 205

Gln Ile Ala Ala Lys Tyr Lys Gly Asn Asn Lys Ile Ala Phe Gly Leu
    210                 215                 220

Met Asn Glu Pro His Asp Leu Asn Ile Asn Thr Trp Ala Gln Thr Val
225                 230                 235                 240

Gln Glu Ala Val Thr Ala Ile Arg Lys Ala Gly Ala Thr Ser Asn Lys
                245                 250                 255
```

```
Ile Leu Leu Pro Gly Thr Asp Phe Thr Ser Ala Gly Ala Phe Ile Ser
            260                 265                 270

Asn Gly Ser Gly Gly Ala Leu Ile Lys Val Thr Asn Leu Asp Gly Ser
        275                 280                 285

Thr Thr Asn Leu Ile Phe Asp Val His Lys Tyr Leu Asp Ser Asp Asn
    290                 295                 300

Ser Gly Thr His Thr Thr Cys Thr Thr Asn Asn Ala Glu Ala Phe Thr
305                 310                 315                 320

Ser Leu Gly Asn Trp Leu Arg Thr Asn Lys Arg Gln Ala Ile Leu Thr
                325                 330                 335

Glu Thr Gly Gly Gly Pro Asn Asp Ala Ser Cys Leu Lys Ala Val Cys
            340                 345                 350

Glu Gln Leu Asp Val Leu Asn Ser Tyr Ser Asp Val Tyr Leu Gly Trp
        355                 360                 365

Thr Gly Trp Ser Ala Gly Arg Phe Asp Ala Thr Tyr Glu Leu Thr Glu
    370                 375                 380

Thr Pro Thr Arg Asn Gly Asn Gly Gly Trp Thr Asp Val Pro Leu Val
385                 390                 395                 400

Thr Gln Cys Ile Ala Gly Lys Phe Lys Arg
                405                 410


<210> SEQ ID NO 6
<211> LENGTH: 855
<212> TYPE: PRT
<213> ORGANISM: Talaromyces pinophilus

<400> SEQUENCE: 6

Met Arg Asn Ser Leu Leu Ile Ser Leu Ala Ala Ala Ala Leu Ala Glu
1               5                   10                  15

Gly Lys Ala Tyr Ser Pro Pro Ala Tyr Pro Ala Pro Trp Ala Ser Gly
            20                  25                  30

Ala Gly Glu Trp Ala Gln Ala His Gln Arg Ala Val Glu Phe Val Ser
        35                  40                  45

Gln Leu Thr Leu Ala Glu Lys Ile Asn Leu Thr Thr Gly Val Gly Trp
    50                  55                  60

Glu Gly Gly Gln Cys Val Gly Asn Thr Gly Ser Ile Pro Arg Leu Gly
65                  70                  75                  80

Phe Arg Ser Leu Cys Met Gln Asp Ser Pro Leu Gly Val Arg Asp Thr
                85                  90                  95

Asp Tyr Asn Thr Ala Phe Pro Ala Gly Val Asn Val Ala Ala Thr Trp
            100                 105                 110

Asp Leu Asp Leu Ala Tyr Arg Arg Gly Ile Ala Met Ala Glu Glu His
        115                 120                 125

Arg Gly Lys Gly Val Asp Val Gln Leu Gly Pro Val Ala Gly Pro Leu
    130                 135                 140

Gly Arg Val Pro Glu Gly Gly Arg Asn Trp Glu Gly Phe Ala Pro Asp
145                 150                 155                 160

Pro Val Leu Thr Gly Gln Met Met Ala Ser Thr Ile Gln Gly Met Gln
                165                 170                 175

Asp Thr Gly Val Ile Ala Cys Ala Lys His Tyr Ile Gly Asn Glu Gln
            180                 185                 190

Glu His Phe Arg Gln Gly Ser Gln Glu Asn Phe Thr Val Ala Asp Ala
        195                 200                 205

Ile Ser Ser Asn Ile Asp Asp Ile Thr Leu His Glu Leu Tyr Leu Trp
    210                 215                 220
```

```
Pro Phe Ala Asp Ala Val Arg Ala Gly Val Gly Ser Val Met Cys Ser
225                 230                 235                 240

Tyr Asn Gln Ile Asn Asn Ser Tyr Ser Cys Gly Asn Ser Tyr Thr Leu
                245                 250                 255

Asn His Ile Leu Lys Gly Glu Leu Asp Phe Gln Gly Phe Val Met Thr
            260                 265                 270

Asp Trp Ser Ala Gln His Ser Gly Val Gly Asp Ala Leu Ala Gly Ala
        275                 280                 285

Asp Met Asp Met Pro Gly Asp Val Ala Phe Asp Ser Gly Thr Ala Phe
    290                 295                 300

Trp Gly Thr Asn Leu Thr Ile Ala Val Leu Asn Gly Thr Val Pro Glu
305                 310                 315                 320

Trp Arg Val Asp Asp Met Ala Val Arg Ile Met Ser Ala Phe Tyr Lys
                325                 330                 335

Val Gly Arg Asp Arg Thr Gln Val Pro Ile Asn Phe Ala Ser Trp Thr
            340                 345                 350

Leu Asp Thr Tyr Gly Asn Glu Tyr Tyr Tyr Ala Gly Glu Gly Tyr Lys
        355                 360                 365

Glu Ile Asn Gln His Val Asp Val Arg Gly Gly His Ala Lys Val Val
    370                 375                 380

Arg Glu Ile Gly Ser Ala Ser Ile Val Leu Leu Lys Asn Val Asp Gly
385                 390                 395                 400

Ala Leu Pro Leu Thr Gly Ser Glu Lys Phe Val Ala Val Phe Gly Glu
                405                 410                 415

Asp Ala Gly Ser Asn Pro Asp Gly Val Asn Gly Cys Ser Asp Arg Gly
            420                 425                 430

Cys Asp Asn Gly Thr Leu Ala Met Gly Trp Gly Ser Gly Thr Ala Asn
        435                 440                 445

Phe Pro Tyr Leu Val Thr Pro Glu Gln Ala Ile Gln Ala Glu Val Val
    450                 455                 460

Lys Asn Gly Gly Met Phe Thr Ala Ile Thr Asp Ser Gly Ala Thr Asp
465                 470                 475                 480

Thr Ala Lys Thr Val Ala Ala Gln Ala Ser Ala Cys Leu Val Phe Ala
                485                 490                 495

Asn Ala Asp Ser Gly Glu Gly Tyr Ile Thr Val Asp Gly Asn Val Gly
            500                 505                 510

Asp Arg Lys Asn Leu Thr Leu Trp Gln Asn Gly Glu Ala Met Ile Ser
        515                 520                 525

Ala Val Ala Gly Asn Cys Asn Asn Thr Ile Val Val Leu His Thr Val
    530                 535                 540

Gly Pro Val Leu Val Glu Asp Trp Val His His Pro Asn Ile Thr Ala
545                 550                 555                 560

Val Leu Trp Ala Gly Leu Pro Gly Glu Gln Ser Gly Asn Ser Leu Val
                565                 570                 575

Asp Val Leu Tyr Gly Ser Val Asn Pro Gly Gly Lys Thr Pro Phe Thr
            580                 585                 590

Trp Gly Lys Gln Arg Ser Asp Trp Gly Val Asp Val Ile Tyr Glu Pro
        595                 600                 605

Asn Asn Gly Asp Gly Ala Pro Gln Gln Asp Phe Thr Glu Gly Ile Phe
    610                 615                 620

Ile Asp Tyr Arg His Phe Asp Lys Tyr Asn Ile Thr Pro Thr Tyr Glu
625                 630                 635                 640
```

Phe Gly Tyr Gly Leu Ser Tyr Ser Thr Phe Ser Phe Ser Asp Leu Lys
645 650 655

Val Thr Pro Ile Ala Ala Ser Pro Tyr Arg Pro Ala Lys Gly Gln Ser
660 665 670

Gly Pro Ala Pro Val Leu Gly Lys Val Leu Asn Ala Thr Ala Tyr Leu
675 680 685

Phe Pro Asp Tyr Ile Lys Arg Ile Glu Ala Phe Ile Tyr Pro Trp Leu
690 695 700

Asn Ser Thr Asp Leu Lys Thr Ser Ser Gly Asp Pro Asn Tyr Gly Trp
705 710 715 720

Pro Thr Ser Lys Tyr Val Pro Asp Gly Ala Gln Asp Gly Ser Pro Gln
725 730 735

Pro Val Asn Pro Ala Gly Gly Ala Pro Gly Gly Asn Pro Ala Leu Tyr
740 745 750

Asp Pro Val Ala Glu Val Thr Val Thr Val Lys Asn Thr Gly Lys Val
755 760 765

Ala Gly Val Glu Val Pro Gln Leu Tyr Val Ser Leu Gly Gly Pro Ser
770 775 780

Asp Ala Pro Lys Val Leu Arg Gly Phe Gly Arg Ile Ser Leu Gly Ala
785 790 795 800

Gly Glu Glu Thr Gln Trp Thr Ala Thr Leu Thr Arg Arg Asp Val Ser
805 810 815

Asn Trp Asp Thr Val Arg Gln Asn Trp Val Val Thr Asn Tyr Thr Lys
820 825 830

Thr Val Tyr Val Gly Asn Ser Ser Arg Asn Leu Pro Leu Gln Gln Thr
835 840 845

Leu Ala Leu Asn Ile Gly His
850 855

<210> SEQ ID NO 7
<211> LENGTH: 253
<212> TYPE: PRT
<213> ORGANISM: Penicillium emersonii

<400> SEQUENCE: 7

Met Leu Ser Ser Thr Thr Arg Thr Leu Ala Phe Thr Gly Leu Ala Gly
1 5 10 15

Leu Leu Ser Ala Pro Leu Val Lys Ala His Gly Phe Val Gln Gly Ile
20 25 30

Val Ile Gly Asp Gln Phe Tyr Ser Gly Tyr Ile Val Asn Ser Phe Pro
35 40 45

Tyr Glu Ser Asn Pro Pro Pro Val Ile Gly Trp Ala Thr Thr Ala Thr
50 55 60

Asp Leu Gly Phe Val Asp Gly Thr Gly Tyr Gln Gly Pro Asp Ile Ile
65 70 75 80

Cys His Arg Asn Ala Thr Pro Ala Pro Leu Thr Ala Pro Val Ala Ala
85 90 95

Gly Gly Thr Val Glu Leu Gln Trp Thr Pro Trp Pro Asp Ser His His
100 105 110

Gly Pro Val Ile Thr Tyr Leu Ala Pro Cys Asn Gly Asn Cys Ser Thr
115 120 125

Val Asp Lys Thr Thr Leu Glu Phe Phe Lys Ile Asp Gln Gln Gly Leu
130 135 140

Ile Asp Asp Thr Ser Pro Pro Gly Thr Trp Ala Ser Asp Asn Leu Ile
145 150 155 160

```
Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250


<210> SEQ ID NO 8
<211> LENGTH: 863
<212> TYPE: PRT
<213> ORGANISM: Aspergillus fumigatus

<400> SEQUENCE: 8

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
```

-continued

```
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700
```

```
Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860
```

<210> SEQ ID NO 9
<211> LENGTH: 532
<212> TYPE: PRT
<213> ORGANISM: Aspergillus fumigatus

<400> SEQUENCE: 9

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
```

```
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530


<210> SEQ ID NO 10
<211> LENGTH: 454
<212> TYPE: PRT
<213> ORGANISM: Aspergillus fumigatus

<400> SEQUENCE: 10

Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45
```

```
Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450
```

<210> SEQ ID NO 11
<211> LENGTH: 583
<212> TYPE: PRT
<213> ORGANISM: Rhizomucor pusillus

<400> SEQUENCE: 11

```
Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380
```

Gly Ser Gly Ser Thr Asn Gln Val Ser Phe Ser Val Ser Gly Lys Phe
385 390 395 400

Asp Ser Gly Ala Ser Leu Met Asp Ile Val Ser Asn Ile Thr Thr Thr
405 410 415

Val Ser Ser Asp Gly Thr Val Thr Phe Asn Leu Lys Asp Gly Leu Pro
420 425 430

Ala Ile Phe Thr Ser Ala Thr Gly Gly Thr Thr Thr Thr Ala Thr Pro
435 440 445

Thr Gly Ser Gly Ser Val Thr Ser Thr Ser Lys Thr Thr Ala Thr Ala
450 455 460

Ser Lys Thr Ser Thr Ser Thr Ser Ser Thr Ser Cys Thr Thr Pro Thr
465 470 475 480

Ala Val Ala Val Thr Phe Asp Leu Thr Ala Thr Thr Thr Tyr Gly Glu
485 490 495

Asn Ile Tyr Leu Val Gly Ser Ile Ser Gln Leu Gly Asp Trp Glu Thr
500 505 510

Ser Asp Gly Ile Ala Leu Ser Ala Asp Lys Tyr Thr Ser Ser Asp Pro
515 520 525

Leu Trp Tyr Val Thr Val Thr Leu Pro Ala Gly Glu Ser Phe Glu Tyr
530 535 540

Lys Phe Ile Arg Ile Glu Ser Asp Asp Ser Val Glu Trp Glu Ser Asp
545 550 555 560

Pro Asn Arg Glu Tyr Thr Val Pro Gln Ala Cys Gly Thr Ser Thr Ala
565 570 575

Thr Val Thr Asp Thr Trp Arg
580

<210> SEQ ID NO 12
<211> LENGTH: 1020
<212> TYPE: PRT
<213> ORGANISM: Talaromyces funiculosus

<400> SEQUENCE: 12

Leu Pro Phe Asn Glu Arg Val Asp Gln Val Leu Arg Ser Tyr Glu Val
1 5 10 15

Thr Ser Lys Leu Asp Ser Arg Ser Thr Lys Pro Ser Lys His Gly His
20 25 30

Thr Tyr Gln Thr Gln Phe Leu Gly Val Thr Trp Asp Gln Arg Asn Trp
35 40 45

Arg Leu Gln Ser Thr Val Leu Asp Gln Gly His Tyr Glu Ser Arg Gly
50 55 60

Ser Ile Ala Asn Gly Tyr Ile Gly Leu Asn Val Ala Gly Ala Gly Pro
65 70 75 80

Leu Phe Glu Leu Asp Ser Pro Val Asp Gly Asp Val Ile Asn Gly Trp
85 90 95

Pro Leu Phe Ser Arg Arg Gln Thr Phe Ala Gly Leu Ala Gly Phe Tyr
100 105 110

Asp Leu Gln Pro Arg Thr Asn Gly Thr Asn Phe Pro Trp Leu Ser Gln
115 120 125

Tyr Gly Asp Asp Ser Ala Ile Ser Gly Val Pro His Trp Gly Gly Met
130 135 140

Val Leu Asp Leu Gly Asp Gly Glu Tyr Leu Asp Ala Thr Val Asp Asn
145 150 155 160

Ser Thr Ile Ser Asp Tyr Thr Thr Thr Tyr Asp Tyr Lys Ala Gly Val
165 170 175

```
Leu Ser Trp Asp Tyr Lys Trp Thr Pro Lys Asn Ala Asn Gly Ser Phe
            180                 185                 190

Gly Ile Ser Tyr Lys Ile Phe Ala Asn Lys Leu Asp Val Asn Gln Ala
        195                 200                 205

Val Val Gln Leu Ser Ile Thr Pro Ser Thr Asn Gly Ser Ala Ser Val
    210                 215                 220

Val Asn Val Ile Asp Gly Tyr Ala Ala Val Arg Thr Asp Phe Val Ser
225                 230                 235                 240

Ser Gly Asn Glu Ser Asp Val Val Tyr Thr Ala Val Lys Pro Asn Gly
                245                 250                 255

Val Thr Asn Val Thr Ala Trp Ile Tyr Thr Ala Leu Asp Gly Asp Asp
            260                 265                 270

Ala Phe Asp Ile Ser Ser Ala Ala Leu Val Asn Asp Lys Pro Tyr Val
        275                 280                 285

His Gln Asn Asp Ser Ser Ile Ala Gln Ser Val Asn Val Thr Phe Thr
    290                 295                 300

Ala Gly Thr Thr Ile Thr Ile Asn Lys Phe Val Gly Ala Ala Ser Thr
305                 310                 315                 320

Asp Ala Phe Pro Asp Pro Gln Ser Thr Ala Arg Glu Ala Ala Leu Ser
                325                 330                 335

Ala Arg Arg Arg Gly Phe Asp Asp Leu Phe Arg Ser His Ile Ser Glu
            340                 345                 350

Trp Ala Gln Val Met Pro Asp Asp Ser Val Asp Asp Phe Thr Leu Ala
        355                 360                 365

Asn Gly Thr Leu Pro Asn Asp Thr Phe Ile Ile Glu Ser Ala Val Met
    370                 375                 380

Ala Val Val Asn Pro Tyr Tyr Leu Leu Gln Asn Thr Val Gly Pro Asn
385                 390                 395                 400

Ala Leu Arg Arg Val Asn Asn Ala Pro Val Asn Asp Trp Ser Ile Pro
                405                 410                 415

Val Gly Gly Leu Thr Ser Asp Ser Tyr Ala Gly Gln Ile Phe Trp Asp
            420                 425                 430

Ala Asp Val Trp Met Gln Pro Gly Leu Val Ala Ala Phe Pro Glu Ser
        435                 440                 445

Ala Lys Arg Ile Thr Asn Tyr Arg Ala Ala Lys Tyr Ser Gln Ala Leu
    450                 455                 460

Glu Asn Ala Lys Thr Ala Tyr Thr Ser Ser Gln Asn Gln Thr Trp Phe
465                 470                 475                 480

Ser Pro Asp Ala Ala Ile Tyr Ser Trp Thr Ser Gly Arg Val Gly Asn
                485                 490                 495

Cys Thr Ala Thr Gly Pro Cys Trp Asp Tyr Glu Tyr His Leu Asn Gly
            500                 505                 510

Asp Ile Gly Ile Ser Leu Val Asn Glu Trp Val Val Ser Gly Asp Asn
        515                 520                 525

Glu Thr Phe Lys Asn Lys His Phe Pro Ile Tyr Asn Ser Ile Ala Thr
    530                 535                 540

Leu Tyr Gly Asp Leu Leu Lys Lys Asn Gly Ser Tyr Tyr Thr Leu Thr
545                 550                 555                 560

Asn Met Thr Asp Pro Asp Glu Tyr Ala Asn Asn Val Asp Ala Gly Gly
                565                 570                 575

Tyr Thr Met Thr Leu Ile Ser Gln Thr Leu Ser Asn Ala Asn Ala Phe
            580                 585                 590
```

```
Arg Lys Gln Phe Gly Met Asn Glu Asn Thr Thr Trp Thr Glu Met Ala
        595                 600                 605

Asp Asn Ile Leu Leu Ile Arg Glu Asn Asp Val Thr Leu Glu Tyr Thr
    610                 615                 620

Thr Met Asn Asn Ser Val Ala Val Lys Gln Ala Asp Val Ile Leu Ser
625                 630                 635                 640

Thr Phe Pro Leu Asp Tyr Thr Lys Asn Tyr Thr Thr Ser Ala Ala Leu
                645                 650                 655

Asn Asp Leu Asp Tyr Tyr Ala Leu Lys Gln Ser Pro Asp Gly Pro Gly
            660                 665                 670

Met Thr Tyr Ala Ile Phe Ser Ile Val Ala Asn Asp Val Ser Pro Ser
        675                 680                 685

Gly Cys Ser Ala Tyr Thr Tyr Ala Gln Tyr Ser Tyr Asp Pro Tyr Ile
    690                 695                 700

Arg Gly Pro Phe Phe Gln Phe Ser Glu Gln Leu Leu Asp Asp Tyr Thr
705                 710                 715                 720

Ile Asn Gly Gly Thr His Pro Ala Phe Pro Phe Leu Thr Gly His Gly
                725                 730                 735

Gly Ala Asn Gln Val Val Leu Tyr Gly Tyr Leu Gly Leu Arg Leu Leu
            740                 745                 750

Pro Asp Asp Met Leu His Ile Asp Pro Asn Leu Pro Pro Gln Ile Pro
        755                 760                 765

Ser Ile Lys Tyr Arg Thr Phe Tyr Trp Arg Gly Trp Pro Ile Gln Ala
    770                 775                 780

Ala Ser Asn Tyr Thr His Thr Thr Ile Gln Arg Ala Thr Thr Val Ala
785                 790                 795                 800

Pro Leu Ser Thr Ala Asp Pro Thr Tyr Ala Asn Lys Ser Ile His Val
                805                 810                 815

Ser Val Gly His Asn Thr Val Asn Ser Thr Thr Tyr Ser Leu Ser Ala
            820                 825                 830

Asn Gly Ser Ala Leu Val Val Pro Asn Arg Gln Ile Gly Ser Ile Asn
        835                 840                 845

Thr Val Ala Gly Asn Val Val Gln Cys Lys Ser Val Leu Ser Thr Asp
    850                 855                 860

Ala Tyr Gln Lys Gly Gln Tyr Pro Ile Ser Ala Val Asp Gly Ala Ala
865                 870                 875                 880

Ser Thr Lys Trp Gln Pro Glu Phe Ala Ala Asn Ile Ser Ser Leu Thr
                885                 890                 895

Val Asp Leu Thr Gly Ser Asn Val Ser Ser Val Ser Gly Phe Tyr Phe
            900                 905                 910

Asp Trp Ala Gln Ala Pro Pro Thr Asn Ile Thr Val Leu Leu His Asn
        915                 920                 925

Ser Ser Ser Ala Ala Leu Ala Ser Ser Gly Asp Lys Pro Gly Ser Ser
    930                 935                 940

Ala Val Thr Leu Asn Ile Thr Ile Ser Asn Pro Tyr Asn Ala Ser Thr
945                 950                 955                 960

Tyr Asn Ala Asn Ile Ile Ala Leu Pro Ser Ser Asn Ser Thr Asn Tyr
                965                 970                 975

Thr Phe Pro Ala Pro Val Pro Lys Pro Arg Tyr Ala Thr Leu Phe Val
            980                 985                 990

Gln Gly Asn Gln Ala Leu Asp Glu  Thr Asp Thr Lys Ser  Gly Asn Gly
        995                 1000                 1005

Thr Gly  Ala Thr Val Ala Glu  Trp Ala Ile Leu Ser
```

1010 1015 1020

<210> SEQ ID NO 13
<211> LENGTH: 556
<212> TYPE: PRT
<213> ORGANISM: Gloeophyllum sepiarium

<400> SEQUENCE: 13

Gln Ser Val Asp Ser Tyr Val Ser Ser Glu Gly Pro Ile Ala Lys Ala
1 5 10 15

Gly Val Leu Ala Asn Ile Gly Pro Asn Gly Ser Lys Ala Ser Gly Ala
20 25 30

Ser Ala Gly Val Val Val Ala Ser Pro Ser Thr Ser Asp Pro Asp Tyr
35 40 45

Trp Tyr Thr Trp Thr Arg Asp Ser Ser Leu Val Phe Lys Ser Leu Ile
50 55 60

Asp Gln Tyr Thr Thr Gly Ile Asp Ser Thr Ser Ser Leu Arg Thr Leu
65 70 75 80

Ile Asp Asp Phe Val Thr Ala Glu Ala Asn Leu Gln Gln Val Ser Asn
85 90 95

Pro Ser Gly Thr Leu Thr Thr Gly Gly Leu Gly Glu Pro Lys Phe Asn
100 105 110

Val Asp Glu Thr Ala Phe Thr Gly Ala Trp Gly Arg Pro Gln Arg Asp
115 120 125

Gly Pro Ala Leu Arg Ser Thr Ala Leu Ile Thr Tyr Gly Asn Trp Leu
130 135 140

Leu Ser Asn Gly Asn Thr Ser Tyr Val Thr Ser Asn Leu Trp Pro Ile
145 150 155 160

Ile Gln Asn Asp Leu Gly Tyr Val Val Ser Tyr Trp Asn Gln Ser Thr
165 170 175

Tyr Asp Leu Trp Glu Glu Val Asp Ser Ser Ser Phe Phe Thr Thr Ala
180 185 190

Val Gln His Arg Ala Leu Arg Glu Gly Ala Ala Phe Ala Thr Ala Ile
195 200 205

Gly Gln Thr Ser Gln Val Ser Ser Tyr Thr Thr Gln Ala Asp Asn Leu
210 215 220

Leu Cys Phe Leu Gln Ser Tyr Trp Asn Pro Ser Gly Gly Tyr Ile Thr
225 230 235 240

Ala Asn Thr Gly Gly Gly Arg Ser Gly Lys Asp Ala Asn Thr Leu Leu
245 250 255

Ala Ser Ile His Thr Tyr Asp Pro Ser Ala Gly Cys Asp Ala Ala Thr
260 265 270

Phe Gln Pro Cys Ser Asp Lys Ala Leu Ser Asn Leu Lys Val Tyr Val
275 280 285

Asp Ser Phe Arg Ser Val Tyr Ser Ile Asn Ser Gly Val Ala Ser Asn
290 295 300

Ala Ala Val Ala Thr Gly Arg Tyr Pro Glu Asp Ser Tyr Gln Gly Gly
305 310 315 320

Asn Pro Trp Tyr Leu Thr Thr Phe Ala Val Ala Glu Gln Leu Tyr Asp
325 330 335

Ala Leu Asn Val Trp Glu Ser Gln Gly Ser Leu Glu Val Thr Ser Thr
340 345 350

Ser Leu Ala Phe Phe Gln Gln Phe Ser Ser Gly Val Thr Ala Gly Thr
355 360 365

```
Tyr Ser Ser Ser Ser Ser Thr Tyr Ser Thr Leu Thr Ser Ala Ile Lys
    370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Ala Gly Leu
        435                 440                 445

Thr Val Pro Ser Ser Cys Ser Gly Asn Ser Gly Gly Pro Thr Val Ala
    450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
            500                 505                 510

Leu Pro Ala Ser Thr Ala Ile Glu Tyr Lys Tyr Ile Arg Lys Asn Asn
        515                 520                 525

Gly Ala Val Thr Trp Glu Ser Asp Pro Asn Asn Ser Ile Thr Thr Pro
    530                 535                 540

Ala Ser Gly Ser Thr Thr Glu Asn Asp Thr Trp Arg
545                 550                 555


<210> SEQ ID NO 14
<211> LENGTH: 515
<212> TYPE: PRT
<213> ORGANISM: Bacillus stearothermophilus

<400> SEQUENCE: 14

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190
```

```
Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515


<210> SEQ ID NO 15
<211> LENGTH: 177
<212> TYPE: PRT
<213> ORGANISM: Thermoascus aurantiacus

<400> SEQUENCE: 15

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Ala Asp Ala Ala
            20                  25                  30

Gln Ser Gly Ser Ala Ser Lys Phe Ser Glu Tyr Phe Lys Thr Thr Ser
```

```
        35                  40                  45

Ser Ser Thr Arg Gln Thr Val Ala Ala Arg Leu Arg Ala Val Ala Arg
    50                  55                  60

Glu Ala Ser Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
        115                 120                 125

Glu Phe Thr His Ala Pro Gly Val Tyr Ser Pro Gly Thr Asp Asp Leu
    130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys


<210> SEQ ID NO 16
<211> LENGTH: 412
<212> TYPE: PRT
<213> ORGANISM: Pyrococcus furiosus

<400> SEQUENCE: 16

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
```

```
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Asp Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410


<210> SEQ ID NO 17
<211> LENGTH: 325
<212> TYPE: PRT
<213> ORGANISM: Palaeococcus ferrophilus

<400> SEQUENCE: 17

Gly Lys Pro Lys Pro Ser Gln Pro Pro Gln Glu Val Pro Trp Gly Ile
1               5                   10                  15

Glu Arg Val Lys Ala Pro Ser Val Trp Ser Thr Thr Asp Gly Ser Ser
            20                  25                  30

Asn Gly Val Ile Gln Val Ala Ile Leu Asp Thr Gly Ile Asp Tyr Asp
        35                  40                  45

His Pro Asp Leu Ala Ala Asn Leu Ala Trp Gly Val Ser Thr Leu Arg
    50                  55                  60

Gly Arg Val Ser Thr Lys Pro Lys Asp Tyr Arg Asp Gln Asn Gly His
65                  70                  75                  80

Gly Thr His Val Ala Gly Thr Ile Ala Ala Leu Asn Asn Asp Ile Gly
                85                  90                  95

Val Val Gly Val Ala Pro Gly Val Gln Ile Tyr Ala Ile Arg Val Leu
            100                 105                 110

Asp Ala Ser Gly Arg Gly Ser Tyr Ser Asp Ile Ala Ile Gly Ile Glu
        115                 120                 125

Gln Ala Ile Leu Gly Pro Asp Gly Val Ala Asp Lys Asp Gly Asp Gly
    130                 135                 140

Ile Ile Ala Gly Asp Pro Asp Asp Asp Ala Ala Glu Val Ile Ser Met
145                 150                 155                 160

Ser Leu Gly Gly Ser Ala Asp Asp Ser Tyr Leu His Asp Met Ile Ile
                165                 170                 175

Gln Ala Tyr Asn Ala Gly Ile Val Ile Val Ala Ala Ser Gly Asn Glu
            180                 185                 190
```

```
Gly Ala Ser Ser Pro Ser Tyr Pro Ala Ala Tyr Pro Glu Val Ile Ala
        195                 200                 205

Val Gly Ala Ser Asp Ile Asn Asp Asn Ile Ala Ser Phe Ser Asn Arg
    210                 215                 220

Gln Pro Glu Val Ser Ala Pro Gly Val Asp Val Leu Ser Thr Tyr Pro
225                 230                 235                 240

Asp Asp Thr Tyr Lys Thr Leu Ser Gly Thr Ser Met Ala Thr Pro His
                245                 250                 255

Val Ser Gly Val Val Ala Leu Ile Gln Ala Ala His Phe Asn Lys Tyr
            260                 265                 270

Gly Thr Ile Leu Pro Val Gly Thr Phe Asp Asp Met Ser Lys Asn Thr
        275                 280                 285

Val Arg Gly Ile Leu His Ile Thr Ala Asp Asp Leu Gly Ser Pro Gly
    290                 295                 300

Trp Asp Val Asp Tyr Gly Tyr Gly Ile Val Arg Ala Asp Leu Ala Val
305                 310                 315                 320

Gln Ala Ala Leu Gly
                325


<210> SEQ ID NO 18
<211> LENGTH: 186
<212> TYPE: PRT
<213> ORGANISM: Thermobifida cellulosytica

<400> SEQUENCE: 18

Ala Asp Val Ile Gly Gly Asn Pro Tyr Tyr Phe Gly Gly Tyr Arg Cys
1               5                   10                  15

Ser Ile Gly Phe Ser Val Arg Lys Gly Ser Asp Thr Gly Phe Ala Thr
            20                  25                  30

Ala Gly His Cys Gly Glu Thr Gly Thr Leu Thr Arg Ser Pro Glu Gly
        35                  40                  45

Val Val Ala Gly Ser Tyr Phe Pro Gly Arg Asp Met Gly Trp Val Arg
    50                  55                  60

Leu Thr Gly Ala Asp Thr Val Thr Pro Leu Val Asn Arg Tyr Asp Gly
65                  70                  75                  80

Gly Thr Val Thr Val Thr Gly Ser Gln Glu Ala Val Thr Gly Ser Ser
                85                  90                  95

Val Cys Arg Ser Gly Ser Thr Thr Gly Trp Arg Cys Gly Ile Ile Gln
            100                 105                 110

Ser Lys Asn Gln Thr Val Arg Tyr Ala Glu Gly Thr Val Thr Gly Leu
        115                 120                 125

Thr Arg Thr Thr Ala Cys Ala Glu Ala Gly Asp Ser Gly Gly Pro Trp
    130                 135                 140

Leu Thr Gly Ser Gln Ala Gln Gly Val Thr Ser Gly Gly Ser Gly Asn
145                 150                 155                 160

Cys Arg Thr Gly Gly Ile Thr Tyr Phe Gln Pro Ile Asn Pro Leu Leu
                165                 170                 175

Ser Tyr Phe Gly Leu Glu Leu Val Thr Gly
            180                 185


<210> SEQ ID NO 19
<211> LENGTH: 186
<212> TYPE: PRT
<213> ORGANISM: Thermobifida fusca

<400> SEQUENCE: 19
```

```
Ala Ala Ile Ile Gly Gly Asn Pro Tyr Tyr Phe Gly Asn Tyr Arg Cys
1               5                   10                  15

Ser Ile Gly Phe Ser Val Arg Gln Gly Ser Gln Thr Gly Phe Ala Thr
            20                  25                  30

Ala Gly His Cys Gly Ser Thr Gly Thr Arg Val Ser Ser Pro Ser Gly
        35                  40                  45

Thr Val Ala Gly Ser Tyr Phe Pro Gly Arg Asp Met Gly Trp Val Arg
    50                  55                  60

Ile Thr Ser Ala Asp Thr Val Thr Pro Leu Val Asn Arg Tyr Asn Gly
65                  70                  75                  80

Gly Thr Val Thr Val Thr Gly Ser Gln Glu Ala Ala Thr Gly Ser Ser
                85                  90                  95

Val Cys Arg Ser Gly Ala Thr Thr Gly Trp Arg Cys Gly Thr Ile Gln
            100                 105                 110

Ser Lys Asn Gln Thr Val Arg Tyr Ala Glu Gly Thr Val Thr Gly Leu
        115                 120                 125

Thr Arg Thr Thr Ala Cys Ala Glu Gly Gly Asp Ser Gly Gly Pro Trp
    130                 135                 140

Leu Thr Gly Ser Gln Ala Gln Gly Val Thr Ser Gly Gly Thr Gly Asp
145                 150                 155                 160

Cys Arg Ser Gly Gly Ile Thr Phe Phe Gln Pro Ile Asn Pro Leu Leu
                165                 170                 175

Ser Tyr Phe Gly Leu Gln Leu Val Thr Gly
            180                 185


<210> SEQ ID NO 20
<211> LENGTH: 186
<212> TYPE: PRT
<213> ORGANISM: Thermobifida halotolerans

<400> SEQUENCE: 20

Thr Asp Ile Ile Gly Gly Asn Pro Tyr Tyr Phe Asp Gly Tyr Arg Cys
1               5                   10                  15

Ser Ile Gly Phe Ser Val Arg Arg Gly Ser Glu Ser Gly Phe Ala Thr
            20                  25                  30

Ala Gly His Cys Gly Glu Glu Gly Thr Glu Thr Ser Asp Pro Glu Gly
        35                  40                  45

Thr Val Ala Gly Ala Tyr Phe Pro Gly Arg Asp Met Gly Trp Val Arg
    50                  55                  60

Ile Thr Asp Ala Asp Thr Val Thr Pro Leu Val Asn Arg Tyr Asn Gly
65                  70                  75                  80

Glu Asn Val Thr Val Ala Gly Ser Arg Glu Ala Ala Thr Gly Ser Ser
                85                  90                  95

Val Cys Arg Ser Gly Ser Thr Thr Gly Trp Arg Cys Gly Thr Ile Arg
            100                 105                 110

Ser Lys Asn Gln Thr Val Arg Tyr Ile Glu Gly Thr Val Thr Gly Leu
        115                 120                 125

Thr Arg Thr Thr Ala Cys Ala Glu Gly Gly Asp Ser Gly Gly Pro Trp
    130                 135                 140

Leu Thr Gly Ser Gln Gly Gln Gly Val Thr Ser Gly Gly Ser Gly Asn
145                 150                 155                 160

Cys Thr Leu Gly Gly Val Thr Tyr Phe Gln Pro Leu Asn Pro Leu Leu
                165                 170                 175

Ser His Phe Asp Leu Asp Leu Val Thr Gly
            180                 185
```

<210> SEQ ID NO 21
<211> LENGTH: 325
<212> TYPE: PRT
<213> ORGANISM: Thermococcus nautili

<400> SEQUENCE: 21

```
Leu Val Pro Glu Pro Thr Gln Pro Ala Gln Glu Ile Pro Trp Gly Ile
1               5                   10                  15

Glu Arg Val Lys Ala Pro Asp Thr Trp Ser Ile Thr Thr Gly Ala Ser
            20                  25                  30

Asn Gly Val Ile Glu Val Ala Ile Leu Asp Thr Gly Ile Asp Trp Asp
        35                  40                  45

His Pro Asp Leu Lys Asp Asn Ile Ala Trp Gly Val Ser Thr Ile Gly
    50                  55                  60

Gly Glu Val Ser Thr Asp Pro Ala Asp Trp Tyr Asp Gly Asn Gly His
65                  70                  75                  80

Gly Thr His Val Ala Gly Thr Ile Ala Ala Leu Asn Asn Asp Ile Gly
                85                  90                  95

Val Val Gly Val Ala Pro Asn Val Glu Ile Tyr Ala Ile Lys Val Leu
            100                 105                 110

Asp Asp Arg Gly Ser Gly Ala Tyr Thr Asp Ile Ala Ile Gly Ile Glu
        115                 120                 125

Gln Ala Leu Leu Gly Pro Asp Gly Ile Leu Asp Lys Asp Gly Asp Gly
    130                 135                 140

Ile Ile Val Gly Asp Pro Asp Asp Asp Ala Ala Glu Val Ile Ser Met
145                 150                 155                 160

Ser Leu Gly Gly Pro Ser Asp Asp Glu Tyr Leu His Asp Met Ile Ile
                165                 170                 175

Lys Ala Tyr Asn Tyr Gly Val Val Ile Val Ala Ala Ser Gly Asn Glu
            180                 185                 190

Ala Ala Asp Gln Pro Ser Tyr Pro Ala Ile Tyr Pro Glu Val Ile Ala
        195                 200                 205

Val Gly Ala Thr Asp Ser Ser Asp Ala Val Ala Tyr Phe Ser Asn Leu
    210                 215                 220

Gln Pro Glu Val Ser Ala Pro Gly Val Asp Val Leu Ser Thr Tyr Pro
225                 230                 235                 240

Asp Asp Thr Tyr Glu Ser Leu Ser Gly Thr Ser Met Ala Thr Pro His
                245                 250                 255

Val Ser Gly Val Val Ala Leu Ile Gln Ala Ala Tyr Tyr Asn Lys Tyr
            260                 265                 270

Gly Lys Val Leu Pro Val Gly Thr Phe Asp Asp Met Asn Thr Asn Thr
        275                 280                 285

Val Arg Gly Ile Leu His Val Thr Ala Asp Asp Leu Gly Asp Pro Gly
    290                 295                 300

Trp Asp Ile Tyr Tyr Gly Tyr Gly Ile Val Arg Ala Asp Leu Ala Val
305                 310                 315                 320

Gln Ala Ala Leu Gly
                325
```

<210> SEQ ID NO 22
<211> LENGTH: 595
<212> TYPE: PRT
<213> ORGANISM: Penicillium oxalicum

<400> SEQUENCE: 22

```
Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415
```

```
Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595
```

<210> SEQ ID NO 23
<211> LENGTH: 1729
<212> TYPE: DNA
<213> ORGANISM: Talaromyces verruculosus

<400> SEQUENCE: 23

```
atgctgcgat atctttccat tgttgccgct acggcaatct tgaccggagt ggaagctcag     60

caatcggtct ggggtcaatg taagaaatct ttcgagaagc ttccagtcca aattaaatta    120

cagctattga catatttcag gtggtggtca aggctggact ggcgcaacgt catgcgccgc    180

cggttctaca tgcagcactc taaacccttg taagatgcca gctgattcca ttgcacgttg    240

gctctgttta ctgacagcaa ttggttcgca gactacgcac aatgtattcc tgccacagct    300

acttcaacca cattggcgac aaccacctct tccacaagtg ttgggacgac atcgccgccg    360

acaaccacca cgacgaaagc taccaccaca gctaccactg ccgctgcatc tggaaacccc    420

ttctctggtt atcagcttta tgccaatccg tactactctt cagaagtaca tactcttgcc    480

ataccatctc tgactggcac actcgccgct gctgcgacca aggctgcaga gattccgtca    540

tttgtctggc tgtgagtgtc ctcaataata tacaattgag tgttataaat atatgtgtga    600

acattttcta aacctttata gtgacacagc agctaaagtg cctacaatgg gtacctactt    660

ggctaacatt caagctgcaa acaaggctgg agctagccca cctattgccg gtatcttcgt    720

tgtctatgac ttgcctgacc gtgactgtgc agctgcagca agtaatggcg aatacacagt    780

agcaaacaac ggtgtcgcaa actataaggc ttacatcgat agcatcgtgg cacagttgaa    840

agcttatccc gatgtgcaca ccatcctcat cattggtacg ttctccagta ctggaccttg    900

aaaaagtact tttcagagaa attcatgtct aacacatcac cgttctacag aacccgacag    960

tctagccaat atggttacca atttgtctac agccaaatgt gccgaagctc aatctgcata   1020

ctacgagtgc gtcaactacg cattgatcaa cctcaacttg gccaacgtgg ccatgtacat   1080
```

```
tgatgccggt catgctggtt ggcttggatg gcctgccaat ctcacaccag ctgctcaact   1140

ttttgcagca gtctataaga atgcaagtgc tcctgcagca cttcgtggac tggccaccaa   1200

cgttgccaac tacaacgctt ggtcgatcag cagcccaccc tcctacacgt ctggtgactc   1260

caactacgac gaacagctct acatcaatgc tttgtctcct ctcctaacag caaacggctg   1320

gcctaatgct cactttatta tggatacttg taagtgtgcc gcaaatgact catccaagct   1380

ttcaacttac taatccgaat gtttgtttta gcccgaaacg gtgttcagcc aaccaagcag   1440

caggcatggg gagactggtg caatgtgatc ggaaccggct tcggtgttcc tttcacaacc   1500

agcaccggtg acgcactaga ggatgccttt gtctgggtca aaccaggtgg tgaaagtgat   1560

ggtacctcaa acagttcctc tactcgttac gattatcatt gcggctacag tgatgcactt   1620

caacctgctc ccgaggctgg cacttggttc caagcttatt ttgcccagct tttgaccaat   1680

gccaatccag ctttggccta gatcagcttt gactgcacca atatcctttt              1729
```

```
<210> SEQ ID NO 24
<211> LENGTH: 556
<212> TYPE: PRT
<213> ORGANISM: Trametes cingulata

<400> SEQUENCE: 24

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
        35                  40                  45

Asn Tyr Leu Tyr Thr Trp Thr Arg Asp Ser Ser Leu Val Phe Lys Ala
    50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
        115                 120                 125

Gly Pro Ala Leu Arg Ala Thr Ala Ile Ile Thr Tyr Ala Asn Trp Leu
    130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
            180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
    210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255
```

```
Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr
            340                 345                 350

Ser Leu Pro Phe Phe Gln Gln Phe Ser Ser Gly Val Thr Val Gly Thr
        355                 360                 365

Tyr Ala Ser Ser Ser Ser Thr Phe Lys Thr Leu Thr Ser Ala Ile Lys
    370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Ala Leu Thr Ser Phe
            420                 425                 430

Ala Ala Arg Ser Gly Lys Thr Tyr Ala Ser Trp Gly Ala Ala Gly Leu
        435                 440                 445

Thr Val Pro Thr Thr Cys Ser Gly Ser Gly Gly Ala Gly Thr Val Ala
    450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495

Leu Ile Leu Ser Ala Ala Asn Tyr Pro Thr Trp Ser Ile Thr Val Asn
            500                 505                 510

Leu Pro Ala Ser Thr Thr Ile Glu Tyr Lys Tyr Ile Arg Lys Phe Asn
        515                 520                 525

Gly Ala Val Thr Trp Glu Ser Asp Pro Asn Asn Ser Ile Thr Thr Pro
    530                 535                 540

Ala Ser Gly Thr Phe Thr Gln Asn Asp Thr Trp Arg
545                 550                 555


<210> SEQ ID NO 25
<211> LENGTH: 555
<212> TYPE: PRT
<213> ORGANISM: Pycnoporus sanguineus

<400> SEQUENCE: 25

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
            20                  25                  30

Gly Ala Lys Ala Gly Ile Val Val Ala Ser Pro Ser Thr Glu Asn Pro
        35                  40                  45

Asp Tyr Leu Tyr Thr Trp Thr Arg Asp Ser Ser Leu Val Phe Lys Leu
    50                  55                  60

Leu Ile Asp Gln Phe Thr Ser Gly Asp Asp Thr Ser Leu Arg Gly Leu
65                  70                  75                  80
```

```
Ile Asp Asp Phe Thr Ser Ala Glu Ala Ile Leu Gln Gln Val Ser Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Gly Ala Trp Gly Arg Pro Gln Arg Asp
        115                 120                 125

Gly Pro Ala Leu Arg Ala Thr Ser Ile Ile Arg Tyr Ala Asn Trp Leu
    130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Ser Phe Phe Thr Thr Ala
            180                 185                 190

Val Gln His Arg Ala Leu Arg Glu Gly Ala Thr Phe Ala Ser Arg Ile
        195                 200                 205

Gly Gln Ser Ser Val Val Ser Gly Tyr Thr Thr Gln Ala Asp Asn Leu
    210                 215                 220

Leu Cys Phe Leu Gln Ser Tyr Trp Asn Pro Ser Gly Gly Tyr Val Thr
225                 230                 235                 240

Ala Asn Thr Gly Gly Gly Arg Ser Gly Lys Asp Ser Asn Thr Val Leu
                245                 250                 255

Thr Ser Ile His Thr Phe Asp Pro Ala Ala Gly Cys Asp Ala Ala Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Thr Ile Asn Asn Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
        355                 360                 365

Tyr Ser Ala Ser Ser Ser Thr Tyr Ala Thr Leu Thr Ser Ala Ile Arg
    370                 375                 380

Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
                405                 410                 415

Ser Ala Val Asp Leu Thr Trp Ser Tyr Ala Ala Ala Leu Thr Ala Phe
            420                 425                 430

Ala Ala Arg Glu Gly Lys Thr Tyr Gly Ser Trp Gly Ala Ala Gly Leu
        435                 440                 445

Thr Val Pro Ala Ser Cys Ser Gly Gly Gly Gly Ala Thr Val Ala Val
    450                 455                 460

Thr Phe Asn Val Gln Ala Thr Thr Val Phe Gly Glu Asn Ile Tyr Ile
465                 470                 475                 480

Thr Gly Ser Val Ala Ala Leu Gln Asn Trp Ser Pro Asp Asn Ala Leu
                485                 490                 495
```

```
Ile Leu Ser Ala Ala Asn Tyr Pro Thr Trp Ser Ile Thr Val Asn Leu
            500                 505                 510

Pro Ala Asn Thr Val Val Gln Tyr Lys Tyr Ile Arg Lys Phe Asn Gly
        515                 520                 525

Gln Val Thr Trp Glu Ser Asp Pro Asn Asn Gln Ile Thr Thr Pro Ser
    530                 535                 540

Gly Gly Ser Phe Thr Gln Asn Asp Val Trp Arg
545                 550                 555


<210> SEQ ID NO 26
<211> LENGTH: 559
<212> TYPE: PRT
<213> ORGANISM: Gloeophyllum trabeum

<400> SEQUENCE: 26

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Ser Phe Phe Thr Thr Ala
            180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
            260                 265                 270

Phe Gln Pro Cys Ser Asp Lys Ala Leu Ser Asn Leu Lys Val Tyr Val
        275                 280                 285

Asp Ser Phe Arg Ser Val Tyr Ser Ile Asn Ser Gly Ile Ala Ser Asn
    290                 295                 300

Ala Ala Val Ala Thr Gly Arg Tyr Pro Glu Asp Ser Tyr Gln Gly Gly
305                 310                 315                 320
```

```
Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
            340                 345                 350

Ser Leu Pro Phe Phe Gln Gln Phe Ser Ser Ser Val Thr Ala Gly Thr
        355                 360                 365

Tyr Ala Ser Ser Ser Thr Thr Tyr Thr Thr Leu Thr Ser Ala Ile Lys
    370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Val Gly Leu
        435                 440                 445

Thr Val Pro Thr Ser Cys Ser Ser Asn Ser Gly Gly Gly Gly Ser
    450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
            500                 505                 510

Thr Val Asn Leu Pro Ala Ser Thr Ala Ile Gln Tyr Lys Tyr Ile Arg
        515                 520                 525

Lys Asn Asn Gly Ala Val Thr Trp Glu Ser Asp Pro Asn Asn Ser Ile
    530                 535                 540

Thr Thr Pro Ala Ser Gly Ser Val Thr Glu Asn Asp Thr Trp Arg
545                 550                 555


<210> SEQ ID NO 27
<211> LENGTH: 591
<212> TYPE: PRT
<213> ORGANISM: Talaromyces emersonii

<400> SEQUENCE: 27

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Ile Ala Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
        115                 120                 125

Pro Ala Leu Arg Ala Thr Ala Leu Ile Ala Tyr Ala Asn Tyr Leu Ile
```

-continued

```
    130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
            180                 185                 190

Gln His Arg Ala Leu Val Glu Gly Asn Ala Leu Ala Thr Arg Leu Asn
        195                 200                 205

His Thr Cys Ser Asn Cys Val Ser Gln Ala Pro Gln Val Leu Cys Phe
    210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ala Ile Asn Ser Gly Ile Ala Glu Gly Ser Ala Val Ala
    290                 295                 300

Val Gly Arg Tyr Pro Glu Asp Val Tyr Gln Gly Gly Asn Pro Trp Tyr
305                 310                 315                 320

Leu Ala Thr Ala Ala Ala Ala Glu Gln Leu Tyr Asp Ala Ile Tyr Gln
                325                 330                 335

Trp Lys Lys Ile Gly Ser Ile Ser Ile Thr Asp Val Ser Leu Pro Phe
            340                 345                 350

Phe Gln Asp Ile Tyr Pro Ser Ala Ala Val Gly Thr Tyr Asn Ser Gly
        355                 360                 365

Ser Thr Thr Phe Asn Asp Ile Ile Ser Ala Val Gln Thr Tyr Gly Asp
    370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
                405                 410                 415

Leu Thr Trp Ser Tyr Ala Ser Leu Leu Thr Ala Ser Ala Arg Arg Gln
            420                 425                 430

Ser Val Val Pro Ala Ser Trp Gly Glu Ser Ser Ala Ser Ser Val Pro
        435                 440                 445

Ala Val Cys Ser Ala Thr Ser Ala Thr Gly Pro Tyr Ser Thr Ala Thr
    450                 455                 460

Asn Thr Val Trp Pro Ser Ser Gly Ser Gly Ser Ser Thr Thr Thr Ser
465                 470                 475                 480

Ser Ala Pro Cys Thr Thr Pro Thr Ser Val Ala Val Thr Phe Asp Glu
                485                 490                 495

Ile Val Ser Thr Ser Tyr Gly Glu Thr Ile Tyr Leu Ala Gly Ser Ile
            500                 505                 510

Pro Glu Leu Gly Asn Trp Ser Thr Ala Ser Ala Ile Pro Leu Arg Ala
        515                 520                 525

Asp Ala Tyr Thr Asn Ser Asn Pro Leu Trp Tyr Val Thr Val Asn Leu
    530                 535                 540

Pro Pro Gly Thr Ser Phe Glu Tyr Lys Phe Phe Lys Asn Gln Thr Asp
545                 550                 555                 560
```

Gly Thr Ile Val Trp Glu Asp Asp Pro Asn Arg Ser Tyr Thr Val Pro
565 570 575

Ala Tyr Cys Gly Gln Thr Thr Ala Ile Leu Asp Asp Ser Trp Gln
580 585 590

<210> SEQ ID NO 28
<211> LENGTH: 694
<212> TYPE: PRT
<213> ORGANISM: Myceliophthora sepedonium

<400> SEQUENCE: 28

Met Ala Leu Arg His Ile Ala Ala Ala Ala Ile Ala Gly Leu Ala Ser
1 5 10 15

Arg Thr Ala Ala Leu Tyr Ile Asn Gly Ser Val Thr Ala Pro Cys Asp
20 25 30

Ser Pro Ile Tyr Cys Gln Gly Glu Leu Leu Lys Ala Val Glu Leu Ala
35 40 45

Arg Pro Phe Val Asp Ser Lys Thr Phe Val Asp Met Pro Thr Ile Lys
50 55 60

Pro Val Asp Glu Val Leu Ala Ala Phe Ser Lys Leu Ser Leu Pro Leu
65 70 75 80

Ser Asn Asn Ser Glu Leu Asn Ala Phe Leu Tyr Glu Asn Phe Ala Gln
85 90 95

Ala Gly His Glu Leu Glu Glu Val Pro Asp Ser Glu Leu Glu Thr Asp
100 105 110

Ala Lys Phe Leu Asp Lys Leu Glu Asp Arg Thr Ile Lys Glu Phe Val
115 120 125

Gly Lys Val Ile Asp Ile Trp Pro Asp Leu Thr Arg Arg Tyr Ala Gly
130 135 140

Pro Ser Asn Cys Thr Glu Cys Ala Asn Ser Phe Ile Pro Val Asn Arg
145 150 155 160

Thr Phe Val Val Ala Gly Gly Arg Phe Arg Glu Pro Tyr Tyr Trp Asp
165 170 175

Ser Tyr Trp Ile Val Glu Gly Leu Leu Arg Thr Gly Gly Ala Phe Thr
180 185 190

His Ile Ser Lys Asn Ile Ile Glu Asn Phe Leu Asp Phe Val Asp Thr
195 200 205

Ile Gly Phe Ile Pro Asn Gly Ala Arg Ile Tyr Tyr Leu Asn Arg Ser
210 215 220

Gln Pro Pro Leu Leu Thr Leu Met Val Lys Ser Tyr Val Asp Tyr Thr
225 230 235 240

Asn Asp Thr Ser Ile Leu Asp Arg Ala Leu Pro Leu Leu Ile Lys Glu
245 250 255

His Glu Phe Phe Met Asn Asn Arg Thr Val Ser Ile Thr Gly Ser Asn
260 265 270

Gly Lys Glu Tyr Thr Leu Asn Arg Tyr His Val Glu Asn Asn Gln Pro
275 280 285

Arg Pro Glu Ser Phe Arg Glu Asp Tyr Ile Thr Ala Asn Asn Gly Ser
290 295 300

Tyr Tyr Ala Ser Ser Gly Ile Ile Tyr Pro Val Lys Thr Pro Leu Asn
305 310 315 320

Glu Thr Glu Lys Ala Ala Leu Tyr Ser Asn Leu Ala Thr Gly Ala Glu
325 330 335

Ser Gly Trp Asp Tyr Thr Ser Arg Trp Leu Gly Val Pro Ser Asp Ala

```
            340                 345                 350

Ala Arg Asp Val Tyr Phe Pro Leu Arg Ser Leu Asn Val Arg Asp Ile
        355                 360                 365

Val Pro Val Asp Leu Asn Ser Ile Leu Tyr Gln Asn Glu Val Ile Ile
    370                 375                 380

Ala Glu Tyr Leu Glu Lys Ala Gly Asn Ser Ser Ala Ala Lys Arg Phe
385                 390                 395                 400

Ala Thr Ala Ala Glu Gln Arg Ser Glu Ala Met Tyr Ser Leu Met Trp
                405                 410                 415

Asn Ala Thr His Trp Ser Tyr Phe Asp Tyr Asn Leu Thr Asp Asn Thr
            420                 425                 430

Gln His Ile Phe Val Pro Ala Asp Glu Asp Thr Ala Pro Gln Asp Arg
        435                 440                 445

Ile Glu Ala Pro Pro Gly Gln Gln Val Phe Phe His Ile Ala Gln Leu
    450                 455                 460

Tyr Pro Phe Trp Thr Gly Ala Ala Pro Ala Ser Leu Lys Ala Asn Pro
465                 470                 475                 480

Leu Ala Val Gln Gln Ala Tyr Ala Arg Val Ala Arg Met Leu Asp Ile
                485                 490                 495

Lys Lys Gly Ala Ile Pro Ala Thr Asn Tyr Arg Thr Gly Gln Gln Trp
            500                 505                 510

Asp Gln Pro Asn Val Trp Pro Pro Leu Gln His Ile Leu Met Lys Gly
        515                 520                 525

Leu Leu Asn Thr Pro Ala Thr Phe Gly Lys Ser Asp Pro Ala Tyr Gln
    530                 535                 540

Ser Val Gln Asn Leu Ala Leu Arg Leu Ala Gln Arg Tyr Leu Asp Ser
545                 550                 555                 560

Thr Phe Cys Thr Trp Tyr Ala Thr Gly Gly Ser Thr Ser Asp Phe Pro
                565                 570                 575

Gln Leu Glu Gly Val Thr Pro Gly Ala Thr Gly Val Met Phe Glu Lys
            580                 585                 590

Tyr Ala Asp Asn Ala Thr Asn Val Ala Gly Gly Gly Gly Glu Tyr Glu
        595                 600                 605

Val Val Glu Gly Phe Gly Trp Thr Asn Gly Val Leu Ile Trp Ala Ala
    610                 615                 620

Asp Val Phe Gly Asn Lys Leu Lys Arg Pro Asp Cys Gly Asn Ile Thr
625                 630                 635                 640

Ala Ala His Thr His Ser Ser Ala Lys Arg Gly Leu Glu Glu Asn Lys
                645                 650                 655

Leu Pro Arg Arg Ala Val Glu Leu Asp Pro Trp Asp Ala Ala Trp Thr
            660                 665                 670

Lys Met Phe Gly Arg Ser Lys Leu Arg Arg Arg Glu Ala Glu Asp Val
        675                 680                 685

Arg Lys Arg Trp Met Ser
    690


<210> SEQ ID NO 29
<211> LENGTH: 459
<212> TYPE: PRT
<213> ORGANISM: Trichoderma reesei

<400> SEQUENCE: 29

Met Ala Pro Ser Val Thr Leu Pro Leu Thr Thr Ala Ile Leu Ala Ile
1               5                   10                  15
```

-continued

```
Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
```

```
        435                 440                 445

Gln Tyr Ser Asn Asp Tyr Tyr Ser Gln Cys Leu
    450                 455
```

<210> SEQ ID NO 30
<211> LENGTH: 1644
<212> TYPE: DNA
<213> ORGANISM: Penicillium swiecickii

<400> SEQUENCE: 30

```
atggcctcca ctctttcttt caacatttac aaaaacgccc tgctctttgc tgccttccta      60
ggggctgcga aggcacagca agtcggcaca aatacggctg aggttcaccc gtctttgaca     120
tggcagaagt gtaccgctgg aggtacatgc acttcgcaat ccggcaaggt cgtcgttgac     180
gcaaactggc gctggcttca cagcaccagt ggctccacca attgctatac cggcaatacg     240
tgggatgcta ctctttgccc agatgatgtg acttgtgcca cgaactgcgc gctcgacggt     300
gccgactata ccggcactta tggtgttacg gctagcggca gctcattgcg gttgaacttc     360
gtcaccacag cctctcagaa gaacattggc tcgcgtctct atcttatgga gaatgatacc     420
aagtaccaaa tgttccagct gctcaaccag gaattcacct ttgatgtcga tgtttccaac     480
cttccttgcg gcttgaacgg cgcgctatac ttcgtgtcca tggactccga cggaggaatg     540
gccagatatc ctgccaacaa agccggtgcc aagtatggaa ctggctactg tgattcgcaa     600
tgcccgcgtg atctcaagtt catcaacggt caagctaatg tggagggatg ggtgccatcc     660
tccaacgatg tcaacgccgg cactggcaac cacgggtctt gctgtgcaga gatggatatc     720
tgggaggcca actcgatctc caatgcggtg actcctcatc catgtgacac tccaactcaa     780
gtccagtgca ccggagatgc ctgtggcggt acatacagct ctgaccgcta cggtggtact     840
tgtgaccccg acggatgtga tttcaacccg taccgccagg gtaaccagtc cttctacggc     900
ccgagcaaga tcgtggatac cacgtctcca tttaccgtgg tgactcaatt tatcaccaat     960
gacggtacct ccacgggtac tctgtcggag atcaagcgct tctacgtcca gaatggcaag    1020
gtcatccccc agtcagtatc taccatcagc gctgtgagcg gcaactctat caccgactcc    1080
tactgcgccg cccagaagaa agccttcggg gataccgacg tcttcactaa gcatggaggc    1140
atggcaggca tgggcgctgg tcttgatgaa ggcatggttc tcgtgatgag tctctgggat    1200
gaccacgccg ccaatatgct ctggctggac agcatatacc ccacgaccgc cacctcgact    1260
acgccaggtg ctgctcgcgg tagctgtgat atttcctctg gcaccccgac cgatgttgaa    1320
gctaaccacg ccaacgccta cgtcatctac tcgaacatca aggtcggccc tctcggttct    1380
accttcaact caggtagctc tggctctggc actacaacca ccactaccac caaggccact    1440
accactacca ctaccaaggc taccaccacc actactggat caaccacgac cggtgctgcc    1500
cactatgcgc aatgcggtgg atctagctgg actggtgcca ccacttgtgc cagcccgtac    1560
acttgccaga agcagaatga cttctactcc cagtgtctgt aggagatgca tctatcagta    1620
gcttgatgtt atgaccatgt ggcg                                           1644
```

<210> SEQ ID NO 31
<211> LENGTH: 1397
<212> TYPE: DNA
<213> ORGANISM: Cladosporium antareticum

<400> SEQUENCE: 31

```
atgaagtctt ctttcatcgc tgttgcagcg gcatcgaccg tcggatctgc gtatgcccaa      60
```

```
ggtcaggcat atgcccagtg tggaggtgta ggctggtcgg gttcgacgag ctgtgtctct    120

ggatatacct gcaccaagac aaacgactac tacagccaat gcctgcccgg tggcggcagc    180

aacccaacta cgacaactcg tccttctacg acaaccacat ctcggactgg aggtagcccc    240

actggaggct ctggctctgg ccgcgtctcg aatgctggcg tcaacgtgag taaaccacga    300

aatacctcca agaacacaac taaccaacaa cttccatcag atcgccggcc tcgactttgg    360

ctgcaccatc gacggaacgt gcaagaccgc caacatcgtc gaccccggcc agatcggcat    420

cgaccaaatg cagcactttg tcaaagacga cggcttgaac accttccgca tcccggtcgg    480

atggcagttc ctgctcaaca acaacctcgg cggcaccctc gactccaaca actggaacac    540

gtacgacaag cagatccaag gctgcctgaa caccggcgca gcgctttgca ttgttgacat    600

tcacaactac gcccgctgga acggtgcgat cgttggccag ggtggtccga cgaacgccca    660

gttcaccagc ctttggtcgc agatcgcggc caagtataag gggaacaaca agatcgcttt    720

cggtctgatg aacgagcccg taagcgaaac ccgaacctca accttacgaa gaaaacatac    780

tgacaagaat cccaccagca cgacctaaac atcaacacct gggcccaaac cgtccaagaa    840

gccgtcacgg ccatccgcaa agccggcgca accagcaaca agatcctgct accgggcacc    900

gacttcacct cggcgggcgc cttcatctcc aacgggtccg gtggcgccct gatcaaagtg    960

accaacctcg acggcagcac gacgaacctg atcttcgacg tgcacaagta cctcgactcg   1020

gataactcgg gcacgcacac gacgtgcacg accaacaacg ccgaggcctt cacgtcgctg   1080

ggcaactggc tgcgcacgaa caagcgccag gcgatcctca ccgagaccgg gggtggaccg   1140

aatgatgcga gctgcttgaa agctgtgtgc gagcagttgg atgtgctgaa cagctactct   1200

gacgtgtact tggggtggac tgggtggagc gcgggccggt ttgacgcgac ctatgagttg   1260

accgagacgc cgacgcgcaa tggcaatggc ggctggaccg atgtgccgct tgttactcag   1320

tgcattgctg gcaagttcaa gagatagagg ggttggggaa tcgccggtag atctttgctg   1380

gatttgtagt ccagtcg                                                  1397
```

<210> SEQ ID NO 32
<211> LENGTH: 2906
<212> TYPE: DNA
<213> ORGANISM: Talaromyces pinophilus

<400> SEQUENCE: 32

```
atgcggaaca gtttattgat ttcgcttgct gcggcagcac ttgccgaggg caaggtgagt     60

ctcttcctca attgatccca tcatccaata ttagaacatg aactaaccgt tgcattctac    120

ttcaggcata ctctcctccc gcataccctg ctccctgggc cagcggcgcc ggggaatggg    180

ctcaagctca tcaaagagct gtcgagttcg tctcgcaatt gaccttggcc gaaaaaataa    240

acttgacgac cggtgttggg tatgttgagg aaccattgag caaatattca ctacactgga    300

ctgacaattg gcagctggga gggagggcaa tgtgtcggca acactggaag cattccccgt    360

ttgggcttcc gcagcctctg catgcaggat tcaccactcg gtgtgagaga cagtatgtcg    420

tacccccttt acctctttct tcttatttta tttcttgaaa ctagggtcca ggatatagct    480

gactgtttta ctttctccag ctgattataa tactgccttc cctgctggag tcaatgtcgc    540

cgctacttgg gatctcgatc ttgcctaccg acgcggtata gccatggccg aagaacaccg    600

tggcaaaggt gtggacgtgc aacttggtcc cgttgctggt ccgctaggaa gagtaccaga    660

gggtggccgg aactgggaag gtttcgcgcc ggaccctgtg ttgactggtc agatgatggc    720

aagcactatc caaggcatgc aggataccgg tgtgattgct tgcgcaaagc actatattgg    780
```

```
aaacgaacaa gagcacttcc gtcagggctc tcaggagaac ttcaccgttg ctgatgctat    840
cagctcgaac attgatgaca ttactttgca cgaattgtac ctgtggccgt ttgccgatgc    900
ggttagggca ggtgtcggtt ccgtcatgtg ttcttacaat caaataaata acagctactc    960
ctgcggcaac agctacaccc tgaaccacat cctcaagggt gaactcgact tccaaggatt   1020
tgtaatgacc gattggagtg ctcaacactc tggtgtcggc gatgctcttg ccggagctga   1080
catggatatg cctggtgatg tggctttcga cagtggaact gctttctggg gtaccaactt   1140
gacaattgcc gtgctcaatg gcactgttcc cgaatggcgt gttgacgaca tggctgttcg   1200
tatcatgtct gctttctaca aggttggtcg tgatcgtacc caggtcccca tcaacttcgc   1260
tagctggacc ttggatacct atggcaacga atactactac gccggcgagg gctacaagga   1320
aatcaaccag cacgttgatg tgcgtggtgg ccacgccaaa gtcgtccgtg aaatcggcag   1380
tgccagcatt gttctcctca agaacgttga tggtgctctt ccattgactg gctcggagaa   1440
gtttgtcgca gtatttggag aggacgcagg ctccaacccc gacggtgtca atggctgctc   1500
tgaccgtggc tgtgataacg gtaccttggc catgggatgg ggtagtggta ctgccaactt   1560
cccttacttg gtcacccctg aacaagctat ccaggccgaa gtcgtgaaga acggcggtat   1620
gtttactgct attaccgaca gcggcgccac cgatacagcc aagaccgtgg ctgctcaagc   1680
ttcgtaagta ttcctgctca tgattatacg aatttgctag cttcagatga ctgatttgtc   1740
ttgattaggg cttgcctagt gtttgccaat gcagactccg gagaaggata catcaccgtt   1800
gacggcaatg tgggagatcg taagaacttg acattgtggc agaacggtga agctatgatc   1860
tcggccgtcg caggtaactg caacaatacc attgtcgttc ttcatactgt tggacccgtt   1920
cttgtcgagg actgggtgca ccaccctaac atcactgctg ttttgtgggc tggtctgcct   1980
ggagagcaga gcggtaactc cttggttgat gttctctacg gcagtgtcaa cccgggaggc   2040
aagactcctt tcacctgggg caagcaacgt tctgactggg gagttgatgt catttacgaa   2100
cccaacaatg gagacggcgc tcctcagcag gacttcactg agggtatctt cattgattac   2160
cgacactttg acaaatacaa cattaccccc acctacgaat tcggttatgg tctcagctac   2220
agcaccttct cattctcaga cctcaaggtg actcctatcg ctgcttctcc ttaccgacca   2280
gccaagggtc agagcggtcc ggcacctgtg ctaggcaagg ttttgaacgc cacggcctat   2340
ctgttccctg actacatcaa acgcattgaa gcgttcattt acccatggct caactccact   2400
gatcttaaga cttcctctgg tgatccaaac tacggctggc caacttccaa gtacgtgcct   2460
gacggtgctc aagacgggtc tccacaacct gtcaaccccg ccggtggtgc tcctggtggt   2520
aaccctgctc tgtatgaccc tgttgccgaa gtcactgtca ccgtcaagaa cactggaaag   2580
gtcgctggtg tcgaagtgcc ccaactctat gtttcgctcg gtggtccctc cgatgcaccc   2640
aaggttcttc gtggctttgg ccgtatttct ctcggcgctg gcgaggagac tcaatggact   2700
gccactttga cccgacgtga cgtatctaac tgggacactg tcagacaaaa ctgggttgtc   2760
acaaactaca ccaagactgt ttacgttggc aactcttctc gcaacttgcc gctccagcag   2820
actttggctc tcaacattgg acactaataa ttcggtatgg tgattctttt cttgtataaa   2880
ttttggatcg gcttccaccc ttttgt                                        2906
```

<210> SEQ ID NO 33
<211> LENGTH: 36
<212> TYPE: DNA
<213> ORGANISM: Artificial Sequence
<220> FEATURE:

<223> OTHER INFORMATION: Artificial Primer

<400> SEQUENCE: 33
acacaactgg ggatccacca tggcctccac tctttc 36

<210> SEQ ID NO 34
<211> LENGTH: 39
<212> TYPE: DNA
<213> ORGANISM: Artificial Sequence
<220> FEATURE:
<223> OTHER INFORMATION: Artificial Primer

<400> SEQUENCE: 34
ccctctagat ctcgagcgcc acatggtcat aacatcaag 39

<210> SEQ ID NO 35
<211> LENGTH: 43
<212> TYPE: DNA
<213> ORGANISM: Artificial Sequence
<220> FEATURE:
<223> OTHER INFORMATION: Artificial Primer

<400> SEQUENCE: 35
acacaactgg ggatccacca tgctgcgata tctttccatt gtt 43

<210> SEQ ID NO 36
<211> LENGTH: 42
<212> TYPE: DNA
<213> ORGANISM: Artificial Sequence
<220> FEATURE:
<223> OTHER INFORMATION: Artificial Primer

<400> SEQUENCE: 36
ccctctagat ctcgagaaag gatattggtg cagtcaaagc tg 42

<210> SEQ ID NO 37
<211> LENGTH: 46
<212> TYPE: DNA
<213> ORGANISM: Artificial Sequence
<220> FEATURE:
<223> OTHER INFORMATION: Artificial Primer

<400> SEQUENCE: 37
acacaactgg ggatccacca tgaagtcttc tttcatcgct gttgca 46

<210> SEQ ID NO 38
<211> LENGTH: 48
<212> TYPE: DNA
<213> ORGANISM: Artificial Sequence
<220> FEATURE:
<223> OTHER INFORMATION: Artificial Primer

<400> SEQUENCE: 38
gtcaccctct agatctcgag cgactggact acaaatccag caaagatc 48

<210> SEQ ID NO 39
<211> LENGTH: 43
<212> TYPE: DNA
<213> ORGANISM: Artificial Sequence
<220> FEATURE:
<223> OTHER INFORMATION: Artificial Primer

<400> SEQUENCE: 39
acacaactgg ggatccacca tgcggaacag tttattgatt tcg 43

<210> SEQ ID NO 40
<211> LENGTH: 37
<212> TYPE: DNA
<213> ORGANISM: Artificial Sequence
<220> FEATURE:
<223> OTHER INFORMATION: Artificial Primer

<400> SEQUENCE: 40
gtcaccctct agatctacaa aagggtggaa gccgatc 37

<210> SEQ ID NO 41
<211> LENGTH: 19
<212> TYPE: DNA
<213> ORGANISM: Artificial Sequence
<220> FEATURE:
<223> OTHER INFORMATION: Artificial Primer

<400> SEQUENCE: 41
tcttttcgcg ccctggaaa 19

<210> SEQ ID NO 42
<211> LENGTH: 37
<212> TYPE: DNA
<213> ORGANISM: Artificial Sequence
<220> FEATURE:
<223> OTHER INFORMATION: Artificial Primer

<400> SEQUENCE: 42
tttgtttgtt tatgtgtgtt tattcgaaac taagttc 37

<210> SEQ ID NO 43
<211> LENGTH: 22
<212> TYPE: DNA
<213> ORGANISM: Artificial Sequence
<220> FEATURE:
<223> OTHER INFORMATION: Artificial Primer

<400> SEQUENCE: 43
acagaagacg ggagacacta gc 22

<210> SEQ ID NO 44
<211> LENGTH: 32
<212> TYPE: DNA
<213> ORGANISM: Artificial Sequence
<220> FEATURE:
<223> OTHER INFORMATION: Artificial Primer

<400> SEQUENCE: 44
tcagtccaat gacagtattt tctccttctc ac 32

<210> SEQ ID NO 45
<211> LENGTH: 25
<212> TYPE: DNA
<213> ORGANISM: Artificial Sequence
<220> FEATURE:
<223> OTHER INFORMATION: Artificial Primer

<400> SEQUENCE: 45
aacgacagca caaaggaact ttcac 25

<210> SEQ ID NO 46
<211> LENGTH: 39
<212> TYPE: DNA
<213> ORGANISM: Artificial Sequence
<220> FEATURE:
<223> OTHER INFORMATION: Artificial Primer

<400> SEQUENCE: 46
ttttattgta tgtgtgtgtg tttgaaacta aagttcttg 39

<210> SEQ ID NO 47
<211> LENGTH: 31
<212> TYPE: DNA
<213> ORGANISM: Artificial Sequence
<220> FEATURE:
<223> OTHER INFORMATION: Artificial Primer

<400> SEQUENCE: 47
gccattagta gtgtactcaa acgaattatt g 31

<210> SEQ ID NO 48
<211> LENGTH: 31
<212> TYPE: DNA
<213> ORGANISM: Artificial Sequence
<220> FEATURE:
<223> OTHER INFORMATION: Artificial Primer

<400> SEQUENCE: 48
ggctactgat tttgttaagc aactcatcaa g 31

<210> SEQ ID NO 49
<211> LENGTH: 31
<212> TYPE: DNA
<213> ORGANISM: Artificial Sequence
<220> FEATURE:
<223> OTHER INFORMATION: Artificial Primer

<400> SEQUENCE: 49
gccattagta gtgtactcaa acgaattatt g 31

<210> SEQ ID NO 50
<211> LENGTH: 36
<212> TYPE: DNA
<213> ORGANISM: Artificial Sequence
<220> FEATURE:
<223> OTHER INFORMATION: Artificial Primer

<400> SEQUENCE: 50
gtttagttaa ttatagttcg ttgactgtgt ttcttg 36

<210> SEQ ID NO 51
<211> LENGTH: 28
<212> TYPE: DNA
<213> ORGANISM: Artificial Sequence
<220> FEATURE:
<223> OTHER INFORMATION: Artificial Primer

<400> SEQUENCE: 51
ggtctccttt ctttcaagaa acacagtc 28

<210> SEQ ID NO 52
<211> LENGTH: 39
<212> TYPE: DNA
<213> ORGANISM: Artificial Sequence
<220> FEATURE:
<223> OTHER INFORMATION: Artificial Primer

<400> SEQUENCE: 52
atgatgaaaa aataagcaga aaagactaat aattcttag 39

<210> SEQ ID NO 53
<211> LENGTH: 35

<212> TYPE: DNA
<213> ORGANISM: Artificial Sequence
<220> FEATURE:
<223> OTHER INFORMATION: Artificial Primer

<400> SEQUENCE: 53
agtgctttta actaagaatt attagtcttt tctgc 35

<210> SEQ ID NO 54
<211> LENGTH: 31
<212> TYPE: DNA
<213> ORGANISM: Artificial Sequence
<220> FEATURE:
<223> OTHER INFORMATION: Artificial Primer

<400> SEQUENCE: 54
ggctactgat tttgttaagc aactcatcaa g 31

<210> SEQ ID NO 55
<211> LENGTH: 28
<212> TYPE: DNA
<213> ORGANISM: Artificial Sequence
<220> FEATURE:
<223> OTHER INFORMATION: Artificial Primer

<400> SEQUENCE: 55
ggtctccttt ctttcaagaa acacagtc 28

<210> SEQ ID NO 56
<211> LENGTH: 39
<212> TYPE: DNA
<213> ORGANISM: Artificial Sequence
<220> FEATURE:
<223> OTHER INFORMATION: Artificial Primer

<400> SEQUENCE: 56
atgatgaaaa aataagcaga aaagactaat aattcttag 39

<210> SEQ ID NO 57
<211> LENGTH: 418
<212> TYPE: PRT
<213> ORGANISM: Trichoderma reesei

<400> SEQUENCE: 57

Met Asn Lys Ser Val Ala Pro Leu Leu Leu Ala Ala Ser Ile Leu Tyr
1 5 10 15

Gly Gly Ala Ala Ala Gln Gln Thr Val Trp Gly Gln Cys Gly Gly Ile
20 25 30

Gly Trp Ser Gly Pro Thr Asn Cys Ala Pro Gly Ser Ala Cys Ser Thr
35 40 45

Leu Asn Pro Tyr Tyr Ala Gln Cys Ile Pro Gly Ala Thr Thr Ile Thr
50 55 60

Thr Ser Thr Arg Pro Pro Ser Gly Pro Thr Thr Thr Thr Arg Ala Thr
65 70 75 80

Ser Thr Ser Ser Ser Thr Pro Pro Thr Ser Ser Gly Val Arg Phe Ala
85 90 95

Gly Val Asn Ile Ala Gly Phe Asp Phe Gly Cys Thr Thr Asp Gly Thr
100 105 110

Cys Val Thr Ser Lys Val Tyr Pro Pro Leu Lys Asn Phe Thr Gly Ser
115 120 125

Asn Asn Tyr Pro Asp Gly Ile Gly Gln Met Gln His Phe Val Asn Asp
130 135 140

```
Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 58
<211> LENGTH: 844
<212> TYPE: PRT
<213> ORGANISM: Aspergillus fumigatus

<400> SEQUENCE: 58

```
Gln Glu Leu Ala Phe Ser Pro Pro Phe Tyr Pro Ser Pro Trp Ala Asp
1               5                   10                  15

Gly Gln Gly Glu Trp Ala Asp Ala His Arg Arg Ala Val Glu Ile Val
            20                  25                  30

Ser Gln Met Thr Leu Ala Glu Lys Val Asn Leu Thr Thr Gly Thr Gly
        35                  40                  45

Trp Glu Met Asp Arg Cys Val Gly Gln Thr Gly Ser Val Pro Arg Leu
    50                  55                  60

Gly Ile Asn Trp Gly Leu Cys Gly Gln Asp Ser Pro Leu Gly Ile Arg
65                  70                  75                  80

Asp Ser Asp Leu Asn Ser Ala Phe Pro Ala Gly Thr Asn Val Ala Ala
                85                  90                  95
```

```
Thr Trp Asp Lys Thr Leu Ala Tyr Leu Arg Gly Lys Ala Met Gly Glu
            100                 105                 110

Glu Phe Asn Asp Lys Gly Val Asp Ile Leu Leu Gly Pro Ala Ala Gly
        115                 120                 125

Pro Leu Gly Lys Tyr Pro Asp Gly Gly Arg Ile Trp Glu Gly Phe Ser
    130                 135                 140

Pro Asp Pro Val Leu Thr Gly Val Leu Phe Ala Glu Thr Ile Lys Gly
145                 150                 155                 160

Ile Gln Asp Ala Gly Val Ile Ala Thr Ala Lys His Tyr Ile Leu Asn
                165                 170                 175

Glu Gln Glu His Phe Arg Gln Val Gly Glu Ala Gln Gly Tyr Gly Tyr
            180                 185                 190

Asn Ile Thr Glu Thr Ile Ser Ser Asn Val Asp Asp Lys Thr Met His
        195                 200                 205

Glu Leu Tyr Leu Trp Pro Phe Ala Asp Ala Val Arg Ala Gly Val Gly
    210                 215                 220

Ala Val Met Cys Ser Tyr Asn Gln Ile Asn Asn Ser Tyr Gly Cys Gln
225                 230                 235                 240

Asn Ser Gln Thr Leu Asn Lys Leu Leu Lys Ala Glu Leu Gly Phe Gln
                245                 250                 255

Gly Phe Val Met Ser Asp Trp Gly Ala His His Ser Gly Val Gly Ala
            260                 265                 270

Ala Leu Ala Gly Leu Asp Met Ser Met Pro Gly Asp Ile Ser Phe Asp
        275                 280                 285

Asp Gly Leu Ser Phe Trp Gly Thr Asn Leu Thr Val Ser Val Leu Asn
    290                 295                 300

Gly Thr Val Pro Ala Trp Arg Val Asp Asp Met Ala Val Arg Ile Met
305                 310                 315                 320

Thr Ala Tyr Tyr Lys Val Gly Arg Asp Arg Leu Arg Ile Pro Pro Asn
                325                 330                 335

Phe Ser Ser Trp Thr Arg Asp Glu Tyr Gly Trp Glu His Ser Ala Val
            340                 345                 350

Ser Glu Gly Ala Trp Thr Lys Val Asn Asp Phe Val Asn Val Gln Arg
        355                 360                 365

Ser His Ser Gln Ile Ile Arg Glu Ile Gly Ala Ala Ser Thr Val Leu
    370                 375                 380

Leu Lys Asn Thr Gly Ala Leu Pro Leu Thr Gly Lys Glu Val Lys Val
385                 390                 395                 400

Gly Val Leu Gly Glu Asp Ala Gly Ser Asn Pro Trp Gly Ala Asn Gly
                405                 410                 415

Cys Pro Asp Arg Gly Cys Asp Asn Gly Thr Leu Ala Met Ala Trp Gly
            420                 425                 430

Ser Gly Thr Ala Glu Phe Pro Tyr Leu Val Thr Pro Glu Gln Ala Ile
        435                 440                 445

Gln Arg Glu Val Ile Ser Asn Gly Gly Asn Val Phe Ala Val Thr Asp
    450                 455                 460

Asn Gly Ala Leu Ser Gln Met Ala Asp Val Ala Ser Gln Ser Ser Val
465                 470                 475                 480

Ser Leu Val Phe Val Asn Ala Asp Ser Gly Glu Gly Tyr Ile Ser Val
                485                 490                 495

Asp Gly Asn Glu Gly Asp Arg Lys Asn Leu Thr Leu Trp Lys Asn Gly
            500                 505                 510
```

```
Glu Ala Val Ile Asp Thr Val Val Ser His Cys Asn Asn Thr Ile Val
        515                 520                 525

Val Ile His Ser Val Gly Pro Val Leu Ile Asp Arg Trp Tyr Asp Asn
    530                 535                 540

Pro Asn Val Thr Ala Ile Ile Trp Ala Gly Leu Pro Gly Gln Glu Ser
545                 550                 555                 560

Gly Asn Ser Leu Val Asp Val Leu Tyr Gly Arg Val Asn Pro Ser Ala
                565                 570                 575

Lys Thr Pro Phe Thr Trp Gly Lys Thr Arg Glu Ser Tyr Gly Ala Pro
            580                 585                 590

Leu Leu Thr Glu Pro Asn Asn Gly Asn Gly Ala Pro Gln Asp Asp Phe
        595                 600                 605

Asn Glu Gly Val Phe Ile Asp Tyr Arg His Phe Asp Lys Arg Asn Glu
    610                 615                 620

Thr Pro Ile Tyr Glu Phe Gly His Gly Leu Ser Tyr Thr Thr Phe Gly
625                 630                 635                 640

Tyr Ser His Leu Arg Val Gln Ala Leu Asn Ser Ser Ser Ser Ala Tyr
                645                 650                 655

Val Pro Thr Ser Gly Glu Thr Lys Pro Ala Pro Thr Tyr Gly Glu Ile
            660                 665                 670

Gly Ser Ala Ala Asp Tyr Leu Tyr Pro Glu Gly Leu Lys Arg Ile Thr
        675                 680                 685

Lys Phe Ile Tyr Pro Trp Leu Asn Ser Thr Asp Leu Glu Asp Ser Ser
    690                 695                 700

Asp Asp Pro Asn Tyr Gly Trp Glu Asp Ser Glu Tyr Ile Pro Glu Gly
705                 710                 715                 720

Ala Arg Asp Gly Ser Pro Gln Pro Leu Leu Lys Ala Gly Gly Ala Pro
                725                 730                 735

Gly Gly Asn Pro Thr Leu Tyr Gln Asp Leu Val Arg Val Ser Ala Thr
            740                 745                 750

Ile Thr Asn Thr Gly Asn Val Ala Gly Tyr Glu Val Pro Gln Leu Tyr
        755                 760                 765

Val Ser Leu Gly Gly Pro Asn Glu Pro Arg Val Val Leu Arg Lys Phe
    770                 775                 780

Asp Arg Ile Phe Leu Ala Pro Gly Glu Gln Lys Val Trp Thr Thr Thr
785                 790                 795                 800

Leu Asn Arg Arg Asp Leu Ala Asn Trp Asp Val Glu Ala Gln Asp Trp
                805                 810                 815

Val Ile Thr Lys Tyr Pro Lys Lys Val His Val Gly Ser Ser Ser Arg
            820                 825                 830

Lys Leu Pro Leu Arg Ala Pro Leu Pro Arg Val Tyr
        835                 840
```

<210> SEQ ID NO 59
<211> LENGTH: 405
<212> TYPE: PRT
<213> ORGANISM: Evansstolkia leycettana

<400> SEQUENCE: 59

```
Met Val His Leu Ser Ser Leu Ala Leu Ala Leu Ala Ala Gly Ser Gln
1               5                   10                  15

Leu Ala Gln Ala Ala Gly Leu Asn Thr Ala Ala Lys Ala Ile Gly Lys
            20                  25                  30

Leu Tyr Phe Gly Thr Ala Thr Asp Asn Pro Glu Leu Ser Asp Ser Thr
        35                  40                  45
```

```
Tyr Met Gln Glu Thr Asp Asn Thr Asp Asp Phe Gly Gln Leu Thr Pro
    50                  55                  60

Ala Asn Ser Met Lys Trp Asp Ala Thr Glu Pro Ser Gln Asn Thr Phe
65                  70                  75                  80

Thr Phe Thr Asn Gly Asp Gln Ile Ala Asn Leu Ala Lys Ser Asn Gly
                85                  90                  95

Gln Met Leu Arg Cys His Asn Leu Val Trp Tyr Asn Gln Leu Pro Ser
            100                 105                 110

Trp Val Thr Ser Gly Ser Trp Thr Asn Ala Thr Leu Leu Ala Ala Met
        115                 120                 125

Lys Asn His Ile Thr Asn Val Val Thr His Tyr Lys Gly Gln Cys Tyr
    130                 135                 140

Ala Trp Asp Val Val Asn Glu Ala Leu Asn Asp Asp Gly Thr Tyr Arg
145                 150                 155                 160

Ser Asn Val Phe Tyr Gln Tyr Ile Gly Glu Ala Tyr Ile Pro Ile Ala
                165                 170                 175

Phe Ala Thr Ala Ala Ala Ala Asp Pro Asn Ala Lys Leu Tyr Tyr Asn
            180                 185                 190

Asp Tyr Asn Ile Glu Tyr Pro Gly Ala Lys Ala Thr Ala Ala Gln Asn
        195                 200                 205

Ile Val Lys Met Val Lys Ala Tyr Gly Ala Lys Ile Asp Gly Val Gly
    210                 215                 220

Leu Gln Ser His Phe Ile Val Gly Ser Thr Pro Ser Gln Ser Ser Gln
225                 230                 235                 240

Gln Ser Asn Met Ala Ala Phe Thr Ala Leu Gly Val Glu Val Ala Ile
                245                 250                 255

Thr Glu Leu Asp Ile Arg Met Thr Leu Pro Ser Thr Ser Ala Leu Leu
            260                 265                 270

Ala Gln Gln Ser Thr Asp Tyr Gln Ser Thr Val Ser Ala Cys Val Asn
        275                 280                 285

Thr Pro Lys Cys Ile Gly Ile Thr Leu Trp Asp Trp Thr Asp Lys Tyr
    290                 295                 300

Ser Trp Val Pro Asn Thr Phe Ser Gly Gln Gly Asp Ala Cys Pro Trp
305                 310                 315                 320

Asp Ser Asn Tyr Gln Lys Lys Pro Ala Tyr Tyr Gly Ile Leu Thr Ala
                325                 330                 335

Leu Gly Gly Ser Ala Ser Thr Ser Thr Thr Thr Thr Leu Val Thr Ser
            340                 345                 350

Thr Arg Thr Ser Thr Thr Thr Ser Thr Ser Ala Thr Ser Thr Ser Thr
        355                 360                 365

Gly Val Ala Gln His Trp Gly Gln Cys Gly Gly Ile Gly Trp Thr Gly
    370                 375                 380

Pro Thr Thr Cys Ala Ser Pro Tyr Thr Cys Gln Glu Leu Asn Pro Tyr
385                 390                 395                 400

Tyr Tyr Gln Cys Leu
                405


<210> SEQ ID NO 60
<211> LENGTH: 325
<212> TYPE: PRT
<213> ORGANISM: Talaromyces pinophilus

<400> SEQUENCE: 60

Met His Phe Leu Ala Ala Leu Leu Ala Val Leu Pro Leu Val Ser Gly
```

-continued

```
1               5                   10                  15

Ser Pro Val Pro Glu Lys Arg Ser Gly Cys Ala Leu Pro Ser Thr Tyr
            20                  25                  30

Lys Trp Thr Ser Thr Gly Pro Leu Ala Ser Pro Lys Ser Gly Leu Val
        35                  40                  45

Ala Leu Arg Asp Tyr Ser His Val Ile Tyr Asn Gly Gln His Leu Val
    50                  55                  60

Tyr Gly Ser Thr Ala Asn Thr Ala Gly Ser Tyr Gly Ser Met Asn Phe
65                  70                  75                  80

Gly Leu Phe Ser Asp Trp Ser Glu Met Ser Ser Ala Ser Gln Asn Thr
                85                  90                  95

Met Ser Thr Gly Ala Val Ala Pro Thr Ile Phe Tyr Phe Ala Pro Lys
            100                 105                 110

Ser Val Trp Ile Leu Ala Tyr Gln Trp Gly Pro Tyr Ala Phe Ser Tyr
        115                 120                 125

Arg Thr Ser Thr Asp Pro Ser Asn Ala Asn Gly Trp Ser Ser Pro Gln
    130                 135                 140

Pro Leu Phe Thr Gly Thr Ile Ser Gly Ser Ser Thr Gly Val Ile Asp
145                 150                 155                 160

Gln Thr Val Ile Gly Asp Ser Glu Asn Met Tyr Leu Phe Phe Ala Gly
                165                 170                 175

Asp Asn Gly His Ile Tyr Arg Ala Ser Met Pro Ile Gly Asp Phe Pro
            180                 185                 190

Gly Ser Phe Gly Ser Ala Ser Thr Ile Val Leu Ser Asp Ser Thr Asn
        195                 200                 205

Asn Leu Phe Glu Ala Val Glu Val Tyr Thr Val Glu Gly Gln Asn Gln
    210                 215                 220

Tyr Leu Met Ile Val Glu Ala Ile Gly Ala Asn Gly Arg Tyr Phe Arg
225                 230                 235                 240

Ser Phe Thr Ala Ser Ser Leu Gly Gly Thr Trp Thr Ala Gln Ala Ser
                245                 250                 255

Thr Glu Ser Asn Pro Phe Ala Gly Lys Ala Asn Ser Gly Ala Thr Trp
            260                 265                 270

Thr Asn Asp Ile Ser Ser Gly Asp Leu Val Arg Thr Asn Pro Asp Gln
        275                 280                 285

Thr Gln Thr Ile Asp Ala Cys Asn Leu Gln Phe Leu Tyr Gln Gly Arg
    290                 295                 300

Ser Thr Ser Ser Gly Gly Asp Tyr Asn Leu Leu Pro Tyr Gln Pro Gly
305                 310                 315                 320

Leu Leu Thr Leu Ala
                325
```